(12) United States Patent
Chen et al.

(10) Patent No.: US 9,012,463 B2
(45) Date of Patent: *Apr. 21, 2015

(54) INHIBITORS OF BRUTON'S TYROSINE KINASE

(75) Inventors: Wei Chen, Fremont, CA (US); David J. Loury, San Jose, CA (US); Tarak D. Mody, Sunnyvale, CA (US); Erik Verner, Belmont, CA (US); Mark Stephen Smyth, Foster City, CA (US); Wenchen Luo, Palo Alto, CA (US)

(73) Assignee: Pharmacyclics, Inc., Sunnyvale, CA (US)

( * ) Notice: Subject to any disclaimer, the term of this patent is extended or adjusted under 35 U.S.C. 154(b) by 256 days.

This patent is subject to a terminal disclaimer.

(21) Appl. No.: 12/903,101

(22) Filed: Oct. 12, 2010

(65) Prior Publication Data

US 2011/0086866 A1 Apr. 14, 2011

Related U.S. Application Data

(60) Provisional application No. 61/250,787, filed on Oct. 12, 2009.

(51) Int. Cl.
| | | |
|---|---|---|
| C07D 487/04 | (2006.01) | |
| A61K 31/519 | (2006.01) | |
| A61P 35/00 | (2006.01) | |
| A61P 29/00 | (2006.01) | |
| C07D 519/00 | (2006.01) | |

(52) U.S. Cl.
CPC ............ *C07D 487/04* (2013.01); *C07D 519/00* (2013.01)

(58) Field of Classification Search
CPC ............................ A61K 31/519; C07D 487/04
USPC ........................................ 544/262; 514/262.1
See application file for complete search history.

(56) References Cited

U.S. PATENT DOCUMENTS

| | | |
|---|---|---|
| 6,660,744 B1 | 12/2003 | Hirst et al. |
| 6,921,763 B2 | 7/2005 | Hirst et al. |
| 7,332,497 B2 | 2/2008 | Hirst et al. |
| 7,514,444 B2 | 4/2009 | Honigberg et al. |
| 7,718,662 B1 | 5/2010 | Chen |
| 7,741,330 B1 | 6/2010 | Chen |
| 2008/0076921 A1 | 3/2008 | Honigberg et al. |
| 2008/0108636 A1 | 5/2008 | Honigberg et al. |
| 2008/0139582 A1 | 6/2008 | Honigberg et al. |
| 2009/0181987 A1 | 7/2009 | Honigberg et al. |

FOREIGN PATENT DOCUMENTS

| | | | |
|---|---|---|---|
| WO | WO 01/19829 | * | 3/2001 |
| WO | WO-2011-046771 | | 4/2011 |

OTHER PUBLICATIONS

Chang et al., "The Bruton tyrosine kinase inhbitor PCI-32765 ameliorates autoimmune arthritis by inhibition of multiple effector cells," Arthritis Research & Therapy 13:R115 (2011).
PCT/US10/52377 Search Report and Written Opinion mailed Jun. 29, 2011.
Supplementary European Search Report, EP 10 82 3966/PCTUS2010/052377; Oct. 17, 2011.
Zhengying Pan et al: "Discovery of Selective Irreversible Inhibitors for Bruton's Tyrosine Kinase," ChemMedChem 2007, pp. 58-61, vol. 2, Wiley-VCH Verlag GmbH & Co. KGaA, Weinheim.

* cited by examiner

*Primary Examiner* — Susanna Moore
(74) *Attorney, Agent, or Firm* — Wilson Sonsini Goodrich & Rosati

(57) ABSTRACT

Described herein are kinase inhibitor compounds of Formula IV:

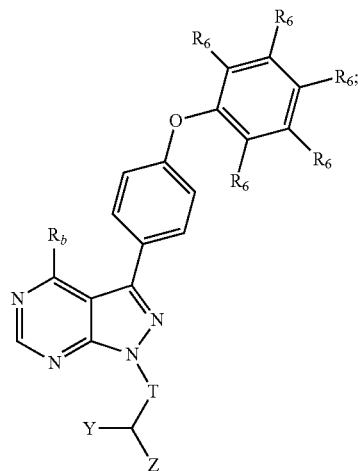

Formula (IV)

wherein $R_b$, $R_6$, T, Y, and Z are defined herein. Also described herein are methods for synthesizing such inhibitors, and methods for using such inhibitors in the treatment of diseases. Further described herein are methods, assays and systems for determining an appropriate inhibitor of a protein, including a kinase.

14 Claims, No Drawings

INHIBITORS OF BRUTON'S TYROSINE KINASE

CROSS-REFERENCE

This application claims the benefit of U.S. Provisional Application No. 61/250,787, filed Oct. 12, 2009; which is related to U.S. application Ser. No. 12/581,044 filed Oct. 16, 2009, now U.S. Pat. No. 7,718,662, issued May 18, 2010; and U.S. application Ser. No. 12/581,062, filed Oct. 16, 2009, now U.S. Pat. No. 7,741,330, issued Jun. 22, 2010; which are incorporated herein by reference in their entirety.

FIELD OF THE INVENTION

Described herein are kinase inhibitor compounds, methods for synthesizing such inhibitors, and methods for using such inhibitors in the treatment of diseases.

BACKGROUND OF THE INVENTION

A kinase, alternatively known as a phosphotransferase, is a type of enzyme that transfers phosphate groups from high-energy donor molecules, such as ATP, to specific target molecules; the process is termed phosphorylation. Protein kinases, which act on and modify the activity of specific proteins, are used to transmit signals and control complex processes in cells. Up to 518 different kinases have been identified in humans. Their enormous diversity and role in signaling makes them attractive targets for drug design.

Bruton's tyrosine kinase (Btk), a member of the Tec family of non-receptor tyrosine kinases, is a key signaling enzyme expressed in all hematopoietic cells types except T lymphocytes and natural killer cells. Btk plays an essential role in the B-cell signaling pathway linking cell surface B-cell receptor (BCR) stimulation to downstream intracellular responses.

Btk is a key regulator of B-cell development, activation, signaling, and survival (Kurosaki, Curr Op Imm, 2000, 276-281; Schaeffer and Schwartzberg, Curr Op Imm 2000, 282-288). In addition, Btk plays a role in a number of other hematopoetic cell signaling pathways, e.g., Toll like receptor (TLR) and cytokine receptor-mediated TNF-.alpha. production in macrophages, IgE receptor (FcepsilonRI) signaling in Mast cells, inhibition of Fas/APO-1 apoptotic signaling in B-lineage lymphoid cells, and collagen-stimulated platelet aggregation. See, e.g., C. A. Jeffries, et al., (2003), Journal of Biological Chemistry 278:26258-26264; N. J. Horwood, et al., (2003), The Journal of Experimental Medicine 197:1603-1611; Iwaki et al. (2005), Journal of Biological Chemistry 280(48):40261-40270; Vassilev et al. (1999), Journal of Biological Chemistry 274(3):1646-1656, and Quek et al. (1998), Current Biology 8(20):1137-1140.

SUMMARY OF THE INVENTION

Described herein are inhibitors of Bruton's tyrosine kinase (Btk). Also described herein are irreversible inhibitors of Btk. Further described are irreversible inhibitors of Btk that form a covalent bond with a cysteine residue on Btk. Further described herein are irreversible inhibitors of other tyrosine kinases, wherein the other tyrosine kinases share homology with Btk by having a cysteine residue (including a Cys 481 residue) that can form a covalent bond with the irreversible inhibitor (such tyrosine kinases, are referred herein as "Btk tyrosine kinase cysteine homologs"). Yet further described herein are methods for synthesizing such inhibitors, methods for using such inhibitors in the treatment of diseases (including diseases wherein inhibition of Btk provides therapeutic benefit to a patient having the disease). Further described are pharmaceutical formulations that include an inhibitor of Btk.

In one aspect, provided herein are compounds of Formula (I) having the structure:

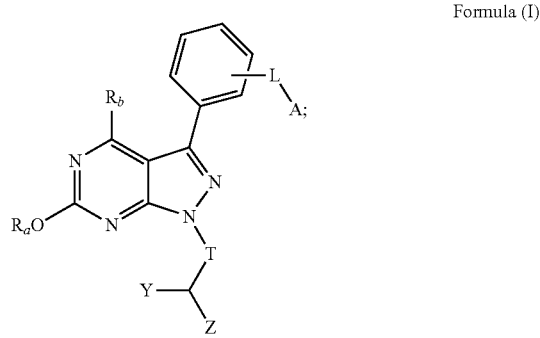

Formula (I)

wherein:

L is a bond, $CH_2$, O, $NR_2$, S, CO, $C=NR_2$, or $C=N-OR_2$;

T is a bond, $C_1$-$C_6$alkylene, or $C_3$-$C_6$cycloalkylene;

A is aryl or heteroaryl wherein aryl or heteroaryl is optionally substituted with at least one $R_1$;

Y and Z are each independently selected from H, $C_1$-$C_6$alkyl, $C_2$-$C_6$alkenyl, $C_3$-$C_{10}$cycloalkyl, $C_1$-$C_6$heteroalkyl, $C_2$-$C_6$heteroalkenyl, $C_4$-$C_{10}$heterocycloalkenyl and $C_2$-$C_{10}$heterocycloalkyl, wherein $C_1$-$C_6$alkyl, $C_2$-$C_6$alkenyl, $C_3$-$C_{10}$cycloalkyl, $C_1$-$C_6$heteroalkyl, $C_2$-$C_6$heteroalkenyl, $C_4$-$C_{10}$heterocycloalkenyl and $C_2$-$C_{10}$heterocycloalkyl are optionally substituted with at least one $R_1$; or Y and Z together with the carbon atom to which they are attached form a $C_3$-$C_{10}$cycloalkyl, $C_2$-$C_{10}$heterocycloalkyl, $C_4$-$C_{10}$heterocycloalkenyl, aryl, or heteroaryl, wherein $C_3$-$C_{10}$cycloalkyl, $C_2$-$C_{10}$heterocycloalkyl, $C_4$-$C_{10}$heterocycloalkenyl, aryl, or heteroaryl, are optionally substituted with at least one X;

wherein when Y and Z together with the carbon atom to which they are attached form a nitrogen atom-containing $C_2$-$C_{10}$heterocycloalkyl or $C_4$-$C_{10}$heterocycloalkenyl, the nitrogen atom of the $C_2$-$C_{10}$heterocycloalkyl or $C_4$-$C_{10}$heterocycloalkenyl is optionally substituted with W and the carbon atoms of the $C_2$-$C_{10}$heterocycloalkyl or $C_4$-$C_{10}$heterocycloalkenyl are optionally substituted with at least one X;

W is selected from J, $C(=O)$-J, $C(=O)O$-J, $C(=O)NR_2$-J, $C(=NR_2)$-J, $-C(=NR_2)NR_2$-J, $C(=N-OR_3)$-J, $C(=S)$-J, $S(=O)_v$-J, $S(=O)_vO$-J;

X is F, Cl, Br, I, $-CN$, $-NO_2$, $-OR_3$, $-N(R_2)_2$, $-SR_2$, $-C_1$-$C_6$alkyl, $-C(=O)R_2$, $-OC(=O)R_2$, $-NR_2C(=O)R_2$, $-NR_2C(=O)N(R_2)_2$, $-C(=O)N(R_2)_2$, $-C(=NR_2)N(R_2)_2$, $-C(=N-OR_2)N(R_2)_2$, $-C(=S)R_2$, $-S(=O)_vR_2$, $-OS(=O)_vR_2$, $-NR_2C(=O)OR_2$, $-NR_2S(=O)_vR_2$;

J is $-C_1$-$C_6$alkyl, $C_3$-$C_6$cycloalkyl, $-C_2$-$C_6$alkene, $C_2$-$C_6$heterocycloalkyl, aryl, or heteroaryl optionally substituted with at least one $R_1$;

v is 1 or 2;

$R_a$ is H, $-SO_3H$, or $C_1$-$C_4$alkyl;

$R_b$ is $NH_2$, OH, $OSO_3H$ or $NHSO_3H$;

$R_1$ is selected from F, Cl, Br, I, —CN, —NO$_2$, —SR$_2$, —OR$_3$, C$_1$-C$_6$alkyl, C$_1$-C$_6$haloalkyl, C$_1$-C$_6$hydroxyalkyl, —OC$_1$-C$_6$haloalkyl, C$_1$-C$_6$heteroalkyl, C$_3$-C$_6$cycloalkyl, C$_2$-C$_6$heterocycloalkyl, phenyl, —NR$_2$S(=O)$_2$R$_2$, —S(=O)$_2$N(R$_2$)$_2$, —C(=O)CF$_3$, —C(=O)NR$_2$S(=O)$_2$R$_2$, —S(=O)$_2$NR$_2$C(=O)R$_2$, —N(R$_2$)$_2$, wherein optionally the two R$_2$ groups of N(R$_2$)$_2$ and the nitrogen atom to which they are attached form a C$_2$-C$_6$ heterocycloalkyl ring, —NR$_2$C(=O)R$_2$, —NR$_2$C(=O)N(R$_2$)$_2$, —CO$_2$R$_2$, —C(=O)R$_2$, —OC(=O)R$_2$, —C(=O)N(R$_2$)$_2$, —OS(=O)$_2$R$_2$, —OS(=O)$_2$OR$_2$, —S(=O)R$_2$, —S(=O)$_2$R$_2$, —SO$_3$H, and at least one amino acid fragment;

$R_2$ is H, C$_1$-C$_6$alkyl, C$_1$-C$_6$haloalkyl, C$_1$-C$_6$hydroxyalkyl, or C$_3$-C$_6$cycloalkyl;

$R_3$ is H, methyl, ethyl, n-propyl, iso-propyl, n-butyl, iso-butyl, tert-butyl, or SO$_3$H; or a pharmaceutically acceptable salt, solvate, or tautomeric form thereof.

For any and all of the embodiments, substituents are optionally selected from among a subset of the listed alternatives.

In one embodiment, the tautomeric form of the compound of Formula (I) has the structure of Formula (IA):

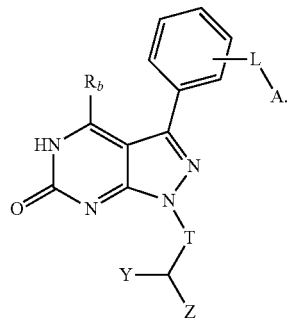

Formula (IA)

Any combination of the groups described above for the various variables is contemplated herein.

In another aspect is a compound having the structure of Formula (II):

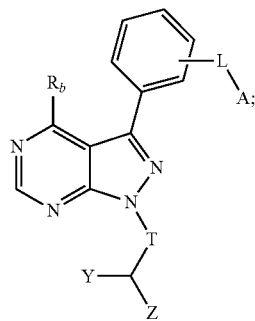

Formula (II)

wherein:
L is a bond, CH$_2$, O, NR$_3$, S, CO, C=NR$_2$, or C=N—OR$_2$;
T is a bond, C$_1$-C$_6$alkylene, or C$_3$-C$_6$cycloalkylene;
A is aryl or heteroaryl wherein aryl or heteroaryl is optionally substituted with at least one R$_1$;

Y is C$_1$-C$_6$alkylene-CO$_2$H or C$_2$-C$_6$alkenylene-C(=O)H;
Z is C$_1$-C$_6$alkylene-NR$_2$C(=O)C$_1$-C$_6$alkyl optionally substituted with at least one R$_1$; or
Y and Z together with the carbon atom to which they are attached form a

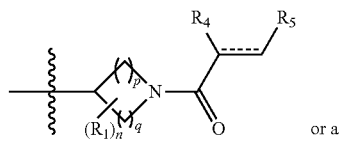 or a

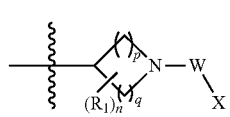

group;

⫽ is a single bond or a cis or trans-double bond;
p is 0-6;
q is 0-6; wherein p+q is ≥1;
n is 0-4;
$R_1$ is selected from F, Cl, Br, I, —CN, —NO$_2$, —SR$_2$, —OR$_3$, C$_1$-C$_6$alkyl, C$_1$-C$_6$haloalkyl, C$_1$-C$_6$hydroxyalkyl, —OC$_1$-C$_6$haloalkyl, C$_1$-C$_6$heteroalkyl, C$_3$-C$_6$cycloalkyl, C$_2$-C$_6$heterocycloalkyl, phenyl, —NR$_3$S(=O)$_2$R$_2$, —S(=O)$_2$N(R$_2$)$_2$, —C(=O)CF$_3$, —C(=O)NR$_3$S(=O)$_2$R$_2$, —S(=O)$_2$NR$_3$C(=O)R$_2$, —N(R$_2$)$_2$, wherein optionally the two R$_2$ groups of N(R$_2$)$_2$ and the nitrogen atom to which they are attached form a C$_2$-C$_6$ heterocycloalkyl ring, —NR$_2$C(=O)R$_2$, —NR$_2$C(=O)NR$_2$, —CO$_2$R$_2$, —C(=O)R$_2$, —OC(=O)R$_2$, —C(=O)N(R$_2$)$_2$, —OS(=O)$_2$R$_2$, —OS(=O)$_2$OR$_2$, —S(=O)R$_2$, —S(=O)$_2$R$_2$, and at least one amino acid fragment;

$R_b$ is NH$_2$, OH, OSO$_3$H or NHSO$_3$H;
$R_2$ is H, C$_1$-C$_6$alkyl, C$_1$-C$_6$haloalkyl, C$_1$-C$_6$hydroxyalkyl, C$_1$-C$_6$dihydroxyalkyl, or C$_3$-C$_6$cycloalkyl;
$R_3$ is H, methyl, ethyl, n-propyl, iso-propyl, n-butyl, iso-butyl, tert-butyl or SO$_3$H;
$R_4$ and $R_5$ are each independently selected from H, F, Cl, Br, I, —CN, —NO$_2$, —SR$_2$, —OR$_3$, C$_1$-C$_6$alkyl, C$_1$-C$_6$haloalkyl, C$_1$-C$_6$hydroxyalkyl, —OC$_1$-C$_6$haloalkyl, C$_1$-C$_6$heteroalkyl, C$_3$-C$_6$cycloalkyl, C$_2$-C$_6$heterocycloalkyl, phenyl, —OSO$_3$H, —NR$_2$S(=O)$_2$R$_2$, —S(=O)$_2$N(R$_2$)$_2$, —C(=O)CF$_3$, —C(=O)NR$_2$S(=O)$_2$R$_2$, —S(=O)$_2$NR$_2$C(=O)R$_2$, —N(R$_2$)$_2$, —NR$_2$C(=O)R$_2$, —CO$_2$R$_2$, —C(=O)R$_2$, —OC(=O)R$_2$, —C(=O)N(R$_2$)$_2$, —OS(=O)$_2$R$_2$, —OS(=O)$_2$OR$_2$, —S(=O)R$_2$, —S(=O)$_2$R$_2$, and at least one amino acid fragment; optionally when ⫽ is a single bond then R$_4$ and R$_5$ together with the carbon atoms to which they are attached form an epoxide; wherein when ⫽ is a single bond then R$_4$ and R$_5$ are not both hydrogen;

W is selected from —C(=O)—, —C(=O)R$_2$—, —C(=O)OR$_2$—, —C(=NR$_2$)—, —C(=N—OR$_3$)—, —(C=S)—, —S(=O)$_v$—;

X is

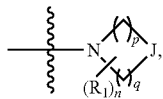

wherein J is O, NR$_6$ or C(R$_2$)$_2$.

R$_6$ is selected from H, C$_1$-C$_6$alkyl, C$_1$-C$_6$haloalkyl, C$_1$-C$_6$hydroxyalkyl, C$_1$-C$_6$heteroalkyl, C$_3$-C$_6$cycloalkyl, C$_2$-C$_6$heterocycloalkyl, phenyl, —S(=O)$_2$N(R$_2$)$_2$, —C(=O)CF$_3$, —CO$_2$R$_2$, —C(=O)R$_2$, —C(=O)N(R$_2$)$_2$, —OS(=O)$_2$R$_2$, —OS(=O)$_2$OR$_2$, —S(=O)R$_2$, —S(=O)$_2$R$_2$; or a pharmaceutically acceptable salt, tautomer, or solvate thereof.

In one embodiment is a compound selected from:

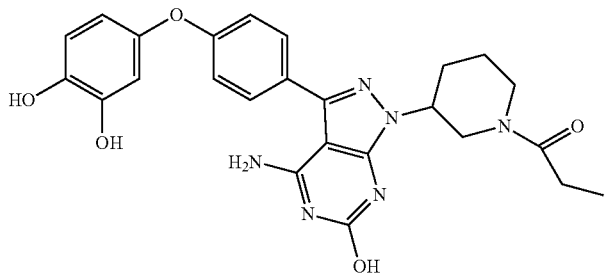

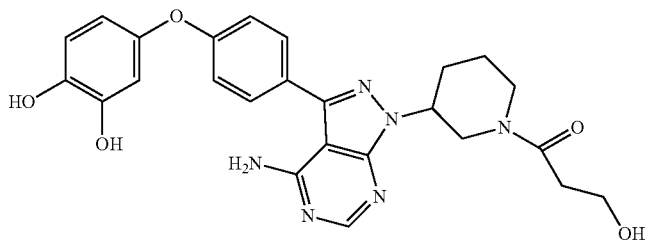

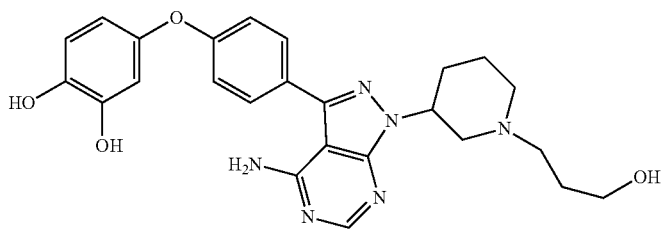

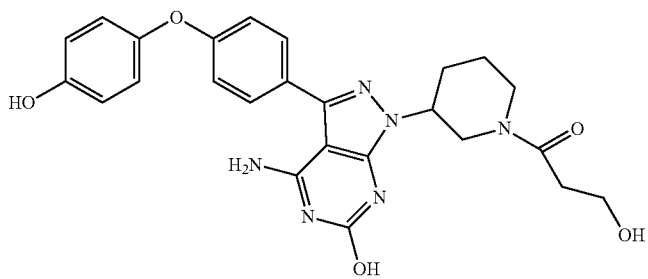

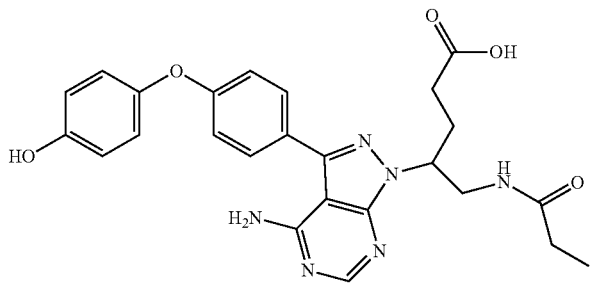

-continued
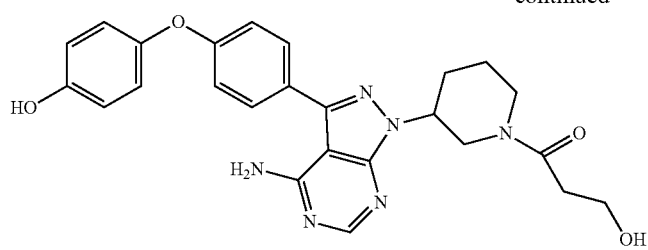
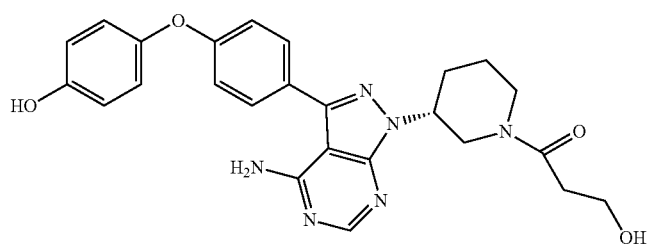
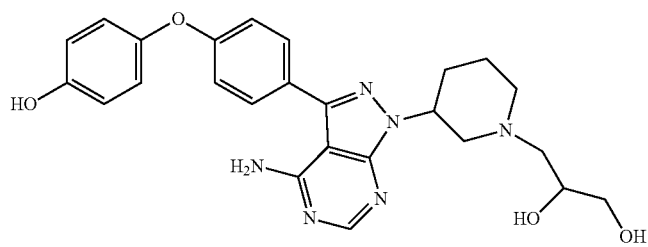
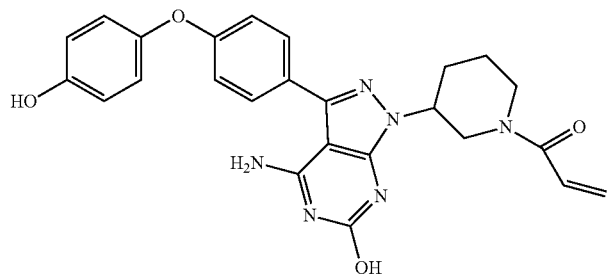
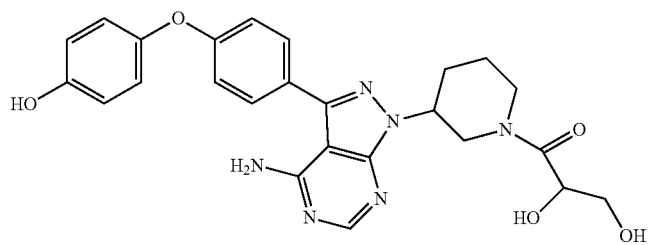
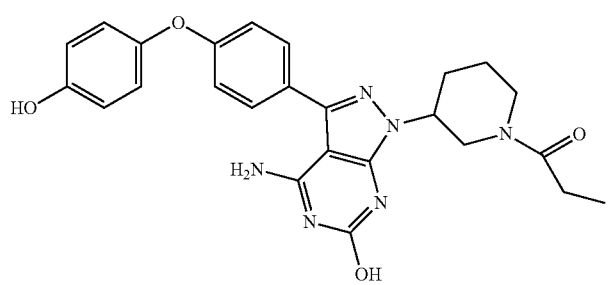

-continued
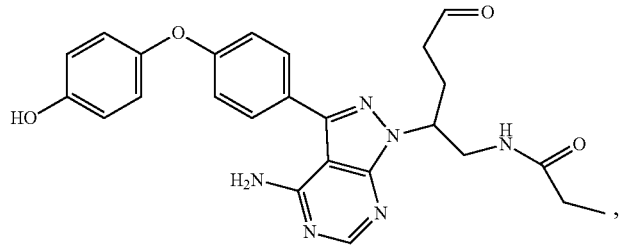
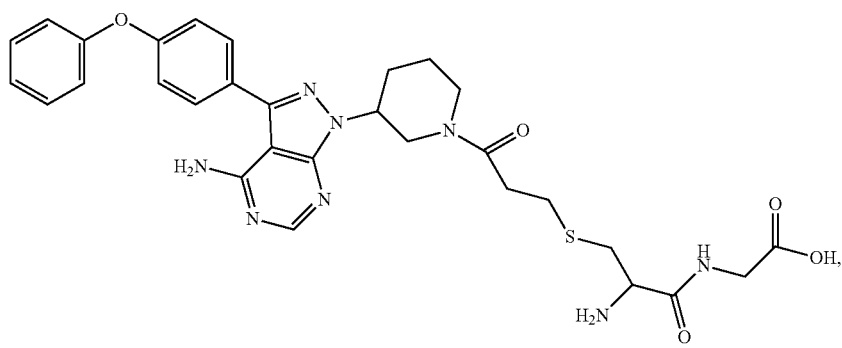
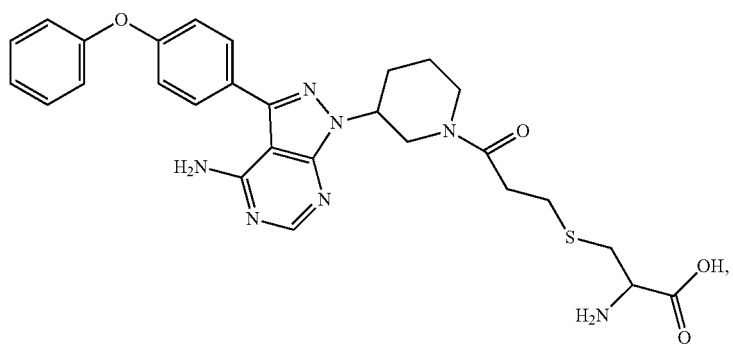
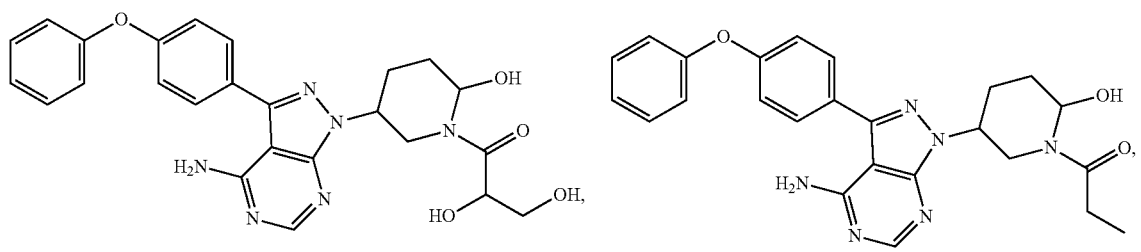
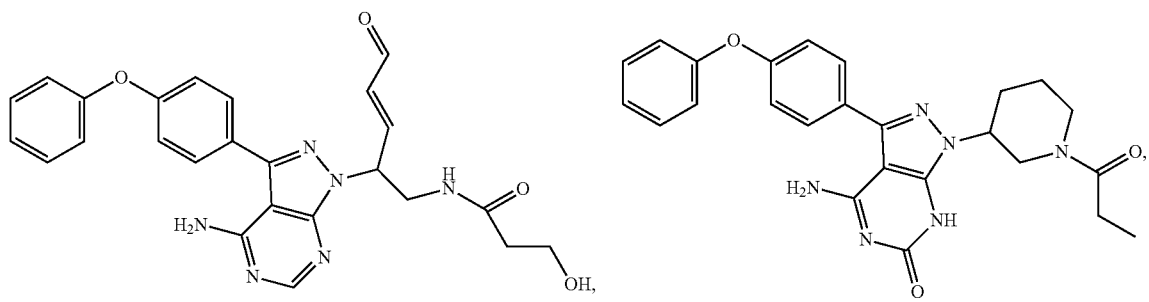

-continued

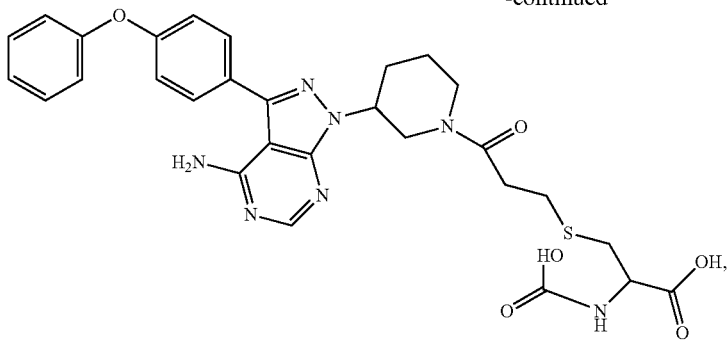

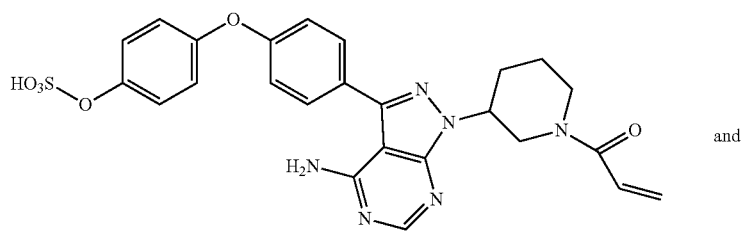

and

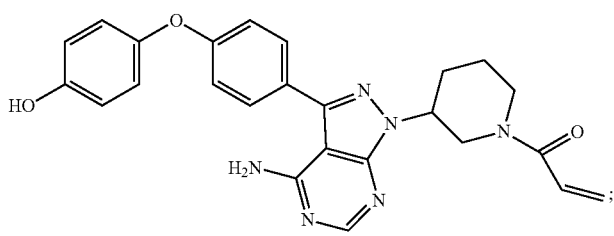

or a pharmaceutically acceptable salt, solvate, or tautomeric form thereof.

In a further embodiment is a compound of Formula (IIIA) or (IIIB) having the structure:

Formula (IIIA)

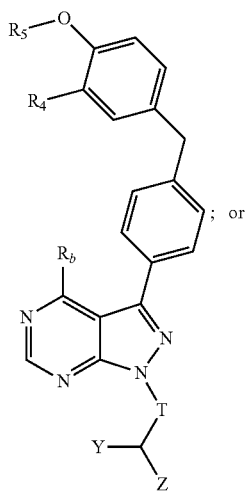

; or

Formula (IIIB)

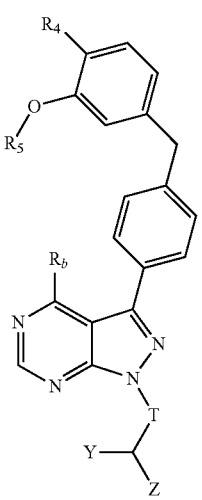

wherein $R_b$, T, Y, and Z are as described above and $R_4$ is H or OH; and $R_5$ is a glycone.

In one embodiment, the glycone is a monosaccharide. In another embodiment, the glycone is a disaccharide. In a further embodiment, the glycone is an oligosaccharide. In yet another embodiment, the glycone is glucose. In a further embodiment, the glycone is fructose. In another embodiment, the glycone is mannose. In yet a further embodiment, the glycone is glucuronic acid. In one embodiment, the glycone is attached to the oxygen atom of the compound of Formula (IIIA) or (IIIB) via an α-glycosidic bond. In another embodiment, the glycone is attached to the oxygen atom of the compound of Formula (IIIA) or (IIIB) via a β-glycosidic bond. In one embodiment, the glycone is a pyranose. In another embodiment, the glycone is a furanose.

In another embodiment is a compound of Formula (IIIC) or (IIID) having the structure:

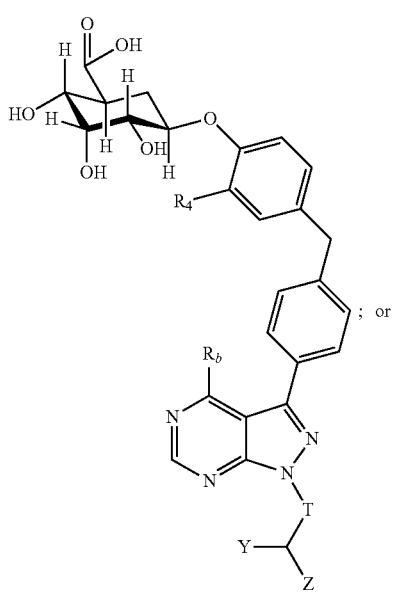

Formula (IIIC)

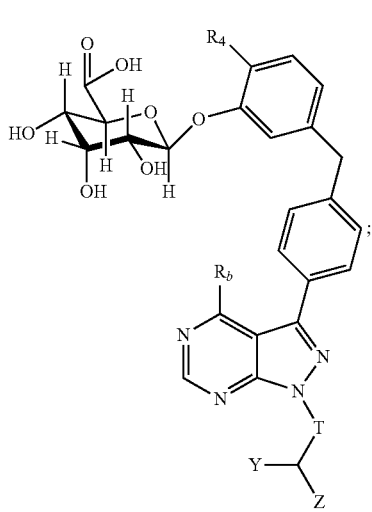

Formula (IIID)

wherein:

T is a bond, $C_1$-$C_6$alkylene, or $C_3$-$C_6$cycloalkylene;

Y and Z are each independently selected from H, $C_1$-$C_6$alkyl, $C_2$-$C_6$alkenyl, $C_3$-$C_{10}$cycloalkyl, $C_1$-$C_6$heteroalkyl, $C_2$-$C_6$heteroalkenyl, $C_4$-$C_{10}$heterocycloalkenyl and $C_2$-$C_{10}$heterocycloalkyl, wherein $C_1$-$C_6$alkyl, $C_2$-$C_6$alkenyl, $C_3$-$C_{10}$cycloalkyl, $C_1$-$C_6$heteroalkyl, $C_2$-$C_6$heteroalkenyl, $C_4$-$C_{10}$heterocycloalkenyl and $C_2$-$C_{10}$heterocycloalkyl are optionally substituted with at least one $R_1$; or Y and Z together with the carbon atom to which they are attached form a $C_3$-$C_{10}$cycloalkyl, $C_2$-$C_{10}$heterocycloalkyl, $C_4$-$C_{10}$heterocycloalkenyl, aryl, or heteroaryl, wherein $C_3$-$C_{10}$cycloalkyl, $C_2$-$C_{10}$heterocycloalkyl, $C_4$-$C_{10}$heterocycloalkenyl, aryl, or heteroaryl, are optionally substituted with at least one X;

wherein when Y and Z together with the carbon atom to which they are attached form a nitrogen atom-containing $C_2$-$C_{10}$heterocycloalkyl or $C_4$-$C_{10}$heterocycloalkenyl, the nitrogen atom of the $C_2$-$C_{10}$heterocycloalkyl or $C_4$-$C_{10}$heterocycloalkenyl is optionally substituted with W and the carbon atoms of the $C_2$-$C_{10}$heterocycloalkyl or $C_4$-$C_{10}$heterocycloalkenyl are optionally substituted with at least one X;

W is selected from J, C(=O)-J, C(=O)O-J, C(=O)NR$_2$-J, C(=NR$_2$)-J, —C(=NR$_2$)NR$_2$-J, C(=N—OR$_3$)-J, C(=S)-J, S(=O)$_v$-J, S(=O)$_v$O-J;

X is F, Cl, Br, I, —CN, —NO$_2$, —OR$_3$, —N(R$_2$)$_2$, —SR$_2$, —C$_1$-C$_6$alkyl, —C(=O)R$_2$, —OC(=O)R$_2$, —NR$_2$C(=O)R$_2$, —NR$_2$C(=O)N(R$_2$)$_2$, —C(=O)N(R$_2$)$_2$, —C(=NR$_2$)N(R$_2$)$_2$, —C(=N—OR$_2$)N(R$_2$)$_2$, —C(=S)R$_2$, —S(=O)$_v$R$_2$, —OS(=O)$_v$R$_2$, —NR$_2$C(=O)OR$_2$, —NR$_2$S(=O)$_v$R$_2$;

J is —$C_1$-$C_6$alkyl, $C_3$-$C_6$cycloalkyl, —$C_2$-$C_6$alkene, $C_2$-$C_6$heterocycloalkyl, aryl, or heteroaryl optionally substituted with at least one $R_1$;

v is 1 or 2;

R$_b$ is NH$_2$, OH, OSO$_3$H or NHSO$_3$H;

R$_1$ is selected from F, Cl, Br, I, —CN, —NO$_2$, —SR$_2$, —OR$_3$, $C_1$-$C_6$alkyl, $C_1$-$C_6$haloalkyl, $C_1$-$C_6$hydroxyalkyl, —OC$_1$-$C_6$haloalkyl, $C_1$-$C_6$heteroalkyl, $C_3$-$C_6$cycloalkyl, $C_2$-$C_6$heterocycloalkyl, phenyl, —NR$_2$S(=O)$_2$R$_2$, —S(=O)$_2$N(R$_2$)$_2$, —C(=O)CF$_3$, —C(=O)NR$_2$S(=O)$_2$R$_2$, —S(=O)$_2$NR$_2$C(=O)R$_2$, —N(R$_2$)$_2$, wherein optionally the two R$_2$ groups of N(R$_2$)$_2$ and the nitrogen atom to which they are attached form a C$_2$-C$_6$ heterocycloalkyl ring, —NR$_2$C(=O)R$_2$, —NR$_2$C(=O)N(R$_2$)$_2$, —CO$_2$R$_2$, —C(=O)R$_2$, —OC(=O)R$_2$, —C(=O)N(R$_2$)$_2$, —OS(=O)$_2$R$_2$, —OS(=O)$_2$OR$_2$, —S(=O)R$_2$, —S(=O)$_2$R$_2$, —SO$_3$H, and at least one amino acid fragment;

R$_2$ is H, $C_1$-$C_6$alkyl, $C_1$-$C_6$haloalkyl, $C_1$-$C_6$hydroxyalkyl, or $C_3$-$C_6$cycloalkyl;

R$_3$ is H, methyl, ethyl, n-propyl, iso-propyl, n-butyl, iso-butyl, tert-butyl, or SO$_3$H;

R$_4$ is H or OH; or a pharmaceutically acceptable salt, solvate, or tautomeric form thereof.

In a further embodiment is a compound of Formula (IV) having the structure:

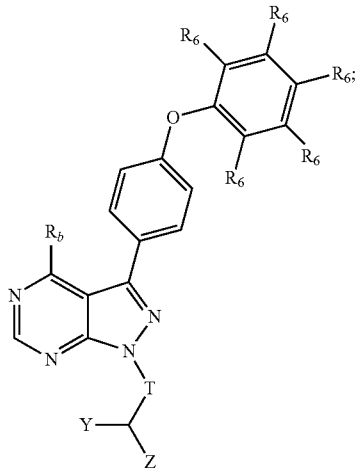

Formula (IV)

wherein:
T is a bond, $C_1$-$C_6$alkylene, or $C_3$-$C_6$cycloalkylene;
Y and Z are each independently selected from H, $C_1$-$C_6$alkyl, $C_2$-$C_6$alkenyl, $C_3$-$C_{10}$cycloalkyl, $C_1$-$C_6$heteroalkyl, $C_2$-$C_6$heteroalkenyl, $C_4$-$C_{10}$heterocycloalkenyl and $C_2$-$C_{10}$heterocycloalkyl, wherein $C_1$-$C_6$alkyl, $C_2$-$C_6$alkenyl, $C_3$-$C_{10}$cycloalkyl, $C_1$-$C_6$heteroalkyl, $C_2$-$C_6$heteroalkenyl, $C_4$-$C_{10}$heterocycloalkenyl and $C_2$-$C_{10}$heterocycloalkyl are optionally substituted with at least one $R_1$; or
Y and Z together with the carbon atom to which they are attached form a $C_3$-$C_{10}$cycloalkyl, $C_2$-$C_{10}$heterocycloalkyl, $C_4$-$C_{10}$heterocycloalkenyl, aryl, or heteroaryl, wherein $C_3$-$C_{10}$cycloalkyl, $C_2$-$C_{10}$heterocycloalkyl, $C_4$-$C_{10}$heterocycloalkenyl, aryl, or heteroaryl, are optionally substituted with at least one X;
wherein when Y and Z together with the carbon atom to which they are attached form a nitrogen atom-containing $C_2$-$C_{10}$heterocycloalkyl or $C_4$-$C_{10}$heterocycloalkenyl, the nitrogen atom of the $C_2$-$C_{10}$heterocycloalkyl or $C_4$-$C_{10}$heterocycloalkenyl is optionally substituted with W and the carbon atoms of the $C_2$-$C_{10}$heterocycloalkyl or $C_4$-$C_{10}$heterocycloalkenyl are optionally substituted with at least one X;
W is selected from J, C(=O)-J, C(=O)O-J, C(=O)NR$_2$-J, C(=NR$_2$)-J, C(=NR$_2$)NR$_2$-J, C(=N—OR$_3$)-J, C(=S)-J, S(=O)$_v$-J, S(=O)$_v$O-J;
X is F, Cl, Br, I, —CN, —NO$_2$, —OR$_3$, —N(R$_2$)$_2$, —SR$_2$, —C$_1$-C$_6$alkyl, —C(=O)R$_2$, —OC(=O)R$_2$, —NR$_2$C(=O)R$_5$, —NR$_2$C(=O)N(R$_2$)$_2$, —C(=O)N(R$_2$)$_2$, —C(=NR$_2$)N(R$_2$)$_2$, —C(=N—OR$_2$)N(R$_2$)$_2$, —C(=S)R$_2$, —S(=O)$_v$R$_2$, —OS(=O)$_v$R$_2$, —NR$_2$C(=O)OR$_2$, —NR$_2$S(=O)$_v$R$_2$;
J is —C$_1$-C$_6$alkyl, C$_3$-C$_6$cycloalkyl, —C$_2$-C$_6$alkene, C$_2$-C$_6$heterocycloalkyl, aryl, or heteroaryl optionally substituted with at least one R$_1$;
v is 1 or 2;
R$_b$ is NH$_2$, OH, OSO$_3$H or NHSO$_3$H, halogen, —CN, —NO$_2$, —SR$_2$, optionally substituted C$_1$-C$_6$alkyl; N(R$_2$)$_2$ or NHR$_7$;
R$_1$ is selected from F, Cl, Br, I, —CN, —NO$_2$, —SR$_2$, —OR$_3$, C$_1$-C$_6$alkyl, C$_1$-C$_6$haloalkyl, C$_1$-C$_6$hydroxyalkyl, —OC$_1$-C$_6$haloalkyl, C$_1$-C$_6$heteroalkyl, C$_3$-C$_6$cycloalkyl, C$_2$-C$_6$heterocycloalkyl, phenyl, —NR$_2$S(=O)$_2$R$_2$, —S(=O)$_2$N(R$_2$)$_2$, —C(=O)CF$_3$, —C(=O)NR$_2$S(=O)$_2$R$_2$, —S(=O)$_2$NR$_2$C(=O)R$_2$, —N(R$_2$)$_2$, wherein optionally the two R$_2$ groups of N(R$_2$)$_2$ and the nitrogen atom to which they are attached form a C$_2$-C$_6$ heterocycloalkyl ring, —NR$_2$C(=O)R$_2$, —NR$_2$C(=O)R$_8$, —NR$_2$C(=O)N(R$_2$)$_2$, —CO$_2$R$_2$, —C(=O)R$_2$, —OC(=O)R$_2$, —C(=O)N(R$_2$)$_2$, —OS(=O)$_2$R$_2$, —OS(=O)$_2$OR$_2$, —S(=O)R$_2$, —S(=O)$_2$R$_2$, —SO$_3$H, and at least one amino acid fragment;
R$_2$ is H, C$_1$-C$_6$alkyl, C$_1$-C$_6$haloalkyl, C$_1$-C$_6$hydroxyalkyl, or C$_3$-C$_6$cycloalkyl;
R$_3$ is H, methyl, ethyl, n-propyl, iso-propyl, n-butyl, iso-butyl, tert-butyl, or SO$_3$H;
R$_6$ is selected from H, F, Cl, Br, I, —CN, —NO$_2$, —SR$_2$, —OR$_3$, C$_1$-C$_6$alkyl, C$_1$-C$_6$haloalkyl, C$_1$-C$_6$hydroxyalkyl, —OC$_1$-C$_6$haloalkyl, C$_1$-C$_6$heteroalkyl, C$_3$-C$_6$cycloalkyl, C$_2$-C$_6$heterocycloalkyl, phenyl, —NR$_2$S(=O)$_2$R$_2$, —S(=O)$_2$N(R$_2$)$_2$, —C(=O)CF$_3$, —C(=O)NR$_2$S(=O)$_2$R$_2$, —S(=O)$_2$NR$_2$C(=O)R$_2$, —N(R$_2$)$_2$, wherein optionally the two R$_2$ groups of N(R$_2$)$_2$ and the nitrogen atom to which they are attached form a C$_2$-C$_6$ heterocycloalkyl ring, —NR$_2$C(=O)R$_2$, —NR$_2$C(=O)N(R$_2$)$_2$, —CO$_2$R$_2$, —C(=O)R$_2$, —OC(=O)R$_2$, C(=O)N(R$_2$)$_2$, —OS(=O)$_2$R$_2$, —OS(=O)$_2$OR$_2$, —S(=O)R$_2$, —S(=O)$_2$R$_2$, —SO$_3$H, and at least one amino acid fragment; wherein each R$_6$ cannot all be H;
R$_7$ is an amino protecting group;
R$_8$ is an optionally substituted C$_1$-C$_6$alkyl, an optionally substituted C$_2$-C$_6$alkenyl, an optionally substituted C$_2$-C$_6$alkynyl, or an optionally substituted C$_3$-C$_6$cycloalkyl; or a pharmaceutically acceptable salt, solvate, or metabolite thereof.

In some embodiments are provided pharmaceutically acceptable salts of compounds of Formula (I), (IA), (II), (IIIA), (IIIB), (IIIC), (IIID), or (IV) or other pyrazolopyrimidine compounds described herein. By way of example only, are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Further salts include those in which the counterion is an anion, such as adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate. Further salts include those in which the counterion is a cation, such as sodium, lithium, potassium, calcium, magnesium, ammonium, and quaternary ammonium (substituted with at least one organic moiety) cations. Also described herein are salts of a compound of Formula (I), (IA), (II), (IIIA), (IIIB), (IIIC), (IIID), or (IV) or other pyrazolopyrimidine compounds described herein having at least one sulfate group formed with a counterion, such as by way of example only, sodium, lithium, potassium, calcium, magnesium, ammonium, and quaternary ammonium cations.

In another embodiment are pharmaceutically acceptable esters of compounds of Formula (I), (IA), (II), (IIIA), (IIIB), (IIIC), (IIID), or (IV) (IIIA), (IIIB), (IIIC), or (IIID), or other pyrazolopyrimidine compounds described herein, including those in which the ester group is selected from a formate, acetate, propionate, butyrate, acrylate and ethylsuccinate.

In another embodiment are pharmaceutically acceptable carbamates of compounds of Formula (I), (IA), (II), (IIIA), (IIIB), (IIIC), (IIID), or (IV) or other pyrazolopyrimidine compounds described herein. In another embodiment are pharmaceutically acceptable N-acyl derivatives of compounds of Formula (I), (IA), (II), (IIIA), (IIIB), (IIIC), (IIID), or (IV) or other pyrazolopyrimidine compounds described herein. Examples of N-acyl groups include N-acetyl and N-ethoxycarbonyl groups.

In a further aspect are provided pharmaceutical compositions, which include a therapeutically effective amount of at least one of any of the compounds described herein, or a pharmaceutically acceptable salt, pharmaceutically acceptable tautomer, pharmaceutically acceptable prodrug, or pharmaceutically acceptable solvate. In certain embodiments, compositions provided herein further include a pharmaceutically acceptable diluent, excipient and/or binder.

Pharmaceutical compositions formulated for administration by an appropriate route and means containing effective concentrations of one or more of the compounds provided herein, or pharmaceutically effective derivatives thereof, that deliver amounts effective for the treatment, prevention, or amelioration of one or more symptoms of diseases, disorders or conditions that are modulated or otherwise affected by tyrosine kinase activity, or in which tyrosine kinase activity is implicated, are provided. The effective amounts and concentrations are effective for ameliorating any of the symptoms of any of the diseases, disorders or conditions disclosed herein.

In one aspect, provided herein are methods for treating a patient by administering a compound provided herein. In some embodiments, provided herein is a method of inhibiting the activity of tyrosine kinase(s), such as Btk, or of treating a disease, disorder, or condition, which benefit from inhibition of tyrosine kinase(s), such as Btk, in a patient, which includes administering to the patient a therapeutically effective amount of at least one of any of the compounds described herein, or pharmaceutically acceptable salt, pharmaceutically acceptable tautomer, pharmaceutically acceptable prodrug, or pharmaceutically acceptable solvate.

In another aspect, provided herein is the use of a compound disclosed herein for inhibiting Bruton's tyrosine kinase (Btk) activity or for the treatment of a disease, disorder, or condition, which benefit from inhibition of Bruton's tyrosine kinase (Btk) activity.

In some embodiments, compounds provided herein are administered to a human. In some embodiments, compounds provided herein are orally administered. In other embodiments, the pharmaceutical formulation that is formulated for a route of administration is selected from oral administration, parenteral administration, buccal administration, nasal administration, topical administration, or rectal administration.

In other embodiments, compounds provided herein are used for the formulation of a medicament for the inhibition of tyrosine kinase activity. In some other embodiments, compounds provided herein are used for the formulation of a medicament for the inhibition of Bruton's tyrosine kinase (Btk) activity.

Articles of manufacture including packaging material, a compound or composition or pharmaceutically acceptable derivative thereof provided herein, which is effective for inhibiting the activity of tyrosine kinase(s), such as Btk, within the packaging material, and a label that indicates that the compound or composition, or pharmaceutically acceptable salt, pharmaceutically acceptable tautomer, pharmaceutically acceptable prodrug, or pharmaceutically acceptable solvate thereof, is used for inhibiting the activity of tyrosine kinase(s), such as Btk, are provided.

In a further aspect, provided herein is a method for treating an autoimmune disease by administering to a subject in need thereof a composition containing a therapeutically effective amount of at least one compound having the structure of Formula (I), (IA), (II), (IIIA), (IIIB), (IIIC), (IIID), or (IV) or other pyrazolopyrimidine compounds described herein. In one embodiment, the autoimmune disease is arthritis. In another embodiment, the autoimmune disease is lupus. In some embodiments, the autoimmune disease is inflammatory bowel disease (including Crohn's disease and ulcerative colitis), rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease, Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, or vulvodynia.

In a further aspect, provided herein is a method for treating a heteroimmune condition or disease by administering to a subject in need thereof a composition containing a therapeutically effective amount of at least one compound having the structure of Formula (I), (IA), (II), (IIIA), (IIIB), (IIIC), (IIID), or (IV) or other pyrazolopyrimidine compounds described herein. In some embodiments, the heteroimmune condition or disease is graft versus host disease, transplantation, transfusion, anaphylaxis, allergy, type I hypersensitivity, allergic conjunctivitis, allergic rhinitis, or atopic dermatitis.

In a further aspect, provided herein is a method for treating an inflammatory disease by administering to a subject in need thereof a composition containing a therapeutically effective amount of at least one compound having the structure of Formula (I), (IA), (II), (IIIA), (IIIB), (IIIC), (IIID), or (IV) or other pyrazolopyrimidine compounds described herein. In some embodiments, the inflammatory disease is asthma, inflammatory bowel disease (including Crohn's disease and ulcerative colitis), appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, or vulvitis.

In yet another aspect, provided herein is a method for treating a cancer by administering to a subject in need thereof a composition containing a therapeutically effective amount of at least one compound having the structure of Formula (I), (IA), (II), (IIIA), (IIIB), (IIIC), (IIID), or (IV) or other pyrazolopyrimidine compounds described herein. In one embodiment, the cancer is a B-cell proliferative disorder, e.g., diffuse large B cell lymphoma, follicular lymphoma, chronic lymphocytic lymphoma, chronic lymphocytic leukemia, B-cell prolymphocytic leukemia, lymphoplasmacytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt's lymphoma/leukemia, or lymphomatoid granulomatosis. In some embodiments, where the subject is suffering from a cancer, an anti-cancer agent is administered to the subject in addition to one of the above-mentioned compounds. In one embodiment, the anti-cancer agent is an inhibitor of mitogen-activated protein kinase signaling, e.g., U0126, PD98059, PD184352, PD0325901, ARRY-142886, SB239063, SP600125, BAY 43-9006, wortmannin, or LY294002.

In another aspect, provided herein is a method for treating a thromboembolic disorder by administering to a subject in need thereof a composition containing a therapeutically effective amount of at least one compound having the structure of Formula (I), (IA), (II), (IIIA), (IIIB), (IIIC), (IIID), or (IV) or other pyrazolopyrimidine compounds described herein. In some embodiments, the thromboembolic disorder is myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, or deep venous thrombosis.

In another aspect, provided herein is a method for treating a mastocytosis by administering to a subject in need thereof a composition containing a therapeutically effective amount of at least one compound having the structure of Formula (I), (IA), (II), (IIIA), (IIIB), (IIIC), (IIID), or (IV) or other pyrazolopyrimidine compounds described herein.

In yet another aspect, provided herein is a method for treating a osteoporosis or bone resorption disorders by administering to a subject in need thereof a composition containing a therapeutically effective amount of at least one compound having the structure of Formula (I), (IA), (II), (IIIA), (IIIB), (IIIC), (IIID), or (IV) or other pyrazolopyrimidine compounds described herein.

In further embodiments, the compound irreversibly inhibits the Bruton's tyrosine kinase.

Also described herein are kinase inhibitors that selectively bind to a protein tyrosine kinase selected from Btk, a Btk homolog, and a Btk kinase cysteine homolog, in which the kinase inhibitor reversibly and non-selectively binds to a multiplicity of protein tyrosine kinases. In one embodiment the plasma half life of the kinase inhibitor is less than about 4 hours. In another embodiment the plasma half life of the kinase inhibitor is less than about 3 hours.

In a further embodiment are kinase inhibitors that selectively bind to at least one of Btk, Jak3, Blk, Bmx, Tec, and Itk. In another embodiment are kinase inhibitors that selectively bind to Btk. In another embodiment are kinase inhibitors that selectively and irreversibly bind to Jak3. In another embodiment are kinase inhibitors that selectively bind to Tec. In another embodiment are kinase inhibitors that selectively bind to Itk. In another embodiment are kinase inhibitors that selectively bind to Btk and Tec. In another embodiment are kinase inhibitors that selectively bind to Blk. In yet a further embodiment are kinase inhibitors that reversibly and non-selectively bind to a multiplicity of src-family protein kinase inhibitors.

Also described herein are inhibitors that are identified using such methods, assays and systems. In some embodiments, the inhibitor is a selective inhibitor, including selectivity for a particular Btk kinase cysteine homolog over other Btk kinase cysteine homologs.

Further described herein are pharmaceutical formulations comprising the kinase inhibitors of any kinase inhibitor compound previously listed. In one embodiment the pharmaceutical formulation includes a pharmaceutical acceptable excipient. In some embodiments, pharmaceutical formulations provided herein are administered to a human. In some embodiments, the selective kinase inhibitors provided herein are orally administered. In other embodiments, the selective kinase inhibitors provided herein are used for the formulation of a medicament for the inhibition of tyrosine kinase activity. In some other embodiments, the selective kinase inhibitors provided herein are used for the formulation of a medicament for the inhibition of a kinase activity, including a tyrosine kinase activity, including a Btk activity, including a Btk homolog activity, including a Btk kinase cysteine homolog activity.

In any of the aforementioned aspects are further embodiments in which administration is enteral, parenteral, or both, and wherein (a) the effective amount of the compound is systemically administered to the mammal; (b) the effective amount of the compound is administered orally to the mammal; (c) the effective amount of the compound is intravenously administered to the mammal; (d) the effective amount of the compound administered by inhalation; (e) the effective amount of the compound is administered by nasal administration; or (f) the effective amount of the compound is administered by injection to the mammal; (g) the effective amount of the compound is administered topically (dermal) to the mammal; (h) the effective amount of the compound is administered by ophthalmic administration; or (i) the effective amount of the compound is administered rectally to the mammal In further embodiments the pharmaceutical formulation is formulated for a route of administration selected from oral administration, parenteral administration, buccal administration, nasal administration, topical administration, or rectal administration.

In any of the aforementioned aspects are further embodiments comprising single administrations of the effective amount of the pharmaceutical formulation, including further embodiments in which (i) the pharmaceutical formulations is administered once; (ii) the pharmaceutical formulations is administered to the mammal once a day; (iii) the pharmaceutical formulations is administered to the mammal multiple times over the span of one day; (iv) continually; or (v) continuously.

In any of the aforementioned aspects are further embodiments comprising multiple administrations of the effective amount of the pharmaceutical formulations, including further embodiments in which (i) the pharmaceutical formulations is administered in a single dose; (ii) the time between multiple administrations is every 6 hours; (iii) the pharmaceutical formulations is administered to the mammal every 8 hours. In further or alternative embodiments, the method comprises a drug holiday, wherein the administration of the pharmaceutical formulations is temporarily suspended or the dose of the pharmaceutical formulations being administered is temporarily reduced; at the end of the drug holiday, dosing of the pharmaceutical formulations is resumed. The length of the drug holiday varies from 2 days to 1 year.

In some aspects described herein the inhibitor is selective for one kinase selected from Btk, a Btk homolog, and a Btk kinase cysteine homolog over at least one other kinase selected from Btk, a Btk homolog, and a Btk kinase cysteine homolog. In other aspects described herein the inhibitor is selective for at least one kinase selected from Btk, a Btk homolog, and a Btk kinase cysteine homolog over at least one other non-kinase molecule having an accessible SH group.

In certain embodiments, provided herein is a pharmaceutical composition containing: i) a physiologically acceptable carrier, diluent, and/or excipient; and ii) one or more compounds provided herein.

Other objects, features and advantages of the methods and compositions described herein will become apparent from the following detailed description. It should be understood, however, that the detailed description and the specific examples, while indicating specific embodiments, are given by way of illustration only. The section headings used herein are for organizational purposes only and are not to be construed as limiting the subject matter described.

Certain Terminology

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Definition of standard chemistry terms are found in reference works, including Carey and Sundberg "ADVANCED ORGANIC CHEMISTRY $4^{TH}$ ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques are optionally used for chemical syntheses, chemical analyses, pharmaceutical preparation, formulation, and delivery, and treatment of patients. Standard techniques are optionally used for recombinant DNA, oligonucleotide synthesis, and tissue culture and transformation (e.g., electroporation, lipofection). Reactions and purification techniques are performed using documented methodologies or as described herein.

It is to be understood that the methods and compositions described herein are not limited to the particular methodology, protocols, cell lines, constructs, and reagents described herein and as such optionally vary. It is also to be understood that the terminology used herein is for the purpose of describing particular embodiments only, and is not intended to limit the scope of the methods and compositions described herein, which will be limited only by the appended claims.

Unless stated otherwise, the terms used for complex moieties (i.e., multiple chains of moieties) are to be read equivalently either from left to right or right to left. For example, the group alkylenecycloalkylene refers both to an alkylene group followed by a cycloalkylene group or as a cycloalkylene group followed by an alkylene group.

The suffix "ene" appended to a group indicates that such a group is a diradical. By way of example only, a methylene is a diradical of a methyl group, that is, it is a —CH$_2$— group; and an ethylene is a diradical of an ethyl group, i.e., —CH$_2$CH$_2$—.

An "alkyl" group refers to an aliphatic hydrocarbon group. The alkyl moiety includes a "saturated alkyl" group, which means that it does not contain any alkene or alkyne moieties. The alkyl moiety also includes an "unsaturated alkyl" moiety, which means that it contains at least one alkene or alkyne moiety. An "alkene" moiety refers to a group that has at least one carbon-carbon double bond, and an "alkyne" moiety refers to a group that has at least one carbon-carbon triple bond. The alkyl moiety, whether saturated or unsaturated, includes branched, straight chain, or cyclic moieties. Depending on the structure, an alkyl group includes a monoradical or a diradical (i.e., an alkylene group), and if a "lower alkyl" having 1 to 6 carbon atoms.

As used herein, $C_1$-$C_x$ includes $C_1$-$C_2$, $C_1$-$C_3$ ... $C_1$-$C_x$.

The "alkyl" moiety optionally has 1 to 10 carbon atoms (whenever it appears herein, a numerical range such as "1 to 10" refers to each integer in the given range; e.g., "1 to 10 carbon atoms" means that the alkyl group is selected from a moiety having 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from among methyl, ethyl, propyl, iso-propyl, n-butyl, iso-butyl, sec-butyl, and t-butyl. Thus $C_1$-$C_4$ alkyl includes $C_1$-$C_2$ alkyl and $C_1$-$C_3$ alkyl. Alkyl groups are optionally substituted or unsubstituted. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like.

The term "alkenyl" refers to a type of alkyl group in which the first two atoms of the alkyl group form a double bond that is not part of an aromatic group. That is, an alkenyl group begins with the atoms —C(R)=C(R)—R, wherein R refers to the remaining portions of the alkenyl group, which are either the same or different. The alkenyl moiety is optionally branched, straight chain, or cyclic (in which case, it is also known as a "cycloalkenyl" group). Depending on the structure, an alkenyl group includes a monoradical or a diradical (i.e., an alkenylene group). Alkenyl groups are optionally substituted. Non-limiting examples of an alkenyl group include —CH=CH$_2$, —C(CH$_3$)=CH$_2$, —CH=CHCH$_3$, —C(CH$_3$)=CHCH$_3$. Alkenylene groups include, but are not limited to, —CH=CH—, —C(CH$_3$)=CH—, —CH=CHCH$_2$—, —CH=CHCH$_2$CH$_2$— and —C(CH$_3$)=CHCH$_2$—. Alkenyl groups optionally have 2 to 10 carbons, and if a "lower alkenyl" having 2 to 6 carbon atoms.

The term "alkynyl" refers to a type of alkyl group in which the first two atoms of the alkyl group form a triple bond. That is, an alkynyl group begins with the atoms —C≡C—R, wherein R refers to the remaining portions of the alkynyl group, which is either the same or different. The "R" portion of the alkynyl moiety may be branched, straight chain, or cyclic. Depending on the structure, an alkynyl group includes a monoradical or a diradical (i.e., an alkynylene group). Alkynyl groups are optionally substituted. Non-limiting examples of an alkynyl group include, but are not limited to, —C≡CH, —C≡CCH$_3$, —C≡CCH$_2$CH$_3$, —C≡C—, and —C≡CCH$_2$—. Alkynyl groups optionally have 2 to 10 carbons, and if a "lower alkynyl" having 2 to 6 carbon atoms.

An "alkoxy" group refers to a (alkyl)O— group, where alkyl is as defined herein.

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl.

"Alkoxyalkyl" refers to an alkyl radical, as defined herein, substituted with an alkoxy group, as defined herein.

The term "alkylamine" refers to the —N(alkyl)$_x$H$_y$ group, where x and y are selected from among x=1, y=1 and x=2, y=0. When x=2, the alkyl groups, taken together with the N atom to which they are attached, can optionally form a cyclic ring system.

"Alkylaminoalkyl" refers to an alkyl radical, as defined herein, substituted with an alkylamine, as defined herein.

"Hydroxyalkylaminoalkyl" refers to an alkyl radical, as defined herein, substituted with an alkylamine, and alkylhydroxy, as defined herein.

"Alkoxyalkylaminoalkyl" refers to an alkyl radical, as defined herein, substituted with an alkylamine and substituted with an alkylalkoxy, as defined herein.

An "amide" is a chemical moiety with the formula —C(O)NHR or —NHC(O)R, where R is selected from among alkyl, cycloalkyl, aryl, heteroaryl (bonded through a ring carbon) and heteroalicyclic (bonded through a ring carbon). In some embodiments, an amide moiety forms a linkage between an amino acid or a peptide molecule and a compound described herein, thereby forming a prodrug. Any amine, or carboxyl side chain on the compounds described herein can be amidified. The procedures and specific groups to make such amides are found in sources such as Greene and Wuts, Protective Groups in Organic Synthesis, 3$^{rd}$ Ed., John Wiley & Sons, New York, N.Y., 1999, which is incorporated herein by reference for this disclosure.

The term "amino acid fragment" refers to a portion of an amino acid, such as by way of example only, the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), or a dipeptide, tripeptide or other polypeptide comprising a combination of the 20 common amino acids or a non-natural amino acid. In some embodiments, the amino acid fragment is attached to the compound of Formula (I), (IA), (II), (IIIA), (IIIB), (IIIC), (IIID), or (IV) or other pyrazolopyrimidine compounds described herein via the side chain of the amino acid. In one embodiment, the amino acid fragment is a cysteine fragment wherein the remaining portion of the compound of Formula (II) is bound via a sulfur bond. In another embodiment, the remaining portion of a compound of Formula (II) is bound via a sulfur bond of a glutathione fragment. In another embodiment, the amino acid fragments are derived from beta-amino acids. In further embodiments, the amino acid fragments are derived from portions of polypeptides or proteins. In yet further embodiments, the amino acid fragment is attached to the compound of Formula (I), (IA), (II), (IIIA), (IIIB), (IIIC), (IIID), or (IV) or other pyrazolopyrimidine compounds described herein via the N-terminal or the acyl-terminal of the amino acid.

The term "ester" refers to a chemical moiety with formula —COOR, where R is selected from among alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are found in sources such as Greene and Wuts, Protective Groups in Organic Synthesis, 3$^{rd}$ Ed., John Wiley & Sons, New York, N.Y., 1999, which is incorporated herein by reference for this disclosure.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

The term "carbocyclic" or "carbocycle" refers to a ring wherein each of the atoms forming the ring is a carbon atom. Carbocycle includes aryl and cycloalkyl. The term thus distinguishes carbocycle from heterocycle ("heterocyclic") in which the ring backbone contains at least one atom which is different from carbon (i.e a heteroatom). Heterocycle includes heteroaryl and heterocycloalkyl. Carbocycles and heterocycles can be optionally substituted.

The term "aromatic" refers to a planar ring having a delocalized π-electron system containing 4n+2π electrons, where n is an integer. Aromatic rings can be formed from five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

An "aryloxy" group refers to an (aryl)O— group, where aryl is as defined herein.

The term "carbonyl" as used herein refers to a group containing a moiety selected from the group consisting of —C(O)—, —S(O)—, —S(O)2-, and —C(S)—, including, but not limited to, groups containing a least one ketone group, and/or at least one aldehyde group, and/or at least one ester group, and/or at least one carboxylic acid group, and/or at least one thioester group. Such carbonyl groups include ketones, aldehydes, carboxylic acids, esters, and thioesters. In some embodiments, such groups are a part of linear, branched, or cyclic molecules.

The term "cycloalkyl" refers to a monocyclic or polycyclic radical that contains only carbon and hydrogen, and is optionally saturated, partially unsaturated, or fully unsaturated. Cycloalkyl groups include groups having from 3 to 10 ring atoms. Illustrative examples of cycloalkyl groups include the following moieties:

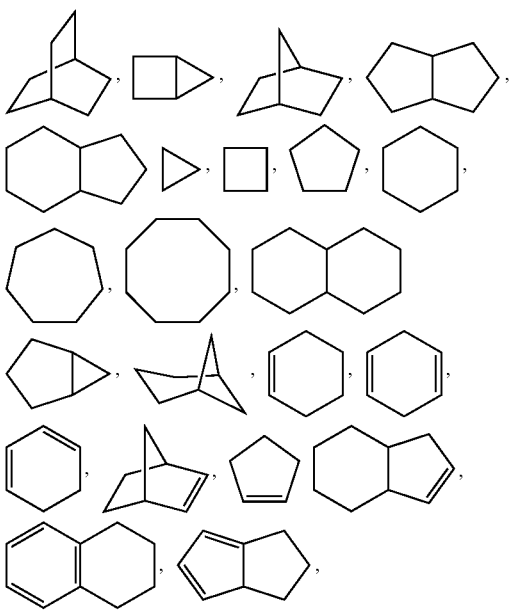

and the like. Depending on the structure, a cycloalkyl group is either a monoradical or a diradical (e.g., an cycloalkylene group), and if a "lower cycloalkyl" having 3 to 8 carbon atoms.

"Cycloalkylalkyl" means an alkyl radical, as defined herein, substituted with a cycloalkyl group. Non-limiting cycloalkylalkyl groups include cyclopropylmethyl, cyclobutylmethyl, cyclopentylmethyl, cyclohexylmethyl, and the like.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocyclic ring can have additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In heterocycles that have two or more heteroatoms, those two or more heteroatoms can be the same or different from one another. Heterocycles can be optionally substituted. Binding to a heterocycle can be at a heteroatom or via a carbon atom. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, are optionally C-attached or N-attached where such is possible. For instance, a group derived from pyrrole includes pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

The terms "heteroaryl" or, alternatively, "heteroaromatic" refers to an aromatic group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. Illustrative examples of heteroaryl groups include the following moieties:

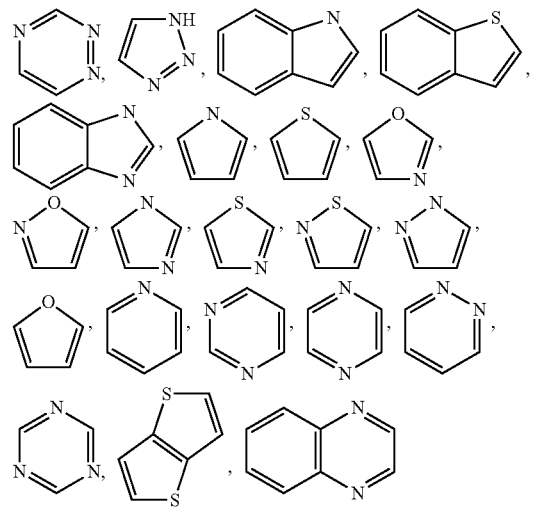

and the like. Depending on the structure, a heteroaryl group can be a monoradical or a diradical (i.e., a heteroarylene group).

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl"

group refers to a cycloalkyl group that includes at least one heteroatom selected from nitrogen, oxygen and sulfur. In some embodiments, the radicals are fused with an aryl or heteroaryl. Heterocycloalkyl rings can be formed by three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

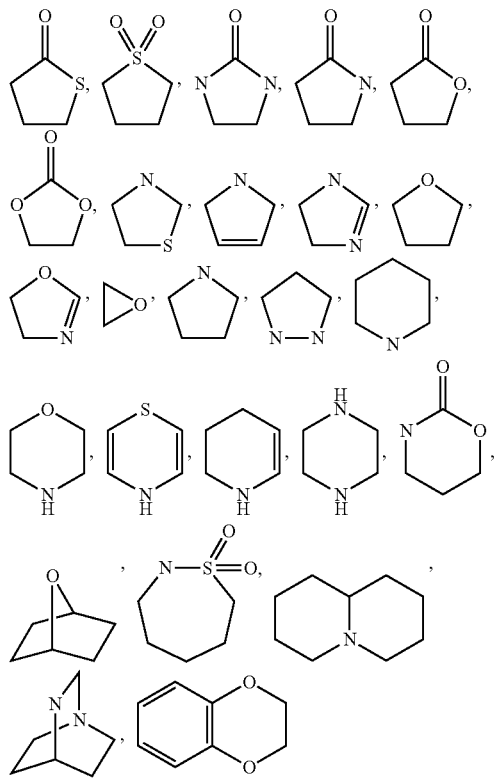

and the like. The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group).

The term "halo" or, alternatively, "halogen" or "halide" means fluoro, chloro, bromo and iodo.

The term "haloalkyl," refers to alkyl structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another.

The term "fluoroalkyl," as used herein, refers to alkyl group in which at least one hydrogen is replaced with a fluorine atom. Examples of fluoroalkyl groups include, but are not limited to, —CF$_3$, —CH$_2$CF$_3$, —CF$_2$CF$_3$, —CH$_2$CH$_2$CF$_3$ and the like.

As used herein, the term "heteroalkyl" refers to optionally substituted alkyl radicals in which one or more skeletal chain atoms is a heteroatom, e.g., oxygen, nitrogen, sulfur, silicon, phosphorus or combinations thereof. The heteroatom(s) are placed at any interior position of the heteroalkyl group or at the position at which the heteroalkyl group is attached to the remainder of the molecule. Examples include, but are not limited to, —CH$_2$—O—CH$_3$, —CH$_2$—CH$_2$—O—CH$_3$, —CH$_2$—NH—CH$_3$, —CH$_2$—CH$_2$—NH—CH$_3$, —CH$_2$—N(CH$_3$)—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S((O))—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. In addition, in some embodiments, up to two heteroatoms are consecutive, such as, by way of example, —CH$_2$—NH—OCH$_3$ and —CH$_2$—O—Si(CH$_3$)$_3$.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "bond" or "single bond" refers to a chemical bond between two atoms, or two moieties when the atoms joined by the bond are considered to be part of larger substructure.

The term "moiety" refers to a specific segment or functional group of a molecule. Chemical moieties are often recognized chemical entities embedded in or appended to a molecule.

A "thioalkoxy" or "alkylthio" group refers to a —S-alkyl group.

A "SH" group is also referred to either as a thiol group or a sulfhydryl group.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, acyl, nitro, haloalkyl, fluoroalkyl, amino, including mono- and di-substituted amino groups, and the protected derivatives thereof. By way of example an optional substituents may be L$_s$R$_s$, wherein each L$_s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, -(substituted or unsubstituted C$_1$-C$_6$ alkyl), or -(substituted or unsubstituted C$_2$-C$_6$ alkenyl); and each R$_s$ is independently selected from H, (substituted or unsubstituted C$_1$-C$_4$alkyl), (substituted or unsubstituted C$_3$-C$_6$cycloalkyl), heteroaryl, or heteroalkyl. The protecting groups that forms the protective derivatives of the above substituents include those found in sources such as Greene and Wuts, above.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, the term "agonist" refers to a compound, the presence of which results in a biological activity of a protein that is the same as the biological activity resulting from the presence of a naturally occurring ligand for the protein, such as, for example, Btk.

As used herein, the term "partial agonist" refers to a compound the presence of which results in a biological activity of a protein that is of the same type as that resulting from the presence of a naturally occurring ligand for the protein, but of a lower magnitude.

As used herein, the term "antagonist" refers to a compound, the presence of which results in a decrease in the magnitude of a biological activity of a protein. In certain embodiments, the presence of an antagonist results in complete inhibition of a biological activity of a protein, such as, for example, Btk. In certain embodiments, an antagonist is an inhibitor.

As used herein, "amelioration" of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of the weight of compounds disclosed herein, such as, compounds of Formula (I), (IA), (II), (IIIA), (IIIB), (IIIC), (IIID), or (IV) or other pyrazolopyrimidine compounds described herein, dosed that is delivered into the general circulation of the animal or human being studied. The total exposure ($AUC_{(0-\infty)}$) of a drug when administered intravenously is usually defined as 100% bioavailable (F %). "Oral bioavailability" refers to the extent to which compounds disclosed herein, such as, compounds of Formula (I), (IA), (II), (IIIA), (IIIB), (IIIC), (IIID), or (IV) or other pyrazolopyrimidine compounds described herein, are absorbed into the general circulation when the pharmaceutical composition is taken orally as compared to intravenous injection.

"Blood plasma concentration" refers to the concentration of compounds disclosed herein, such as, compounds of Formula (I), (IA), (II), (IIIA), (IIIB), (IIIC), (IIID), or (IV) or other pyrazolopyrimidine compounds described herein, in the plasma component of blood of a subject. It is understood that the plasma concentration of compounds of Formula (I), (IA), (II), (IIIA), (IIIB), (IIIC), (IIID), or (IV) or other pyrazolopyrimidine compounds described herein, may vary significantly between subjects, due to variability with respect to metabolism and/or possible interactions with other therapeutic agents. In accordance with one embodiment disclosed herein, the blood plasma concentration of the compounds of Formula (I), (IA), (II), (IIIA), (IIIB), (IIIC), (IIID), or (IV) or other pyrazolopyrimidine compounds described herein, does vary from subject to subject. Likewise, values such as maximum plasma concentration ($C_{max}$) or time to reach maximum plasma concentration (T.), or total area under the plasma concentration time curve ($AUC_{(0-\infty)}$) may vary from subject to subject. Due to this variability, the amount necessary to constitute "a therapeutically effective amount" of a compound of Formula (I), (IA), (II), (IIIA), (IIIB), (IIIC), (IIID), or (IV) or other pyrazolopyrimidine compounds described herein, is expected to vary from subject to subject.

The term "Bruton's tyrosine kinase," as used herein, refers to Bruton's tyrosine kinase from Homo sapiens, as disclosed in, e.g., U.S. Pat. No. 6,326,469 (GenBank Accession No. NP_000052).

The term "Bruton's tyrosine kinase homolog," as used herein, refers to orthologs of Bruton's tyrosine kinase, e.g., the orthologs from mouse (GenBank Accession No. AAB47246), dog (GenBank Accession No. XP_549139.), rat (GenBank Accession No. NP_001007799), chicken (GenBank Accession No. NP_989564), or zebra fish (GenBank Accession No. XP_698117), and fusion proteins of any of the foregoing that exhibit kinase activity towards one or more substrates of Bruton's tyrosine kinase (e.g. a peptide substrate having the amino acid sequence "AVLESEEELYS-SARQ").

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case is optionally determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the of Formula (I), (IA), (II), (IIIA), (IIIB), (IIIC), (IIID), or (IV) or other pyrazolopyrimidine compounds described herein, age, weight, general condition of the subject, the condition being treated, the severity of the condition being treated, and the judgment of the prescribing physician.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

The term "homologous cysteine," as used herein refers to a cysteine residue found with in a sequence position that is homologous to that of cysteine 481 of Bruton's tyrosine kinase, as defined herein. For example, cysteine 482 is the homologous cysteine of the rat ortholog of Bruton's tyrosine kinase; cysteine 479 is the homologous cysteine of the chicken ortholog; and cysteine 481 is the homologous cysteine in the zebra fish ortholog. In another example, the homologous cysteine of TXK, a Tec kinase family member related to Bruton's tyrosine, is Cys 350. See also the sequence alignments of tyrosine kinases (TK) published on the world wide web at kinase.com/human/kinome/phylogeny.html.

The term "identical," as used herein, refers to two or more sequences or subsequences which are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences are "substantially identical" if the sequential units are about 60% identical, about 65% identical, about 70% identical, about 75% identical, about 80% identical, about 85% identical, about 90% identical, or about 95% identical over a specified region. Such percentages to describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75-100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75-100 nucleic acids in length, over a region that is about 50 nucleic acids in length, or, where not specified, across the entire sequence of a polynucleotide sequence.

The terms "inhibits", "inhibiting", or "inhibitor" of a kinase, as used herein, refer to inhibition of enzymatic phosphotransferase activity.

The term "isolated," as used herein, refers to separating and removing a component of interest from at least some portion of components not of interest. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production. Also, by way of example, a gene is isolated when separated from open reading frames which flank the gene and encode a protein other than the gene of interest.

The term "irreversible inhibitor," as used herein, refers to a compound that, upon contact with a target protein (e.g., a kinase) causes the formation of a new covalent bond with or within the protein, whereby one or more of the target protein's biological activities (e.g., phosphotransferase activity) is diminished or abolished notwithstanding the subsequent presence or absence of the irreversible inhibitor.

The term "irreversible Btk inhibitor," as used herein, refers to an inhibitor of Btk that in some embodiments forms a covalent bond with an amino acid residue of Btk. In one embodiment, the irreversible inhibitor of Btk forms a covalent bond with a Cys residue of Btk; in particular embodiments, the irreversible inhibitor forms a covalent bond with a Cys 481 residue (or a homolog thereof) of Btk or a cysteine residue in the homologous corresponding position of another tyrosine kinase.

The term "linkage," as used herein to refer to bonds or a chemical moiety formed from a chemical reaction between the functional group of a linker and another molecule. In some embodiments, such bonds include, but are not limited to, covalent linkages and non-covalent bonds, while such chemical moieties include, but are not limited to, esters, carbonates, imines, phosphate esters, hydrazones, acetals, orthoesters, peptide linkages, and oligonucleotide linkages. Hydrolytically stable linkages means that the linkages are substantially stable in water and do not react with water at useful pH values, including but not limited to, under physiological conditions for an extended period of time, perhaps even indefinitely. Hydrolytically unstable or degradable linkages means that the linkages are degradable in water or in aqueous solutions, including for example, blood. In other embodiments, enzymatically unstable or degradable linkages means that the linkage is degraded by one or more enzymes. By way of example only, PEG and related polymers include degradable linkages in the polymer backbone or in the linker group between the polymer backbone and one or more of the terminal functional groups of the polymer molecule. Such degradable linkages include, but are not limited to, ester linkages formed by the reaction of PEG carboxylic acids or activated PEG carboxylic acids with alcohol groups on a biologically active agent, wherein such ester groups generally hydrolyze under physiological conditions to release the biologically active agent. Other hydrolytically degradable linkages include but are not limited to carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The term "Michael acceptor moiety" refers to a functional group that can participate in a Michael reaction, wherein a new covalent bond is formed between a portion of the Michael acceptor moiety and the donor moiety. The Michael acceptor moiety is an electrophile and the "donor moiety" is a nucleophile. The double bond groups presented in any of Formula (I) or (IA) are non-limiting examples of Michael acceptor moieties.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "nanoparticle," as used herein, refers to a particle which has a particle size between about 500 nm to about 1 nm.

As used herein, the term "pERK" refers to phosphorylated ERK1 and ERK2 at Thr202/Tyr 204 as detected by commercially available phospho-specific antibodies (e.g. Cell Signaling Technologies #4377).

The term "plasma half life," as used herein refers to half-life in rat, dog or human as determined by measure drug concentration over time in plasma following a single dose and fitting data to standard pharmacokinetic models using software such as WinNonLin to determine the time at which drug has been 50% eliminated from plasma.

The term "prophylactically effective amount," as used herein, refers that amount of a composition applied to a patient which will relieve to some extent one or more of the symptoms of a disease, condition or disorder being treated. In such prophylactic applications, such amounts may depend on the patient's state of health, weight, and the like.

As used herein, the term "selective binding compound" refers to a compound that selectively binds to any portion of one or more target proteins.

As used herein, the term "selectively binds" refers to the ability of a selective binding compound to bind to a target protein, such as, for example, Btk, with greater affinity than it binds to a non-target protein. In certain embodiments, specific binding refers to binding to a target with an affinity that is at least 10, 50, 100, 250, 500, 1000 or more times greater than the affinity for a non-target.

As used herein, the term "selective modulator" refers to a compound that selectively modulates a target activity relative to a non-target activity. In certain embodiments, specific modulator refers to modulating a target activity at least 10, 50, 100, 250, 500, 1000 times more than a non-target activity.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater.

The term "subject" as used herein, refers to an animal which is the object of treatment, observation or experiment. By way of example only, a subject may be, but is not limited to, a mammal including, but not limited to, a human.

As used herein, the term "target activity" refers to a biological activity capable of being modulated by a selective modulator. Certain exemplary target activities include, but are not limited to, binding affinity, signal transduction, enzymatic activity, tumor growth, inflammation or inflammation-related processes, and amelioration of one or more symptoms associated with a disease or condition.

As used herein, the term "target protein" refers to a molecule or a portion of a protein capable of being bound by a selective binding compound. In certain embodiments, a target protein is Btk.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, the $IC_{50}$ refers to an amount, concentration or dosage of a particular test compound that achieves a 50% inhibition of a maximal response, such as inhibition of Btk, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

DETAILED DESCRIPTION OF THE INVENTION

Inhibitor Compounds

In the following description of kinase inhibitor compounds suitable for use in the methods described herein, definitions of referred-to standard chemistry terms may be found in reference works (if not otherwise defined herein), including Carey and Sundberg "Advanced Organic Chemistry 4th Ed." Vols. A (2000) and B (2001), Plenum Press, New York. In addition, nucleic acid and amino acid sequences for Btk (e.g., human Btk) are disclosed in, e.g., U.S. Pat. No. 6,326,469. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients In one aspect, provided herein are compounds of Formula (I) having the structure:

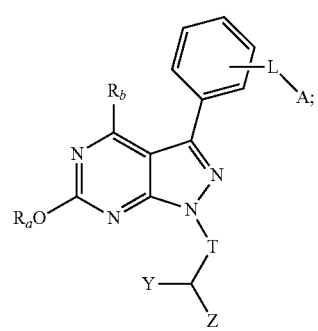

Formula (I)

wherein:
L is a bond, CH$_2$, O, NR$_2$, S, CO, C=NR$_2$, or C=N—OR$_2$;
T is a bond, C$_1$-C$_6$alkylene, or C$_3$-C$_6$cycloalkylene;
A is aryl or heteroaryl wherein aryl or heteroaryl is optionally substituted with at least one R$_1$;
Y and Z are each independently selected from H, C$_1$-C$_6$alkyl, C$_2$-C$_6$alkenyl, C$_3$-C$_{10}$cycloalkyl, C$_1$-C$_6$heteroalkyl, C$_2$-C$_6$heteroalkenyl, C$_4$-C$_{10}$heterocycloalkenyl and C$_2$-C$_{10}$heterocycloalkyl, wherein C$_1$-C$_6$alkyl, C$_2$-C$_6$alkenyl, C$_3$-C$_{10}$cycloalkyl, C$_1$-C$_6$heteroalkyl, C$_2$-C$_6$heteroalkenyl, C$_4$-C$_{10}$heterocycloalkenyl and C$_2$-C$_{10}$heterocycloalkyl are optionally substituted with at least one R$_1$; or
Y and Z together with the carbon atom to which they are attached form a C$_3$-C$_{10}$cycloalkyl, C$_2$-C$_{10}$heterocycloalkyl, C$_4$-C$_{10}$heterocycloalkenyl, aryl, or heteroaryl, wherein C$_3$-C$_{10}$cycloalkyl, C$_2$-C$_{10}$heterocycloalkyl, C$_4$-C$_{10}$heterocycloalkenyl, aryl, or heteroaryl, are optionally substituted with at least one X;
wherein when Y and Z together with the carbon atom to which they are attached form a nitrogen atom-containing C$_2$-C$_{10}$heterocycloalkyl or C$_4$-C$_{10}$heterocycloalkenyl, the nitrogen atom of the C$_2$-C$_{10}$heterocycloalkyl or C$_4$-C$_{10}$heterocycloalkenyl is optionally substituted with W and the carbon atoms of the C$_2$-C$_{10}$heterocycloalkyl or C$_4$-C$_{10}$heterocycloalkenyl are optionally substituted with at least one X;
W is selected from J, C(=O)-J, C(=O)O-J, C(=O)NR$_2$-J, C(=NR$_2$)-J, —C(=NR$_2$)NR$_2$-J, C(=N—OR$_3$)-J, C(=S)-J, S(=O)$_v$-J, S(=O)$_v$O-J;
X is F, Cl, Br, I, —CN, —NO$_2$, —OR$_3$, —N(R$_2$)$_2$, —SR$_2$, —C$_1$-C$_6$alkyl, —C(=O)R$_2$, —OC(=O)R$_2$, —NR$_2$C(=O)R$_2$, —NR$_2$C(=O)N(R$_2$)$_2$, —C(=O)N(R$_2$)$_2$, —C(=NR$_2$)N(R$_2$)$_2$, —C(=N—OR$_2$)N(R$_2$)$_2$, —C(=S)R$_2$, —S(=O)$_v$R$_2$, —OS(=O)$_v$R$_2$, —NR$_2$C(=O)OR$_2$, —NR$_2$S(=O)$_v$R$_2$;
J is —C$_1$-C$_6$alkyl, C$_3$-C$_6$cycloalkyl, —C$_2$-C$_6$alkene, C$_2$-C$_6$heterocycloalkyl, aryl, or heteroaryl optionally substituted with at least one R$_1$;
v is 1 or 2;
R$_a$ is H, —SO$_3$H, or C$_1$-C$_4$alkyl;
R$_b$ is NH$_2$, OH, OSO$_3$H or NHSO$_3$H;
R$_1$ is selected from F, Cl, Br, I, —CN, —NO$_2$, —SR$_2$, —OR$_3$, C$_1$-C$_6$alkyl, C$_1$-C$_6$haloalkyl, C$_1$-C$_6$hydroxyalkyl, —OC$_1$-C$_6$haloalkyl, C$_1$-C$_6$heteroalkyl, C$_3$-C$_6$cycloalkyl, C$_2$-C$_6$heterocycloalkyl, phenyl, —NR$_2$S(=O)$_2$R$_2$, —S(=O)$_2$N(R$_2$)$_2$, —C(=O)CF$_3$, —C(=O)NR$_2$S(=O)$_2$R$_2$, —S(=O)$_2$NR$_2$C(=O)R$_2$, —N(R$_2$)$_2$, wherein optionally the two R$_2$ groups of N(R$_2$)$_2$ and the nitrogen atom to which they are attached form a C$_2$-C$_6$heterocycloalkyl ring, —NR$_2$C(=O)R$_2$, —NR$_2$C(=O)N(R$_2$)$_2$, —CO$_2$R$_2$, —C(=O)R$_2$, —OC(=O)R$_2$, —C(=O)N(R$_2$)$_2$, —OS(=O)$_2$R$_2$, —OS(=O)$_2$OR$_2$, —S(=O)R$_2$, —S(=O)$_2$R$_2$, —SO$_3$H, and at least one amino acid fragment;
R$_2$ is H, C$_1$-C$_6$alkyl, C$_1$-C$_6$haloalkyl, C$_1$-C$_6$hydroxyalkyl, or C$_3$-C$_6$cycloalkyl; R$_3$ is H, methyl, ethyl, n-propyl, iso-propyl, n-butyl, iso-butyl, tert-butyl, or SO$_3$H; or a pharmaceutically acceptable salt, solvate, or tautomeric form thereof.

For any and all of the embodiments, substituents are optionally selected from among from a subset of the listed alternatives. For example, in some embodiments, L is a bond, CH$_2$, O, NR$_2$, S, CO, C=NR$_2$, or C=N—OR$_2$. In other embodiments, L is a bond or O. In yet other embodiments, L is O.

In some embodiments, A is an aryl substituted with at least one R$_1$. In yet other embodiments, A is a 6-membered aryl. In some other embodiments, A is phenyl. In other embodiments, phenyl is substituted with one R$_1$ selected from F, Cl, Br, I, —CN, NO$_2$, —SR$_2$, —OR$_3$, —N(R$_2$)$_2$, methyl, and ethyl. In further embodiments, phenyl is substituted with —OH, or —OSO$_3$H. In yet further embodiments, phenyl is substituted with two R$_1$ selected from F, Cl, Br, I, —CN, NO$_2$, —SR$_2$, and —OR$_3$. In another embodiment, phenyl is substituted with two —OH, two —OSO$_3$H or —OH and —OSO$_3$H. In some embodiments, T is a bond. In other embodiments, T is C$_1$-C$_6$alkylene. In further embodiments, C$_1$-C$_6$alkylene is CH$_2$. In other embodiments, R$_a$ is H, R$_b$ is NH$_2$, and L is O. In another embodiment, Y is C$_1$-C$_6$alkyl or C$_2$-C$_6$alkene. In one embodiment, C$_1$-C$_6$alkyl or C$_2$-C$_6$alkene is substituted with —C(=O)R$_2$ or —CO$_2$R$_2$. In a further embodiment, R$_2$ is H. In one embodiment, Z is C$_1$-C$_6$alkyl. In one embodiment, C$_1$-C$_6$alkyl is substituted with —C(=O)R$_2$, —OC(=O)R$_2$, —NR$_2$C(=O)R$_2$, or —C(=O)N(R$_2$)$_2$. In one embodiment, C$_1$-C$_6$alkyl is substituted with —NR$_2$C(=O)R$_2$. In one embodiment, each R$_2$ is H. In one embodiment, R$_2$ is C$_1$-C$_6$alkyl. In another embodiment, C$_1$-C$_6$alkyl is selected from methyl, ethyl, n-propyl, iso-propyl, n-butyl, iso-butyl, or tert-butyl. In one embodiment, R$_2$ is C$_1$-C$_6$hydroxyalkyl.

In one embodiment, Y and Z together with the carbon atom to which they are attached form a nitrogen atom-containing C$_2$-C$_{10}$heterocycloalkyl. In another embodiment, the nitrogen atom-containing C$_2$-C$_{10}$heterocycloalkyl is selected from:

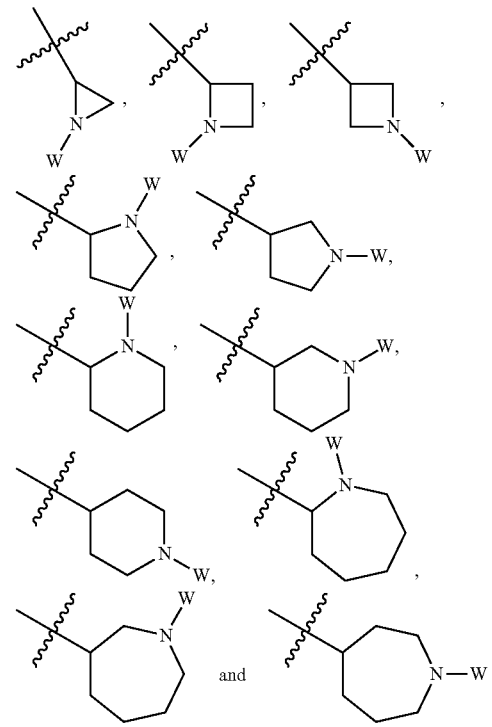

In yet another embodiment, the nitrogen atom-containing C$_2$-C$_{10}$heterocycloalkyl is

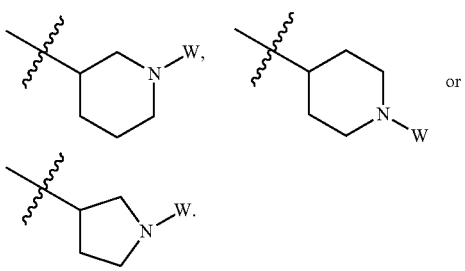

In a further embodiment,

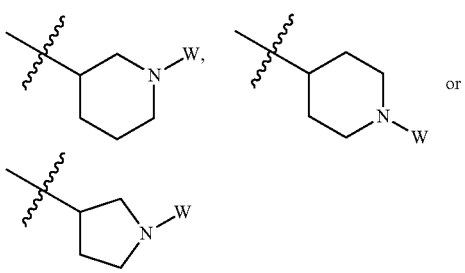

is substituted with at least one X. In yet a further embodiment, X is selected from F, Cl, Br, I, —CN, —OR$_3$, and NO$_2$. In one embodiment, X is —OH or —OSO$_3$H. In another embodiment, W is selected from J, C(=O)-J, C(=O)O-J, and C(=O)NR$_2$-J. In yet another embodiment, W is C(=O)-J. In a further embodiment, J is C$_1$-C$_6$alkyl.

In yet a further embodiment, C$_1$-C$_6$alkyl is methyl, ethyl, n-propyl, iso-propyl, n-butyl, iso-butyl, and tert-butyl. In one embodiment, C$_1$-C$_6$alkyl is substituted with one R$_1$. In another embodiment, C$_1$-C$_6$alkyl is substituted with two R$_1$. In yet another embodiment, R$_1$ is selected from F, Cl, Br, I, —CN, NO$_2$, —OR$_3$, and at least one amino acid fragment. In a further embodiment, W is J. In yet a further embodiment, J is C$_1$-C$_6$alkyl. In one embodiment, C$_1$-C$_6$alkyl is methyl, ethyl, n-propyl, iso-propyl, n-butyl, iso-butyl, and tert-butyl. In another embodiment, C$_1$-C$_6$alkyl is substituted with one R$_1$. In yet another embodiment, C$_1$-C$_6$alkyl is substituted with two R$_1$. In a further embodiment, R$_1$ is selected from F, Cl, Br, I, —CN, NO$_2$, and OR$_3$. In yet another embodiment, R$_1$ is at least one amino acid fragment. In one embodiment, the at least one amino acid fragment is a cysteine or glutathione fragment. In another embodiment, one R$_1$ is an amino fragment and the other R$_1$ is selected from F, Cl, Br, I, —CN, NO$_2$, —OH, and —OSO$_3$H. In yet another embodiment, the at least one amino acid fragment is a di-peptide fragment. In a further embodiment, the at least one amino acid fragment is a tri-peptide fragment. In yet a further embodiment, the di-peptide fragment is a fragment of Cys-Gly. In one embodiment, J is C$_2$-C$_6$alkene. In another embodiment, C$_2$-C$_6$alkene is C$_2$H$_3$. In one embodiment, C$_2$-C$_6$alkene is substituted with at least one R$_1$ selected from F, Cl, Br, I, —CN, NO$_2$, OH, and —OSO$_3$H. In one embodiment, J is C$_2$-C$_6$heterocycloalkyl. In another embodiment C$_2$-C$_6$heterocycloalkyl is an epoxide. In a further embodiment, is a compound of Formula (I) wherein R$_1$ is selected from —NR$_2$S(=O)$_2$R$_2$, —S(=O)$_2$N(R$_2$)$_2$, —C(=O)NR$_2$S(=O)$_2$R$_2$, —S(=O)$_2$NR$_2$C(=O)R$_2$, —OS(=O)$_2$R$_2$, —OS(=O)$_2$OR$_2$, —S(=O)R$_2$, or —S(=O)$_2$R$_2$. In one embodiment, R$_1$ is OS(=O)$_2$R$_2$. In one embodiment, R$_1$ is —S(=O)$_2$R$_2$. In another embodiment, R$_2$ is C$_1$-C$_6$haloalkyl. In a further embodiment, C$_1$-C$_6$haloalkyl is CF$_3$.

In one embodiment, the tautomeric form of the compound of Formula (I) has the structure of Formula (IA):

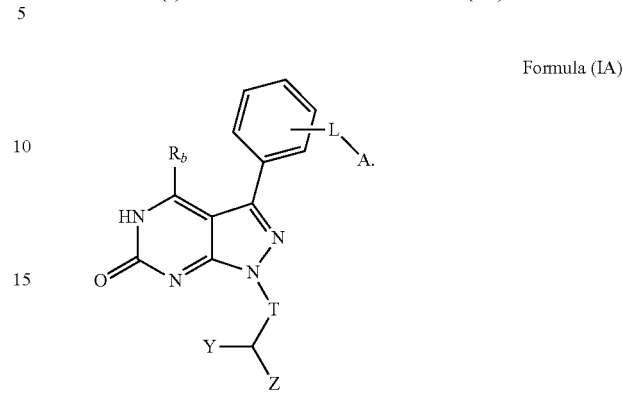

Formula (IA)

Any combination of the groups described above for the various variables is contemplated herein.

In another aspect is a compound having the structure of Formula (II):

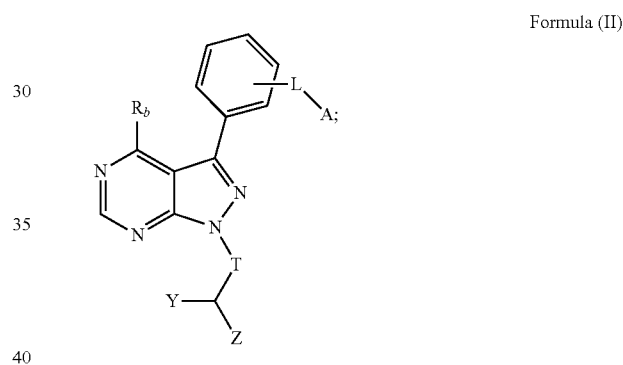

Formula (II)

wherein:
L is a bond, CH$_2$, O, NR$_3$, S, CO, C=NR$_2$, or C=N—OR$_2$;
T is a bond, C$_1$-C$_6$alkylene, or C$_3$-C$_6$cycloalkylene;
A is aryl or heteroaryl wherein aryl or heteroaryl is optionally substituted with at least one R$_1$;
Y is C$_1$-C$_6$alkylene-CO$_2$H or C$_2$-C$_6$alkenylene-C(=O)H;
Z is C$_1$-C$_6$alkylene-NR$_2$C(=O)C$_1$-C$_6$alkyl optionally substituted with at least one R$_1$; or
Y and Z together with the carbon atom to which they are attached form a

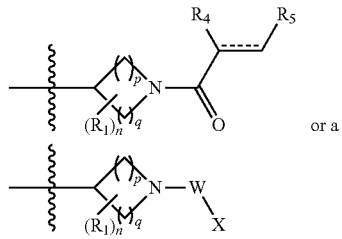

group; ⫽ is a single bond or a cis or trans-double bond;
p is 0-6;
q is 0-6; wherein p+q is ≥1;

n is 0-4;

$R_1$ is selected from F, Cl, Br, I, —CN, —NO$_2$, —SR$_2$, —OR$_3$, C$_1$-C$_6$alkyl, C$_1$-C$_6$haloalkyl, C$_1$-C$_6$hydroxyalkyl, —OC$_1$-C$_6$haloalkyl, C$_1$-C$_6$heteroalkyl, C$_3$-C$_6$cycloalkyl, C$_2$-C$_6$heterocycloalkyl, phenyl, —NR$_3$S(=O)$_2$R$_2$, —S(=O)$_2$N(R$_2$)$_2$, —C(=O)CF$_3$, —C(=O)NR$_3$S(=O)$_2$R$_2$, —S(=O)$_2$NR$_3$C(=O)R$_2$, —N(R$_2$)$_2$, wherein optionally the two R$_2$ groups of N(R$_2$)$_2$ and the nitrogen atom to which they are attached form a C$_2$-C$_6$ heterocycloalkyl ring, —NR$_2$C(=O)R$_2$, —NR$_2$C(=O)NR$_2$, —CO$_2$R$_2$, —C(=O)R$_2$, —OC(=O)R$_2$, —C(=O)N(R$_2$)$_2$, —OS(=O)$_2$R$_2$, —OS(=O)$_2$OR$_2$, —S(=O)R$_2$, —S(=O)$_2$R$_2$, and at least one amino acid fragment;

$R_b$ is NH$_2$, OH, OSO$_3$H or NHSO$_3$H;

$R_2$ is H, C$_1$-C$_6$alkyl, C$_1$-C$_6$haloalkyl, C$_1$-C$_6$hydroxyalkyl, C$_1$-C$_6$dihydroxyalkyl, or C$_3$-C$_6$cycloalkyl;

$R_3$ is H, methyl, ethyl, n-propyl, iso-propyl, n-butyl, iso-butyl, tert-butyl or SO$_3$H;

$R_4$ and $R_5$ are each independently selected from H, F, Cl, Br, I, —CN, —NO$_2$, —SR$_2$, —OR$_3$, C$_1$-C$_6$alkyl, C$_1$-C$_6$haloalkyl, C$_1$-C$_6$hydroxyalkyl, —OC$_1$-C$_6$haloalkyl, C$_1$-C$_6$heteroalkyl, C$_3$-C$_6$cycloalkyl, C$_2$-C$_6$heterocycloalkyl, phenyl, —OSO$_3$H, —NR$_2$S(=O)$_2$R$_2$, —S(=O)$_2$N(R$_2$)$_2$, —C(=O)CF$_3$, —C(=O)NR$_2$S(=O)$_2$R$_2$, —S(=O)$_2$NR$_2$C(=O)R$_2$, —N(R$_2$)$_2$, —NR$_2$C(=O)R$_2$, —CO$_2$R$_2$, —C(=O)R$_2$, —OC(=O)R$_2$, —C(=O)N(R$_2$)$_2$, —OS(=O)$_2$R$_2$, —OS(=O)$_2$OR$_2$, —S(=O)R$_2$, —S(=O)$_2$R$_2$, and at least one amino acid fragment; or optionally when ⫶⫶ is a single bond then R$_4$ and R$_5$ together with the carbon atoms to which they are attached form an epoxide; wherein when ⫶⫶ is a single bond then R$_4$ and R$_5$ are not both hydrogen;

W is selected from —C(=O)—, —C(=O)R$_2$—, —C(=O)OR$_2$—, —C(=NR$_2$)—, —C(=N—OR$_3$)—, —(C=S)—, —S(=O)$_v$—;

X is

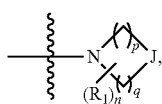

wherein J is O, NR$_6$ or C(R$_2$)$_2$.

$R_6$ is selected from H, C$_1$-C$_6$haloalkyl, C$_1$-C$_6$hydroxyalkyl, C$_1$-C$_6$heteroalkyl, C$_3$-C$_6$cycloalkyl, C$_2$-C$_6$heterocycloalkyl, phenyl, —S(=O)$_2$N(R$_2$)$_2$, —C(=O)CF$_3$, —CO$_2$R$_2$, —C(=O)R$_2$, —C(=O)N(R$_2$)$_2$, —OS(=O)$_2$R$_2$, —OS(=O)$_2$OR$_2$, —S(=O)R$_2$, —S(=O)$_2$R$_2$; or a pharmaceutically acceptable salt, tautomer, or solvate thereof.

In one embodiment is a compound of Formula (II) wherein T is a bond. In one embodiment is a compound of Formula (II) wherein T is C$_1$-C$_6$alkylene. In another C$_1$-C$_6$alkylene is CH$_2$. In yet another embodiment is a compound of Formula (II) wherein L is O and R$_b$ is NH$_2$. In a further embodiment A is aryl. In yet a further embodiment aryl is phenyl. In one embodiment phenyl is substituted with one R$_1$ selected from F, Cl, Br, I, —CN, NO$_2$, —OH, —SR$_2$, and —OR$_3$. In another embodiment is a compound of Formula (II) wherein phenyl is substituted with —OH or —OSO$_3$H. In yet another embodiment is a compound of Formula (II) wherein phenyl is substituted with two R$_1$ selected from F, Cl, Br, I, —CN, NO$_2$, —SR$_2$, and —OR$_3$. In a further embodiment is a compound of Formula (II) wherein phenyl is substituted with two —OH or two —OSO$_3$H or —OH and —OSO$_3$H. In yet a further embodiment Y is C$_1$-C$_6$alkylene -CO$_2$H. In one embodiment C$_1$-C$_6$alkylene is C$_2$H$_5$. In another embodiment is a compound of Formula (II) wherein Y is C$_2$-C$_6$alkenylene-C(=O)H. In yet another embodiment C$_2$-C$_6$alkenylene is C$_2$H$_3$. In a further embodiment is a compound of Formula (II) wherein Z is CH$_2$—NHC(=O)C$_1$-C$_6$alkyl. In yet a further embodiment C$_1$-C$_6$alkyl is selected from methyl, ethyl, n-propyl, iso-propyl, n-butyl, iso-butyl, or tert-butyl. In one embodiment is a compound of Formula (II) wherein Y and Z together with the carbon atom to which they are attached form a

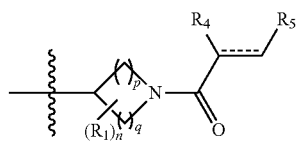

group. In a further embodiment, p is 1 and q is 0-3. In a further embodiment, q is 3. In yet a further embodiment, is a compound of Formula (II) wherein Y and Z together with the carbon atom to which they are attached form a

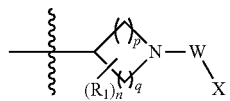

group. In one embodiment, Y and Z together with the carbon atom to which they are attached form a

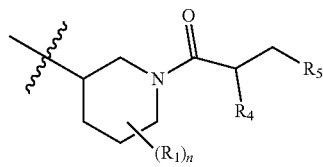

group. In another embodiment is a compound of Formula (II) wherein R$_4$ and R$_5$ are each independently selected from H, F, Cl, Br, I, —CN, —NO$_2$, —SR$_2$, —OR$_3$, C$_1$-C$_6$alkyl, and at least one amino acid fragment. In a further embodiment is a compound of Formula (II) wherein R$_4$ is H and R$_5$ is —OH. In yet another embodiment is a compound of Formula (II) wherein R$_4$ is —OH and R$_5$ is H. In one embodiment is a compound of Formula (II) wherein R$_4$ and R$_5$ are both —OH. In yet a further embodiment is a compound of Formula (II) wherein R$_4$ is H and R$_5$ is at least one amino acid fragment. In one embodiment is a compound of Formula (II) wherein the at least one amino acid fragment is a cysteine or glutathione fragment. In one embodiment is a compound of Formula (II) wherein R$_1$ is selected from F, Cl, Br, I, —CN, —NO$_2$, —SR$_2$, —OR$_3$, and C$_1$-C$_6$alkyl. In one embodiment is a compound of Formula (II) wherein R$_1$ is —OH or —OSO$_3$H. In a further embodiment is a compound of Formula (II) wherein X is

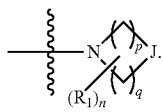

In one embodiment, p is 1, and q is 2. In another embodiment, J is C(R₂)₂. In a further embodiment, each R₂ is hydrogen. In yet another embodiment, p is 2, q is 2 and J is O. In yet a further embodiment, X is morpholine or pyrrolidine. In yet a further embodiment, X is substituted with at least one R₁.

In another embodiment is a compound having the structure:

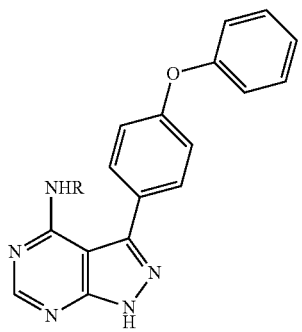

wherein R is an amino protecting group; or a pharmaceutically acceptable salt, solvate, or metabolite thereof. In another embodiment, the amino protecting group is selected from Fmoc, Boc, Cbz, Ac, trifluoroacetamide, Bn, trityl, benzylideneamine, Ts, or the H attached to the nitrogen atom of the primary amine is absent and R and the nitrogen atom to which it is attached form a phthalimide group; or a pharmaceutically acceptable salt, solvate, or metabolite thereof.

In one embodiment, R is a Boc group. In another embodiment, R is an Fmoc group. In a further embodiment, R is a Cbz group.

In a further embodiment is a compound selected from:

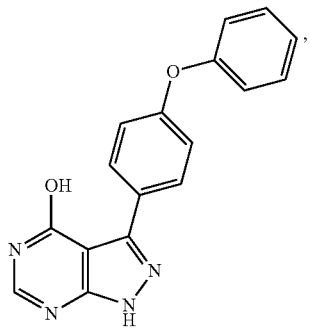

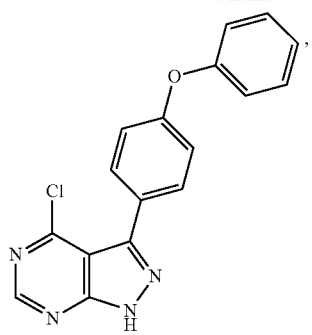

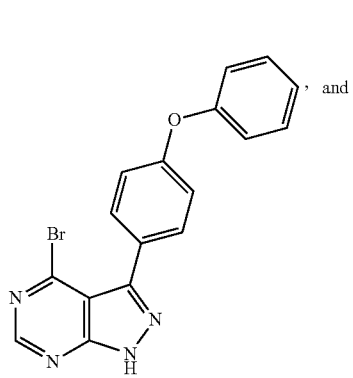

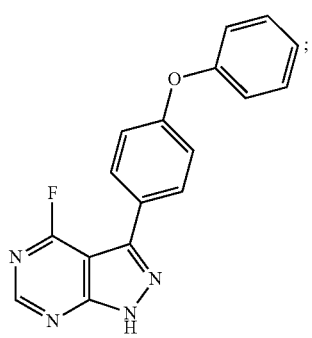

or a pharmaceutically acceptable salt, solvate, or metabolite thereof.

In one embodiment is a compound having the structure:

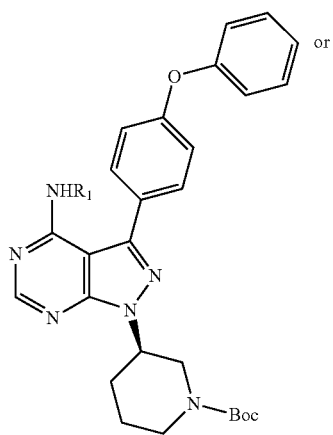

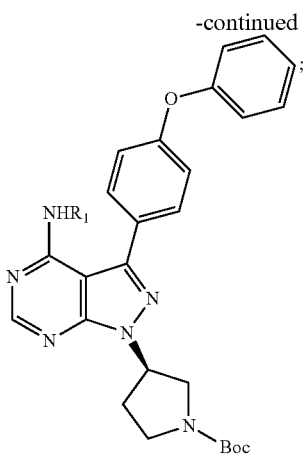

wherein $R_1$ is H or an amino protecting group. In another embodiment, the amino protecting group is selected from Fmoc, Boc, Cbz, Ac, trifluoroacetamide, Bn, trityl, benzylideneamine, Ts, or the H attached to the nitrogen atom of the primary amine is absent and $R_1$ and the nitrogen atom to which it is attached form a phthalimide group; or a pharmaceutically acceptable salt, solvate, or metabolite thereof.

In one embodiment, $R_1$ is H. In one embodiment, $R_1$ is a Boc group. In another embodiment, $R_1$ is an Fmoc group. In a further embodiment, $R_1$ is a Cbz group.

In another embodiment is a compound having the structure:

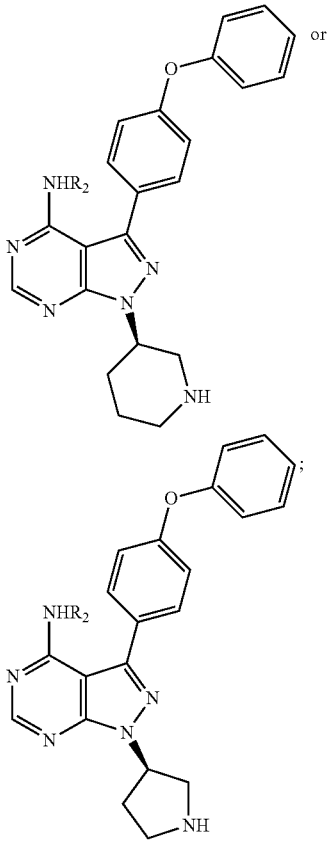

wherein $R_2$ is H, an an amino protecting group, $C_1$-$C_6$alkyl, $C(=O)C_1$-$C_6$alkyl, or $C(=O)C_2$-$C_6$alkene; wherein $C_1$-$C_6$alkyl, $C(=O)C_1$-$C_6$alkyl, $C(=O)C_2$-$C_6$alkene is optionally substituted with at least one substituent selected from F, Cl, Br, I, —CN, —NO$_2$, —SR$_2$, —OR$_3$, $C_1$-$C_6$alkyl, $C_1$-$C_6$haloalkyl, $C_1$-$C_6$hydroxyalkyl, —OC$_1$-$C_6$haloalkyl, $C_1$-$C_6$heteroalkyl, $C_3$-$C_6$cycloalkyl, $C_2$-$C_6$heterocycloalkyl, phenyl, —OSO$_3$H, —NR$_2$S(=O)$_2$R$_2$, —S(=O)$_2$N(R$_2$)$_2$, —C(=O)CF$_3$, —C(=O)NR$_2$S(=O)$_2$R$_2$, —S(=O)$_2$NR$_2$C(=O)R$_2$, —N(R$_2$)$_2$, —NR$_2$C(=O)R$_2$, —CO$_2$R$_2$, —C(=O)R$_2$, —OC(=O)R$_2$, —C(=O)N(R$_2$)$_2$, —OS(=O)$_2$R$_2$, —OS(=O)$_2$OR$_2$, —S(=O)R$_2$, —S(=O)$_2$R$_2$ wherein $R_2$ is H or $C_1$-$C_6$alkyl. In another embodiment, the amino protecting group is selected from Fmoc, Boc, Cbz, Ac, trifluoroacetamide, Bn, trityl, benzylideneamine, Ts, or the H attached to the nitrogen atom of the primary amine is absent and $R_2$ and the nitrogen atom to which it is attached form a phthalimide group; or a pharmaceutically acceptable salt, solvate, or metabolite thereof.

In one embodiment, $R_2$ is H. In another embodiment, $R_2$ is a Boc group. In another embodiment, $R_2$ is an Fmoc group. In a further embodiment, $R_2$ is a Cbz group.

In another embodiment, $R_2$ is C(=O)CHCH$_2$. In another embodiment, $R_2$ is C(=O)CH$_2$CH$_2$OH. In a further embodiment, $R_2$ is CH$_2$Cl. In yet a further embodiment, $R_2$ is CHCl$_2$.

In one embodiment is a compound having the structure:

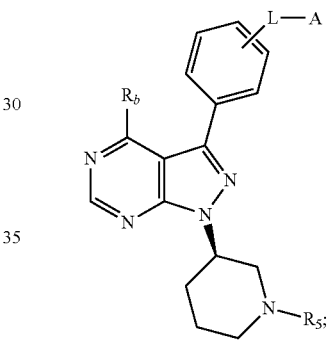

wherein L is a bond, CH$_2$, O, NR$_3$, S, CO, C=NR$_2$, or C=N—OR$_2$;

A is aryl or heteroaryl wherein aryl or heteroaryl is optionally substituted with at least one $R_1$;

$R_1$ is selected from F, Cl, Br, I, —CN, —NO$_2$, —SR$_2$, —OR$_3$, $C_1$-$C_6$haloalkyl, $C_1$-$C_6$hydroxyalkyl, —OC$_1$-$C_6$haloalkyl, $C_1$-$C_6$heteroalkyl, $C_3$-$C_6$cycloalkyl, $C_2$-$C_6$heterocycloalkyl, phenyl, —NR$_3$S(=O)$_2$R$_2$, —S(=O)$_2$N(R$_2$)$_2$, —C(=O)CF$_3$, —C(=O)NR$_3$S(=O)$_2$R$_2$, —S(=O)$_2$NR$_3$C(=O)R$_2$, —N(R$_2$)$_2$, wherein optionally the two $R_2$ groups of N(R$_2$)$_2$ and the nitrogen atom to which they are attached form a $C_2$-$C_6$ heterocycloalkyl ring, —NR$_2$C(=O)R$_2$, —NR$_2$C(=O)NR$_2$, —CO$_2$R$_2$, —C(=O)R$_2$, —OC(=O)R$_2$, —C(=O)N(R$_2$)$_2$, —OS(=O)$_2$R$_2$, —OS(=O)$_2$OR$_2$, —S(=O)R$_2$, —S(=O)$_2$R$_2$, and at least one amino acid fragment;

$R_b$ is NH$_2$, OH, OSO$_3$H or NHSO$_3$H;

$R_2$ is H, $C_1$-$C_6$alkyl, $C_1$-$C_6$haloalkyl, $C_1$-$C_6$hydroxyalkyl, $C_1$-$C_6$dihydroxyalkyl, or $C_3$-$C_6$cycloalkyl; and $R_5$ is a substituted (C(O))alkyl or a substituted (C(O)) alkenyl.

In one embodiment, $R_5$ is a substituted C((O)—$C_1$-$C_6$alkyl. In another embodiment, $R_5$ is a substituted C(O)-ethyl. In a further embodiment, $R_5$ is a substituted C(O)-propyl. In a further embodiment, $R_5$ is a substituted C((O)—$C_2$-$C_6$alkenyl. In a further embodiment, $R_5$ is a substituted C(O)-ethylene. In one embodiment, C(O)alkyl or C(O)alkenyl is substituted with at least one $R_1$ group. In one embodiment, $R_5$ is substituted with at least two $R_1$ groups. In a further embodiment, at least three $R_1$ groups. In yet a further embodiment, at least four $R_1$ groups.

In a further embodiment is a compound having the structure:

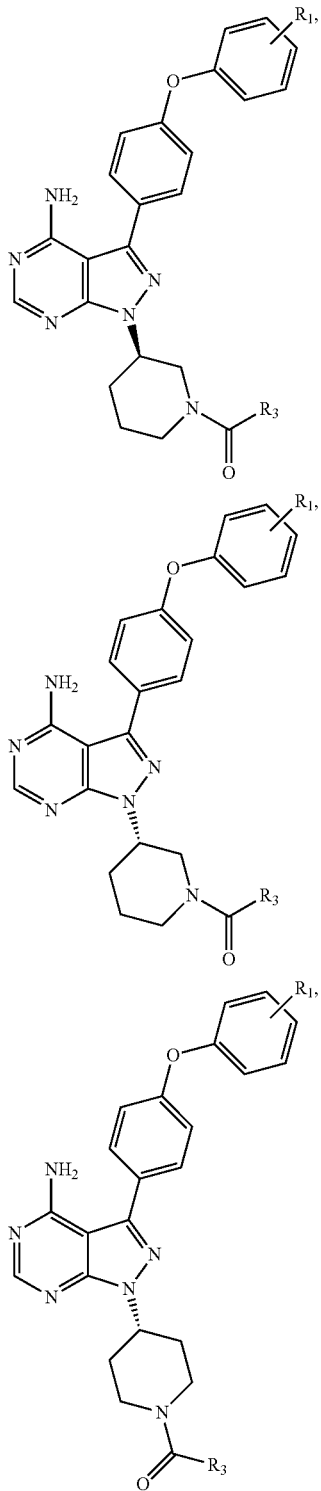

-continued

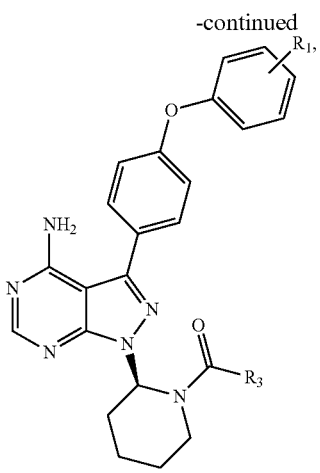

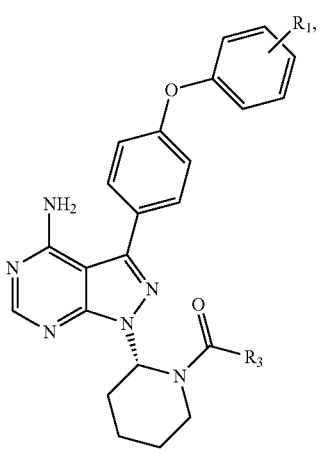

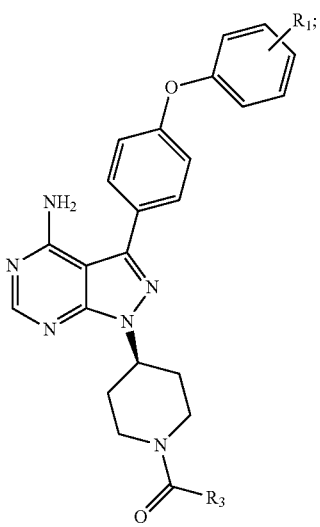

or a pharmaceutically acceptable salt, solvate, or metabolite thereof wherein the following compounds, having different substituents (for e.g., $R_1$ and $R_3$) are listed in the table below:

| Cmpd # | R₃ | R₁ | Cmpd # | R₃ | R₁ |
|---|---|---|---|---|---|
| 1 | -CH₂CH₂Cl | H | 3 | -CH₂CH₂Cl | 4-OH |
| 2 | -CH₂CH₂Cl | 3-OH | 4 | -CH₂CH₂Cl | 2-OH |
| 5 | -CH=CH-CH₂-N(CH₃)₂ | 4-OH | 17 | -CH=CH-CH₂-N(CH₃)₂ | 3-OH |
| 6 | -CH=CH-CH₂-N(CH₃)₂ | 2-OH | 18 | -CH=CH-CH₂-N(CH₃)₂ | 3,4-dihydroxy |
| 7 | -CH=CH-CH₂-NHCH₃ | H | 19 | -CH=CH-CH₂-NHCH₃ | 4-OH |
| 8 | -CH=CH-CH₂-NHCH₃ | 3-OH | 20 | -CH=CH-CH₂-NHCH₃ | 2-OH |
| 9 | epoxide-CH₂-N(CH₃)₂ | 3-OH | 21 | -CH=CH-CH₂-NHCH₃ | 3,4-dihydroxy |
| 10 | epoxide-CH₂-N(CH₃)₂ | H | 22 | epoxide-CH₂-N(CH₃)₂ | 4-OH |
| 11 | epoxide-CH₂-N(CH₃)₂ | 2-OH | 23 | epoxide-CH₂-N(CH₃)₂ | 3,4-dihydroxy |
| 12 | epoxide-CH₂-NHCH₃ | H | 24 | epoxide-CH₂-NHCH₃ | 4-OH |
| 13 | epoxide-CH₂-NHCH₃ | 3-OH | 25 | epoxide-CH₂-NHCH₃ | 2-OH |

-continued

| Cmpd # | R₃ | R₁ | Cmpd # | R₃ | R₁ |
|---|---|---|---|---|---|
| 14 | CH(OH)CH(OH)CH₂N(CH₃)₂ | 3-OH | 26 | epoxide-CH₂NHCH₃ | 3,4-dihydroxy |
| 15 | CH(OH)CH(OH)CH₂N(CH₃)₂ | H | 27 | CH(OH)CH(OH)CH₂N(CH₃)₂ | 4-OH |
| 16 | CH(OH)CH(OH)CH₂N(CH₃)₂ | 2-OH | 28 | CH(OH)CH(OH)CH₂N(CH₃)₂ | 3,4-dihydroxy |
| 29 | CH(OH)CH₂Cl | H | 44 | CH(OH)CH₂Cl | 4-OH |
| 30 | CH(OH)CH₂Cl | 3-OH | 45 | CH(OH)CH₂Cl | 2-OH |
| 31 | CH=CHCH₂NH₂ | 3-OH | 46 | CH(OH)CH₂Cl | 3,4-dihydroxy |
| 32 | CH=CHCH₂NH₂ | 4-OH | 47 | CH(OH)CH(OH)CH₂NHCH₃ | H |
| 33 | CH=CHCH₂NH₂ | H | 48 | CH=CHCH₂NH₂ | 3,4-dihydroxy |
| 34 | CH=CHCH₂NH₂ | 2-OH | 49 | epoxide-CH₂NH₂ | 4-OH |
| 35 | epoxide-CH₂NH₂ | H | 50 | epoxide-CH₂NH₂ | 3,4-dihydroxy |

-continued

| Cmpd # | R₃ | R₁ | Cmpd # | R₃ | R₁ |
|---|---|---|---|---|---|
| 36 | epoxide-CH₂NH₂ | 3-OH | 51 | CH(OH)CH(OH)CH₂NH₂ | 3,4-dihydroxy |
| 37 | CH(OH)CH(OH)CH₂NH₂ | H | 52 | CH(OH)CH(OH)CH₂NH₂ | 4-OH |
| 38 | CH(OH)CH(OH)CH₂NH₂ | 2-OH | 53 | CH=CH-CH₂-N(CH₃)₂ | 3-OH |
| 39 | CH=CH-CH₂-N(CH₃)₂ | H | 54 | CH=CH-CH₂-N(CH₃)₂ | 4-OH |
| 40 | CH=CH-CH₂-N(CH₃)₂ | 2-OH | 55 | CH=CH-CH₂-N(CH₃)₂ | 3,4-dihydroxy |
| 41 | CH=CH-CH₂-NHCH₃ | H | 56 | CH=CH-CH₂-NHCH₃ | 4-OH |
| 42 | CH=CH-CH₂-NHCH₃ | 3-OH | 57 | CH=CH-CH₂-NHCH₃ | 3,4-dihydroxy |
| 43 | CH=CH-CH₂-NHCH₃ | 2-OH | 58 | CH=CH-CH₂-NH₂ | 3,4-dihydroxy |
| 59 | CH=CH-CH₂-NH₂ | 3-OH | 78 | CH=CH-CH₂-NH₂ | 4-OH |
| 60 | CH=CH-CH₂-NH₂ | 2-OH | 79 | CH=CH-CH₂-NH₂ | H |
| 61 | CH(Cl)CH₂Cl | 3-OH | 80 | CH(Cl)CH₂Cl | 3,4-dihydroxy |
| 62 | CH(Cl)CH₂Cl | H | 81 | CH(Cl)CH₂Cl | 4-OH |
| 63 | CH(Cl)CH₂Cl | 2-OH | 82 | CH(Cl)CH₃ | 3,4-dihydroxy |

-continued

| Cmpd # | R₃ | R₁ | Cmpd # | R₃ | R₁ |
|---|---|---|---|---|---|
| 64 | CH(Cl)CH₃ | H | 83 | CH(Cl)CH₃ | 4-OH |
| 65 | CH(Cl)CH₃ | 3-OH | 84 | CH(Cl)CH₃ | 2-OH |
| 66 | CH(Cl)CH₂OH | H | 85 | CH(Cl)CH₂OH | 4-OH |
| 67 | CH(Cl)CH₂OH | 3-OH | 86 | CH(Cl)CH₂OH | 3,4-dihydroxy |
| 68 | CH(Cl)CH₂OH | 2-OH | 87 | CH₂Cl | 3,4-dihydroxy |
| 69 | CH₂Cl | H | 88 | CH₂Cl | 4-OH |
| 70 | CH₂Cl | 3-OH | 89 | CH₂Cl | 2-OH |
| 71 | CH₂OH | H | 90 | CH₂OH | 4-OH |
| 72 | CH₂OH | 3-OH | 91 | CH₂OH | 3,4-dihydroxy |
| 73 | CH₂OH | 2-OH | 92 | CH₂Br | 3-OH |
| 74 | CH₂Br | H | 93 | CH₂Br | 4-OH |
| 75 | CH₂Br | 2-OH | 94 | CH₂Br | 3,4-dihydroxy |
| 76 | CH₃ | H | 95 | CH₃ | 4-OH |
| 77 | CH₃ | 3-OH | 96 | CH₃ | 3,4-dihydroxy |
| 97 | CH₃ | 2-OH | 114 | CH₂CH₂Br | 3-OH |

-continued

| Cmpd # | R₃ | R₁ | Cmpd # | R₃ | R₁ |
|---|---|---|---|---|---|
| 98 | -CH₂CH₂Br | H | 115 | -CH₂CH₂Br | 3,4-dihydroxy |
| 99 | -CH(OH)CH₂Br | 3-OH | 116 | -CH₂CH₂Br | 4-OH |
| 100 | -CH(OH)CH₂Br | H | 117 | -CH(OH)CH₂Br | 4-OH |
| 101 | -CH(OH)CH₂Br | 2-OH | 118 | -CH(OH)CH₂Br | 3,4-dihydroxy |
| 102 | -CH(Cl)CH₂Br | H | 119 | -CH(Cl)CH₂Br | 4-OH |
| 103 | -CH(Cl)CH₂Br | 2-OH | 120 | -CH(Cl)CH₂Br | 3,4-dihydroxy |
| 104 | -CH(Cl)CH₂Br | 3-OH | 121 | -CH(Br)CH₂Br | 3,4-dihydroxy |
| 105 | -CH(Br)CH₂Br | 2-OH | 122 | -CH(Br)CH₂Br | 4-OH |
| 106 | -CH(Br)CH₂Br | H | 123 | -CH(Br)CH₃ | 3,4-dihydroxy |
| 107 | -CH(Br)CH₃ | 2-OH | 124 | -CH(Br)CH₃ | 3-OH |
| 108 | -CH(Br)CH₃ | H | 125 | -CH(Br)CH₃ | 4-OH |
| 109 | -CH(Br)CH₂OH | H | 126 | -CH(Br)CH₂OH | 4-OH |

-continued

| Cmpd # | R₃ | R₁ | Cmpd # | R₃ | R₁ |
|---|---|---|---|---|---|
| 110 | CH(Br)CH₂OH | 2-OH | 127 | CH(Br)CH₂OH | 3,4-dihydroxy |
| 111 | CH(Br)CH₂OH | 3-OH | 128 | CH₂Br | 3,4-dihydroxy |
| 112 | CH₂Br | 2-OH | 129 | CH₂Br | 4-OH |
| 113 | CH₂Br | H | 130 | CH₂CH₂OH | 3,4-dihydroxy |
| 131 | CH₂CH₂OH | H | 148 | CH₂CH₂OH | 4-OH |
| 132 | CH₂CH₂OH | 2-OH | 149 | CH₂CH₂OH | 3-OH |
| 133 | CH₂CH₃ | H | 150 | CH₂CH₃ | 4-OH |
| 134 | CH₂CH₃ | 2-OH | 151 | CH₂CH₃ | 3,4-dihydroxy |
| 135 | CH₂CH₃ | 3-OH | 152 | CH₂CH₂Cl | 3,4-dihydroxy |
| 136 | CH(OH)CH(OH)CH₂NHCH₃ | H | 153 | CH(OH)CH(OH)CH₂NHCH₃ | 2-OH |
| 137 | CH(OH)CH(OH)CH₂NHCH₃ | 4-OH | 154 | CH(OH)CH(OH)CH₂NHCH₃ | 3,4-dihydroxy |
| 138 | CH(OH)CH(OH)CH₂NHCH₃ | 3-OH | 155 | CH(OH)CH(OH)CH₂NH₂ | 3-OH |
| 139 | CH₂CH=CHCH₂N(CH₃)₂ | H | 156 | CH₂CH=CHCH₂N(CH₃)₂ | 3,4-dihydroxy |
| 140 | CH₂CH=CHCH₂N(CH₃)₂ | 4-OH | 157 | CH₂CH=CHCH₂N(CH₃)₂ | 2-OH |
| 141 | CH₂CH=CHCH₂N(CH₃)₂ | 3-OH | 158 | CH₂CH=CHCH₂NH(CH₃) | 2-OH |

-continued

| Cmpd # | R₃ | R₁ | Cmpd # | R₃ | R₁ |
|---|---|---|---|---|---|
| 142 | *CH₂-CH=CH-CH₂-NHCH₃ (cis)* | 3-OH | 159 | *CH₂-CH=CH-CH₂-NHCH₃ (cis)* | 3,4-dihydroxy |
| 143 | *CH₂-CH=CH-CH₂-NHCH₃ (cis)* | 4-OH | 160 | *CH₂-CH=CH-CH₂-NHCH₃ (cis)* | H |
| 144 | *CH₂-CH=CH-CH₂-morpholine (trans)* | 2-OH | 161 | *CH₂-CH=CH-CH₂-morpholine (trans)* | 3-OH |
| 145 | *CH₂-CH=CH-CH₂-morpholine (trans)* | 4-OH | 162 | *CH₂-CH=CH-CH₂-morpholine (trans)* | 3,4-dihydroxy |
| 146 | *CH₂-CH=CH-CH₂-NH₂ (cis)* | H | 163 | *CH₂-CH=CH-CH₂-NH₂ (cis)* | 4-OH |
| 147 | *CH₂-CH=CH-CH₂-NH₂ (cis)* | 2-OH | 164 | *CH₂-CH=CH-CH₂-NH₂ (cis)* | 3,4-dihydroxy |
| 165 | *CH₂-CH=CH-CH₂-NH₂ (cis)* | 3-OH | 178 | *CH₂-CH=CH-CH₂-N(CH₃)CH₂CH₂OH (trans)* | 4-OH |
| 166 | *CH₂-CH=CH-CH₂-N(CH₃)CH₂CH₂OH (trans)* | 2-OH | 180 | *CH₂-CH=CH-CH₂-N(CH₃)CH₂CH₂OH (trans)* | 3,4-dihydroxy |
| 167 | *CH₂-CH=CH-CH₂-N(CH₃)CH₂CH₂OH (trans)* | 3-OH | 181 | *CH=CH-imidazole* | 3,4-dihydroxy |
| 168 | *CH=CH-imidazole* | 2-OH | 182 | *CH=CH-imidazole* | 3-OH |
| 169 | *CH=CH-imidazole* | 4-OH | 183 | CCH | 2-OH |
| 170 | CCH | 3-OH | 184 | CCH | 3,4-dihydroxy |

-continued

| Cmpd # | R₃ | R₁ | Cmpd # | R₃ | R₁ |
|---|---|---|---|---|---|
| 171 | CCH | 4-OH | 185 | (propynyl) | 3,4-dihydroxy |
| 172 | (propynyl) | 2-OH | 186 | (propynyl) | 4-OH |
| 173 | (propynyl) | 3-OH | 187 | (CH=CH-CH₂-OMe) | 3,4-dihydroxy |
| 174 | (CH=CH-CH₂-OMe) | 3-OH | 188 | (CH=CH-CH₂-OMe) | 4-OH |
| 175 | (CH=CH-CH₂-OMe) | 2-OH | 189 | (CH=CH-CH₃) | 2-OH |
| 176 | (CH=CH-CH₃) | 3-OH | 190 | (CH=CH-CH₃) | 3,4-dihydroxy |
| 177 | (CH=CH-CH₃) | 4-OH | 191 | (CH=CH-CH₂-OH) | 2-OH |
| 192 | (CH=CH-CH₂-OH) | 3-OH | 194 | (CH=CH-CH₂-OH) | 3,4-dihydroxy |
| 193 | (CH=CH-CH₂-OH) | 4-OH | — | — | — |

Also disclosed herein is a compound of Formula (IIIA) or (IIIB) having the structure:

wherein $R_b$, T, Y, and Z are as previously described and $R_4$ is H or OH; and $R_5$ is a glycone. In one embodiment, the glycone is a monosaccharide. In another embodiment, the glycone is a disaccharide. In a further embodiment, the glycone is an oligosaccharide. In yet another embodiment, the glycone is glucose. In a further embodiment, the glycone is fructose. In another embodiment, the glycone is mannose. In yet a further embodiment, the glycone is glucuronic acid. In one embodiment, the glycone is attached to the oxygen atom of the compound of Formula (IIIA) or (IIIB) via an α-glycosidic bond. In another embodiment, the glycone is attached to the oxygen atom of the compound of Formula (IIIA) or (IIIB) via a β-glycosidic bond. In one embodiment, the glycone is a pyranose. In another embodiment, the glycone is a furanose.

In one aspect, provided herein are compounds of Formula (IIIC) or (IIID) having the structure:

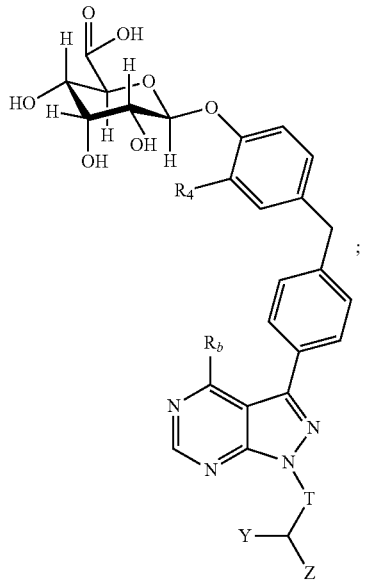

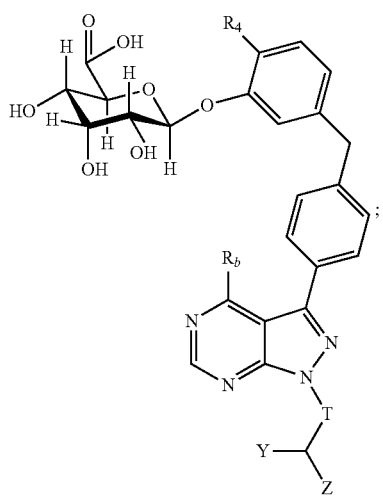

wherein:
T is a bond, $C_1$-$C_6$alkylene, or $C_3$-$C_6$cycloalkylene;
Y and Z are each independently selected from H, $C_1$-$C_6$alkyl, $C_2$-$C_6$alkenyl, $C_3$-$C_{10}$cycloalkyl, $C_1$-$C_6$heteroalkyl, $C_2$-$C_6$heteroalkenyl, $C_4$-$C_{10}$heterocycloalkenyl and $C_2$-$C_{10}$heterocycloalkyl, wherein $C_1$-$C_6$alkyl, $C_2$-$C_6$alkenyl, $C_3$-$C_{10}$cycloalkyl, $C_1$-$C_6$heteroalkyl, $C_2$-$C_6$heteroalkenyl, $C_4$-$C_{10}$heterocycloalkenyl and $C_2$-$C_{10}$heterocycloalkyl are optionally substituted with at least one $R_1$; or
Y and Z together with the carbon atom to which they are attached form a $C_3$-$C_{10}$cycloalkyl, $C_2$-$C_{10}$heterocycloalkyl, $C_4$-$C_{10}$heterocycloalkenyl, aryl, or heteroaryl, wherein $C_3$-$C_{10}$cycloalkyl, $C_2$-$C_{10}$heterocycloalkyl, $C_4$-$C_{10}$heterocycloalkenyl, aryl, or heteroaryl, are optionally substituted with at least one X;

wherein when Y and Z together with the carbon atom to which they are attached form a nitrogen atom-containing C$_2$-C$_{10}$heterocycloalkyl or C$_4$-C$_{10}$heterocycloalkenyl, the nitrogen atom of the C$_2$-C$_{10}$heterocycloalkyl or C$_4$-C$_{10}$heterocycloalkenyl is optionally substituted with W and the carbon atoms of the C$_2$-C$_{10}$heterocycloalkyl or C$_4$-C$_{10}$heterocycloalkenyl are optionally substituted with at least one X;

W is selected from J, C(=O)-J, C(=O)O-J, C(=O)NR$_2$-J, C(=NR$_2$)-J, —C(=NR$_2$)NR$_2$-J, C(=N—OR$_3$)-J, C(=S)-J, S(=O)$_v$-J, S(=O)$_v$O-J;

X is F, Cl, Br, I, —CN, —NO$_2$, —OR$_3$, —N(R$_2$)$_2$, —SR$_2$, —C$_1$-C$_6$alkyl, —C(=O)R$_2$, —OC(=O)R$_2$, —NR$_2$C(=O)R$_2$, —NR$_2$C(=O)N(R$_2$)$_2$, —C(=O)N(R$_2$)$_2$, —C(=NR$_2$)N(R$_2$)$_2$, —C(=N—OR$_2$)N(R$_2$)$_2$, —C(=S)R$_2$, —S(=O)$_v$R$_2$, —OS(=O)$_v$R$_2$, —NR$_2$C(=O)OR$_2$, —NR$_2$S(=O)$_v$R$_2$;

J is —C$_1$-C$_6$alkyl, C$_3$-C$_6$cycloalkyl, —C$_2$-C$_6$alkene, C$_2$-C$_6$heterocycloalkyl, aryl, or heteroaryl optionally substituted with at least one R$_1$;

v is 1 or 2;

R$_b$ is NH$_2$, OH, OSO$_3$H or NHSO$_3$H;

R$_1$ is selected from F, Cl, Br, I, —CN, —NO$_2$, —SR$_2$, —OR$_3$, C$_1$-C$_6$alkyl, C$_1$-C$_6$haloalkyl, C$_1$-C$_6$hydroxyalkyl, —OC$_1$-C$_6$haloalkyl, C$_1$-C$_6$heteroalkyl, C$_3$-C$_6$cycloalkyl, C$_2$-C$_6$heterocycloalkyl, phenyl, —NR$_2$S(=O)$_2$R$_2$, —S(=O)$_2$N(R$_2$)$_2$, —C(=O)CF$_3$, —C(=O)NR$_2$S(=O)$_2$R$_2$, —S(=O)$_2$NR$_2$C(=O)R$_2$, —N(R$_2$)$_2$, wherein optionally the two R$_2$ groups of N(R$_2$)$_2$ and the nitrogen atom to which they are attached form a C$_2$-C$_6$ heterocycloalkyl ring, —NR$_2$C(=O)R$_2$, —NR$_2$C(=O)N(R$_2$)$_2$, —CO$_2$R$_2$, —C(=O)R$_2$, —OC(=O)R$_2$, —C(=O)N(R$_2$)$_2$, —OS(=O)$_2$R$_2$, —OS(=O)$_2$OR$_2$, —S(=O)R$_2$, —S(=O)$_2$R$_2$, —SO$_3$H, and at least one amino acid fragment;

R$_2$ is H, C$_1$-C$_6$alkyl, C$_1$-C$_6$haloalkyl, C$_1$-C$_6$hydroxyalkyl, or C$_3$-C$_6$cycloalkyl;

R$_3$ is H, methyl, ethyl, n-propyl, iso-propyl, n-butyl, iso-butyl, tert-butyl, or SO$_3$H;

R$_4$ is H or OH; or a pharmaceutically acceptable salt, solvate, or tautomeric form thereof.

In some embodiments, T is a bond. In other embodiments, T is C$_1$-C$_6$alkylene. In further embodiments, C$_1$-C$_6$alkylene is CH$_2$. In another embodiment, Y is C$_1$-C$_6$alkyl or C$_2$-C$_6$alkene. In one embodiment, C$_1$-C$_6$alkyl or C$_2$-C$_6$alkene is substituted with —C(=O)R$_2$ or —CO$_2$R$_2$. In a further embodiment, R$_2$ is H. In one embodiment, Z is C$_1$-C$_6$alkyl. In one embodiment, C$_1$-C$_6$alkyl is substituted with —C(=O)R$_2$, —OC(=O)R$_2$, —NR$_2$C(=O)R$_2$, or —C(=O)N(R$_2$)$_2$. In one embodiment, C$_1$-C$_6$alkyl is substituted with —NR$_2$C(=O)R$_2$. In one embodiment, each R$_2$ is H. In one embodiment, R$_2$ is C$_1$-C$_6$alkyl. In another embodiment, C$_1$-C$_6$alkyl is selected from methyl, ethyl, n-propyl, iso-propyl, n-butyl, iso-butyl, or tert-butyl. In one embodiment, R$_2$ is C$_1$-C$_6$hydroxyalkyl.

In one embodiment, Y and Z together with the carbon atom to which they are attached form a nitrogen atom-containing C$_2$-C$_{10}$heterocycloalkyl. In another embodiment, the nitrogen atom-containing C$_2$-C$_{10}$heterocycloalkyl is selected from:

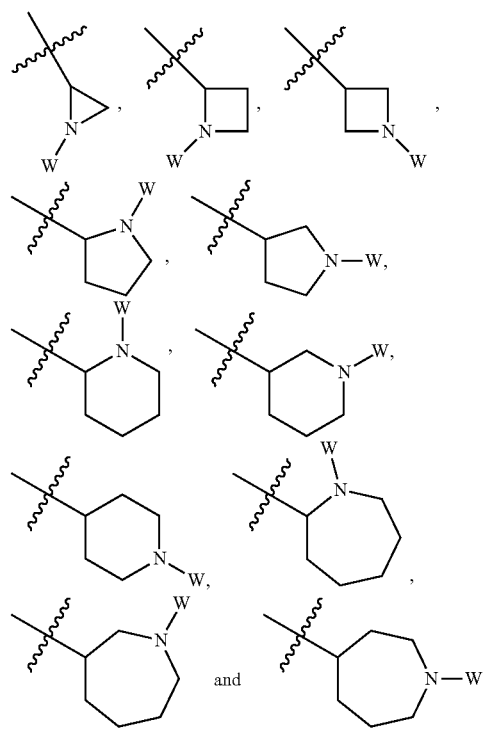

In yet another embodiment, is a compound of Formula (IIIC) or (IIID) wherein the nitrogen atom-containing C$_2$-C$_{10}$heterocycloalkyl is

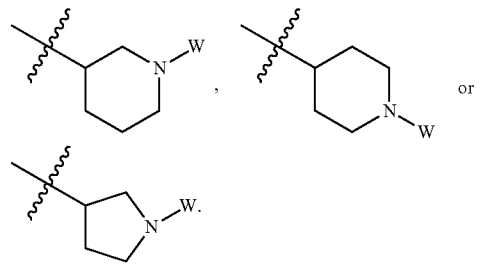

In a further embodiment,

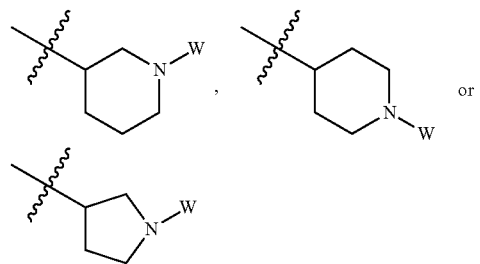

is substituted with at least one X. In yet a further embodiment, X is selected from F, Cl, Br, I, —CN, —OR$_3$, and NO$_2$. In one embodiment, X is —OH or —OSO$_3$H. In another embodiment, W is selected from J, C(=O)-J, C(=O)O-J, and C(=O)NR$_2$-J. In yet another embodiment, W is C(=O)-J. In a further embodiment, J is C$_1$-C$_6$alkyl. In yet a further embodiment, C$_1$-C$_6$alkyl is methyl, ethyl, n-propyl, iso-propyl, n-butyl, iso-butyl, and tert-butyl. In one embodiment, $C_1$-$C_6$alkyl is substituted with one $R_1$. In another embodiment, $C_1$-$C_6$alkyl is substituted with two $R_1$. In yet another embodiment, $R_1$ is selected from F, Cl, Br, I, —CN, $NO_2$, —$OR_3$, and at least one amino acid fragment.

In a further embodiment, W is J. In yet a further embodiment, J is $C_1$-$C_6$alkyl. In one embodiment, $C_1$-$C_6$alkyl is methyl, ethyl, n-propyl, iso-propyl, n-butyl, iso-butyl, and tert-butyl. In another embodiment, $C_1$-$C_6$alkyl is substituted with one $R_1$. In yet another embodiment, $C_1$-$C_6$alkyl is substituted with two $R_1$. In a further embodiment, $R_1$ is selected from F, Cl, Br, I, —CN, $NO_2$, and $OR_3$. In yet a further embodiment, $R_1$ is at least one amino acid fragment. In one embodiment, the at least one amino acid fragment is a cysteine or glutathione fragment. In another embodiment, one $R_1$ is an amino fragment and the other $R_1$ is selected from F, Cl, Br, I, —CN, $NO_2$, —OH, and —$OSO_3H$. In yet another embodiment, the at least one amino acid fragment is a di-peptide fragment. In a further embodiment, the at least one amino acid fragment is a tri-peptide fragment. In yet a further embodiment, the di-peptide fragment is a fragment of Cys-Gly. In one embodiment, J is $C_2$-$C_6$alkene. In another embodiment, $C_2$-$C_6$alkene is $C_2H_3$. In one embodiment, $C_2$-$C_6$alkene is substituted with at least one $R_1$ selected from F, Cl, Br, I, —CN, $NO_2$, OH, and —$OSO_3H$. In one embodiment, J is $C_2$-$C_6$heterocycloalkyl. In another embodiment $C_2$-$C_6$heterocycloalkyl is an epoxide. In a further embodiment, is a compound of Formula (I) wherein $R_1$ is selected from —$NR_2S(=O)_2R_2$, —$S(=O)_2N(R_2)_2$, —$C(O)NR_2S(=O)_2R_2$, —$S(=O)_2NR_2C(=O)R_2$, —$OS(=O)_2R_2$, —$OS(=O)_2OR_2$, —$S(=O)R_2$, or —$S(=O)_2R_2$. In one embodiment, $R_1$ is —$S(=O)_2R_2$. In another embodiment, $R_2$ is $C_1$-$C_6$haloalkyl. In a further embodiment, $C_1$-$C_6$haloalkyl is $CF_3$.

In a further embodiment is a compound having the structure:

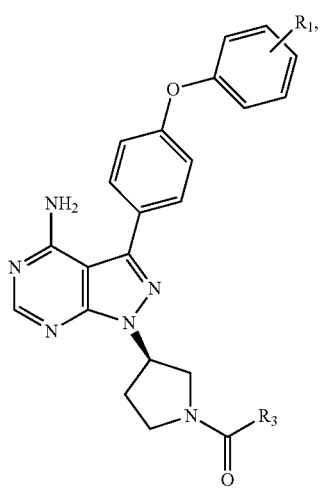

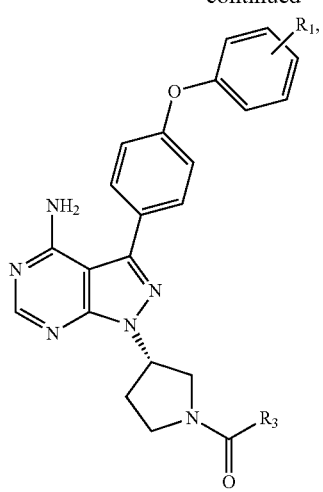

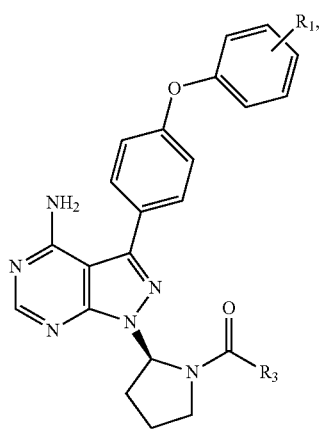

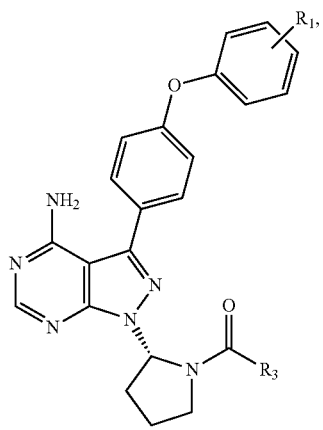

69
-continued
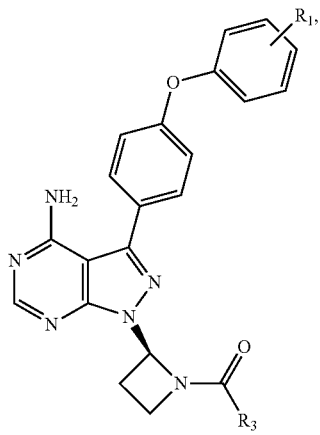
70
-continued
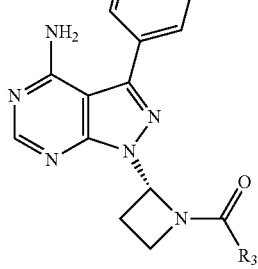
or a pharmaceutically acceptable salt, solvate, or metabolite thereof wherein the following compounds, having different substituents (for e.g., $R_1$ and $R_3$) are listed in the table below:
| Cmpd # | $R_3$ | $R_1$ | Cmpd # | $R_3$ | $R_1$ |
|---|---|---|---|---|---|
| 196 | ~~~Cl | H | 201 | ~~~Cl | 4-OH |
| 197 | ~~~Cl | 3-OH | 202 | ~~~Cl | 2-OH |
| 198 | ~~~N(CH3)2 | 4-OH | 203 | ~~~N(CH3)2 | 3-OH |
| 199 | ~~~N(CH3)2 | 2-OH | 204 | ~~~N(CH3)2 | 3,4-dihydroxy |
| 200 | ~~~NHCH3 | H | 205 | ~~~NHCH3 | 4-OH |
| 206 | ~~~NHCH3 | 3-OH | 219 | ~~~NHCH3 | 2-OH |

-continued

| Cmpd # | R₃ | R₁ | Cmpd # | R₃ | R₁ |
|---|---|---|---|---|---|
| 207 | epoxide-CH₂-N(CH₃)₂ | 3-OH | 220 | CH=CH-CH₂-NHCH₃ (with gem-dimethyl) | 3,4-dihydroxy |
| 208 | epoxide-CH₂-N(CH₃)₂ | H | 221 | epoxide-CH₂-N(CH₃)₂ | 4-OH |
| 209 | epoxide-CH₂-N(CH₃)₂ | 2-OH | 222 | epoxide-CH₂-N(CH₃)₂ | 3,4-dihydroxy |
| 210 | epoxide-CH₂-NH(CH₃) | H | 223 | epoxide-CH₂-NH(CH₃) | 4-OH |
| 211 | epoxide-CH₂-NH(CH₃) | 3-OH | 224 | epoxide-CH₂-NH(CH₃) | 2-OH |
| 212 | CH(OH)-CH(OH)-CH₂-N(CH₃)₂ | 3-OH | 225 | epoxide-CH₂-NH(CH₃) | 3,4-dihydroxy |
| 213 | CH(OH)-CH(OH)-CH₂-N(CH₃)₂ | H | 226 | CH(OH)-CH(OH)-CH₂-N(CH₃)₂ | 4-OH |
| 214 | CH(OH)-CH(OH)-CH₂-N(CH₃)₂ | 2-OH | 227 | CH(OH)-CH(OH)-CH₂-N(CH₃)₂ | 3,4-dihydroxy |
| 215 | CH(OH)-CH₂Cl | H | 228 | CH(OH)-CH₂Cl | 4-OH |
| 216 | CH(OH)-CH₂Cl | 3-OH | 229 | CH(OH)-CH₂Cl | 2-OH |

-continued

| Cmpd # | R₃ | R₁ | Cmpd # | R₃ | R₁ |
|---|---|---|---|---|---|
| 217 | CH=CH-CH₂-NH₂ | 3-OH | 230 | CH(OH)-CH₂-Cl | 3,4-dihydroxy |
| 218 | CH=CH-CH₂-NH₂ | 4-OH | 231 | CH(OH)-CH(OH)-CH₂-NH(CH₃) | H |
| 232 | CH=CH-CH₂-NH₂ | H | 248 | CH=CH-CH₂-NH₂ | 3,4-dihydroxy |
| 233 | CH=CH-CH₂-NH₂ | 2-OH | 249 | epoxide-CH₂-NH₂ | 4-OH |
| 234 | epoxide-CH₂-NH₂ | H | 250 | epoxide-CH₂-NH₂ | 3,4-dihydroxy |
| 235 | epoxide-CH₂-NH₂ | 3-OH | 251 | CH(OH)-CH(OH)-CH₂-NH₂ | 3,4-dihydroxy |
| 236 | CH(OH)-CH(OH)-CH₂-NH₂ | H | 252 | CH(OH)-CH(OH)-CH₂-NH₂ | 4-OH |
| 237 | CH(OH)-CH(OH)-CH₂-NH₂ | 2-OH | 253 | CH=CH-CH₂-N(CH₃)₂ | 3-OH |
| 238 | CH=CH-CH₂-N(CH₃)₂ | H | 254 | CH=CH-CH₂-N(CH₃)₂ | 4-OH |
| 239 | CH=CH-CH₂-N(CH₃)₂ | 2-OH | 255 | CH=CH-CH₂-N(CH₃)₂ | 3,4-dihydroxy |
| 240 | CH=CH-CH₂-NH(CH₃) | H | 256 | CH=CH-CH₂-NH(CH₃) | 4-OH |
| 241 | CH=CH-CH₂-NH(CH₃) | 3-OH | 257 | CH=CH-CH₂-NH(CH₃) | 3,4-dihydroxy |

-continued

| Cmpd # | R₃ | R₁ | Cmpd # | R₃ | R₁ |
|---|---|---|---|---|---|
| 242 | CH₂-CH=CH-CH₂-NH-CH₃ (cis) | 2-OH | 258 | CH₂-CH=CH-CH₂-NH₂ (cis) | 3,4-dihydroxy |
| 243 | CH₂-CH=CH-CH₂-NH₂ | 3-OH | 259 | CH₂-CH=CH-CH₂-NH₂ | 4-OH |
| 244 | CH₂-CH=CH-CH₂-NH₂ (cis) | 2-OH | 260 | CH₂-CH=CH-CH₂-NH₂ (cis) | H |
| 245 | CH₂-CHCl-CH₂Cl | 3-OH | 261 | CH₂-CHCl-CH₂Cl | 3,4-dihydroxy |
| 246 | CH₂-CHCl-CH₂Cl | H | 262 | CH₂-CHCl-CH₂Cl | 4-OH |
| 247 | CH₂-CHCl-CH₂Cl | 2-OH | 263 | CH₂-CHCl-CH₃ | 3,4-dihydroxy |
| 264 | CH₂-CHCl-CH₃ | H | 283 | CH₂-CHCl-CH₃ | 4-OH |
| 265 | CH₂-CHCl-CH₃ | 3-OH | 284 | CH₂-CHCl-CH₃ | 2-OH |
| 266 | CH₂-CHCl-CH₂OH | H | 285 | CH₂-CHCl-CH₂OH | 4-OH |
| 267 | CH₂-CHCl-CH₂OH | 3-OH | 286 | CH₂-CHCl-CH₂OH | 3,4-dihydroxy |
| 268 | CH₂-CHCl-CH₂OH | 2-OH | 287 | CH₂-CH₂-Cl | 3,4-dihydroxy |
| 269 | CH₂-CH₂-Cl | H | 288 | CH₂-CH₂-Cl | 4-OH |
| 270 | CH₂-CH₂-Cl | 3-OH | 289 | CH₂-CH₂-Cl | 2-OH |

-continued

| Cmpd # | R₃ | R₁ | Cmpd # | R₃ | R₁ |
|---|---|---|---|---|---|
| 271 | -CH(CH₃)-CH₂OH | H | 290 | -CH(CH₃)-CH₂OH | 4-OH |
| 272 | -CH(CH₃)-CH₂OH | 3-OH | 291 | -CH(CH₃)-CH₂OH | 3,4-dihydroxy |
| 273 | -CH(CH₃)-CH₂OH | 2-OH | 292 | -CH(CH₃)-CH₂Br | 3-OH |
| 274 | -CH(CH₃)-CH₂Br | H | 293 | -CH(CH₃)-CH₂Br | 4-OH |
| 275 | -CH(CH₃)-CH₂Br | 2-OH | 294 | -CH(CH₃)-CH₂Br | 3,4-dihydroxy |
| 276 | CH₃ | H | 295 | CH₃ | 4-OH |
| 277 | CH₃ | 3-OH | 296 | CH₃ | 3,4-dihydroxy |
| 278 | CH₃ | 2-OH | 297 | -CH(CH₃)-CH₂-CH₂Br | 3-OH |
| 279 | -CH(CH₃)-CH₂-CH₂Br | H | 298 | -CH(CH₃)-CH₂-CH₂Br | 3,4-dihydroxy |
| 280 | -CH(CH₃)-CH(OH)-CH₂Br | 3-OH | 299 | -CH(CH₃)-CH₂-CH₂Br | 4-OH |
| 281 | -CH(CH₃)-CH(OH)-CH₂Br | H | 300 | -CH(CH₃)-CH(OH)-CH₂Br | 4-OH |
| 282 | -CH(CH₃)-CH(OH)-CH₂Br | 2-OH | 301 | -CH(CH₃)-CH(OH)-CH₂Br | 3,4-dihydroxy |
| 302 | -CH(CH₃)-CH(Cl)-CH₂Br | H | 319 | -CH(CH₃)-CH(Cl)-CH₂Br | 4-OH |
| 303 | -CH(CH₃)-CH(Cl)-CH₂Br | 2-OH | 320 | -CH(CH₃)-CH(Cl)-CH₂Br | 3,4-dihydroxy |
| 304 | -CH(CH₃)-CH(Cl)-CH₂Br | 3-OH | 321 | -CH(CH₃)-CH(Br)-CH₂Br | 3,4-dihydroxy |

-continued

| Cmpd # | R₃ | R₁ | Cmpd # | R₃ | R₁ |
|---|---|---|---|---|---|
| 305 | CH(Br)CH₂Br | 2-OH | 322 | CH(Br)CH₂Br | 4-OH |
| 306 | CH(Br)CH₂Br | H | 323 | CH(Br)CH₃ | 3,4-dihydroxy |
| 307 | CH(Br)CH₃ | 2-OH | 324 | CH(Br)CH₃ | 3-OH |
| 308 | CH(Br)CH₃ | H | 325 | CH(Br)CH₃ | 4-OH |
| 309 | CH(Br)CH₂OH | H | 326 | CH(Br)CH₂OH | 4-OH |
| 310 | CH(Br)CH₂OH | 2-OH | 327 | CH(Br)CH₂OH | 3,4-dihydroxy |
| 311 | CH(Br)CH₂OH | 3-OH | 328 | CH₂Br | 3,4-dihydroxy |
| 312 | CH₂Br | 2-OH | 329 | CH₂Br | 4-OH |
| 313 | CH₂Br | H | 330 | CH₂CH₂OH | 3,4-dihydroxy |
| 314 | CH₂CH₂OH | H | 331 | CH₂CH₂OH | 4-OH |
| 315 | CH₂CH₂OH | 2-OH | 332 | CH₂CH₂OH | 3-OH |
| 316 | CH₂CH₃ | H | 333 | CH₂CH₃ | 4-OH |
| 317 | CH₂CH₃ | 2-OH | 334 | CH₂CH₃ | 3,4-dihydroxy |
| 318 | CH₂CH₃ | 3-OH | 335 | CH₂CH₂Cl | 3,4-dihydroxy |

-continued

| Cmpd # | R₃ | R₁ | Cmpd # | R₃ | R₁ |
|---|---|---|---|---|---|
| 336 | CH(OH)-CH(OH)-CH₂-NHCH₃ | H | 350 | CH(OH)-CH(OH)-CH₂-NHCH₃ | 2-OH |
| 337 | CH(OH)-CH(OH)-CH₂-NHCH₃ | 4-OH | 351 | CH(OH)-CH(OH)-CH₂-NHCH₃ | 3,4-dihydroxy |
| 338 | CH(OH)-CH(OH)-CH₂-NHCH₃ | 3-OH | 352 | CH(OH)-CH(OH)-CH₂-NH₂ | 3-OH |
| 339 | CH=CH-CH₂-N(CH₃)₂ | H | 353 | CH=CH-CH₂-N(CH₃)₂ | 3,4-dihydroxy |
| 340 | CH=CH-CH₂-N(CH₃)₂ | 4-OH | 354 | CH=CH-CH₂-N(CH₃)₂ | 2-OH |
| 341 | CH=CH-CH₂-N(CH₃)₂ | 3-OH | 355 | CH=CH-CH₂-NHCH₃ | 2-OH |
| 342 | CH=CH-CH₂-NHCH₃ | 3-OH | 356 | CH=CH-CH₂-NHCH₃ | 3,4-dihydroxy |
| 343 | CH=CH-CH₂-NHCH₃ | 4-OH | 357 | CH=CH-CH₂-NHCH₃ | H |
| 344 | CH=CH-CH₂-morpholinyl | 2-OH | 358 | CH=CH-CH₂-morpholinyl | 3-OH |
| 345 | CH=CH-CH₂-morpholinyl | 4-OH | 359 | CH=CH-CH₂-morpholinyl | 3,4-dihydroxy |
| 346 | CH=CH-CH₂-NH₂ | H | 360 | CH=CH-CH₂-NH₂ | 4-OH |
| 347 | CH=CH-CH₂-NH₂ | 2-OH | 361 | CH=CH-CH₂-NH₂ | 3,4-dihydroxy |
| 348 | CH=CH-CH₂-NH₂ | 3-OH | 362 | CH=CH-CH₂-N(CH₃)CH₂CH₂OH | 4-OH |

-continued
| Cmpd # | R₃ | R₁ | Cmpd # | R₃ | R₁ |
|---|---|---|---|---|---|
| 349 | 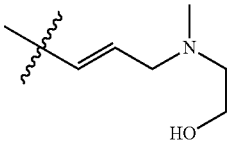 [SMILES: */C=C/CN(C)CCO] | 2-OH | 363 | 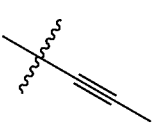 | 3,4-dihydroxy |
| 364 | 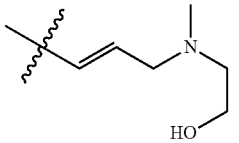 [SMILES: */C=C/CN(C)CCO] | 3-OH | 377 | 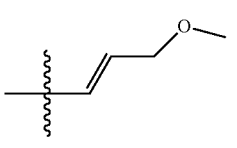 | 3,4-dihydroxy |
| 365 | 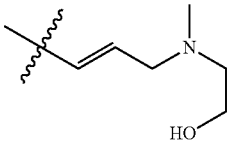 [SMILES: */C=C/CN(C)CCO] | 2-OH | 378 | 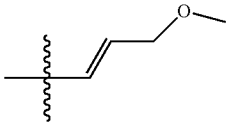 | 2-OH |
| 366 | 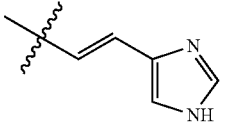 [SMILES: */C=C/c1c[nH]cn1] | 4-OH | 380 | CCH | 2-OH |
| 367 | CCH | 3-OH | 381 | CCH | 3,4-dihydroxy |
| 368 | CCH | 4-OH | 382 | 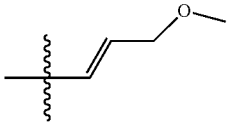 | 3,4-dihydroxy |
| 369 | 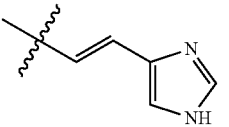 [SMILES: */C=C/c1c[nH]cn1] | 2-OH | 383 | 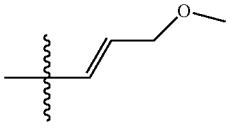 [SMILES: */C=C/COC] | 4-OH |
| 370 | 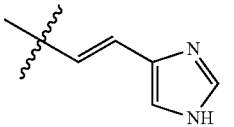 [SMILES: */C=C/c1c[nH]cn1] | 3-OH | 384 | 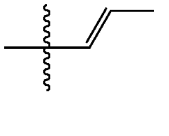 | 3,4-dihydroxy |
| 371 | 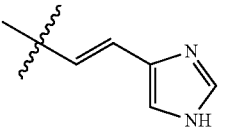 [SMILES: */C=C/c1c[nH]cn1] | 3-OH | 385 | 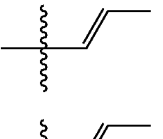 | 4-OH |
| 372 | 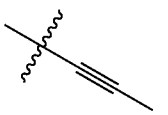 [SMILES: *C#CC] | 2-OH | 386 | 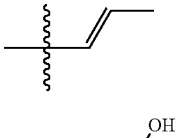 | 2-OH |
| 373 | 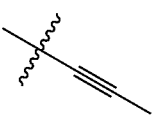 [SMILES: *C#CC] | 3-OH | 387 | 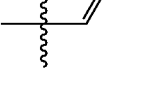 | 3,4-dihydroxy |
| 374 | 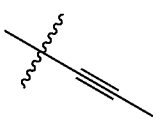 [SMILES: *C#CC] | 4-OH | 388 | 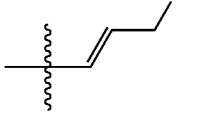 | 2-OH |

-continued
| Cmpd # | R₃ | R₁ | Cmpd # | R₃ | R₁ |
|---|---|---|---|---|---|
| 375 | ⸺CH=CH–CH₂OH | 3-OH | 389 | ⸺CH=CH–CH₂OH | 3,4-dihydroxy |
| 376 | ⸺CH=CH–CH₂OH | 4-OH | — | — | — |
In another embodiment is a compound selected from:
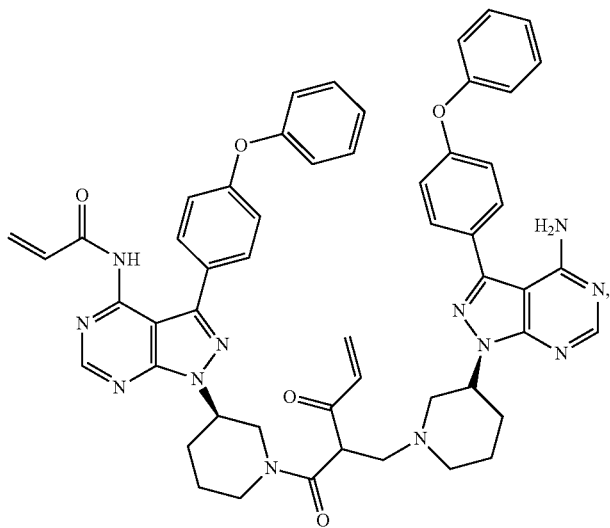
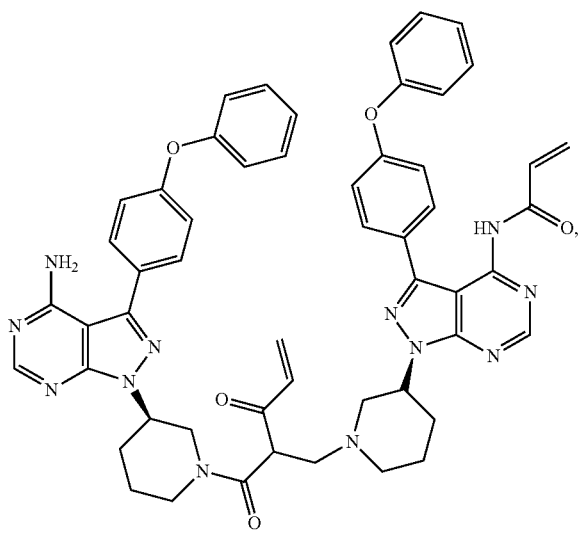

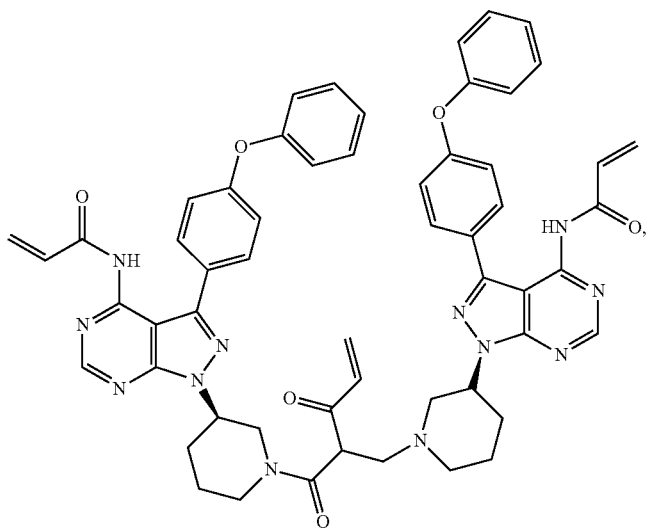
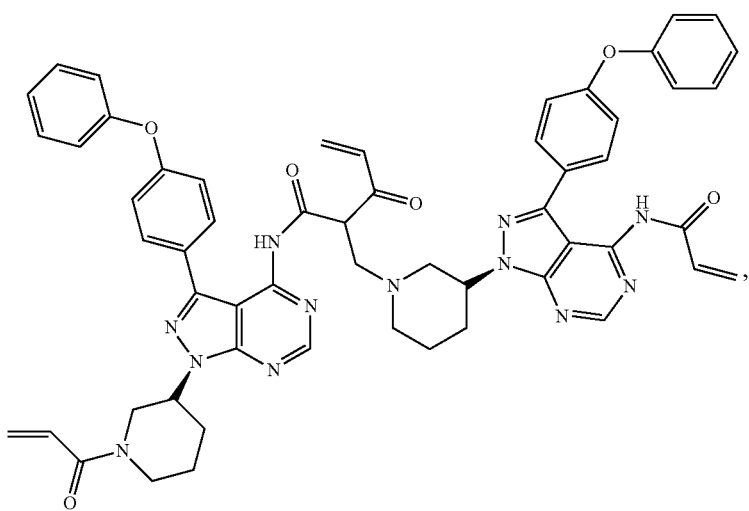
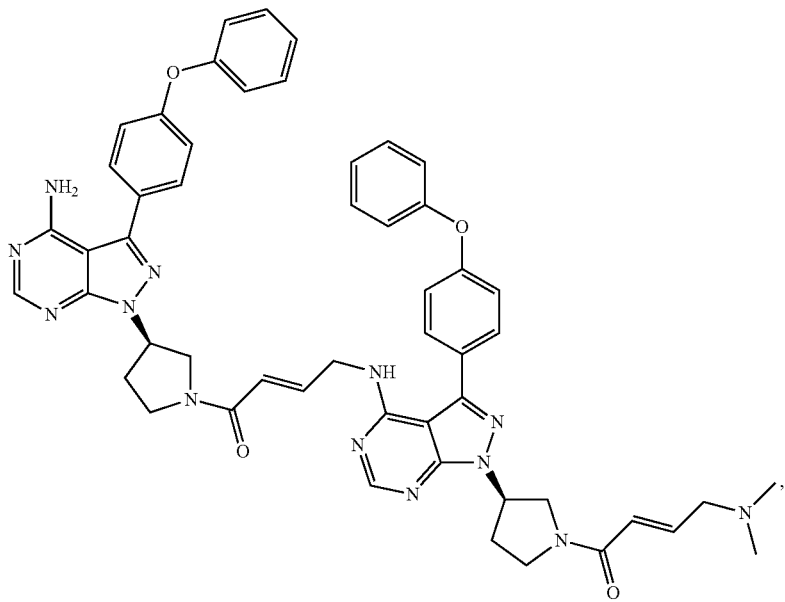

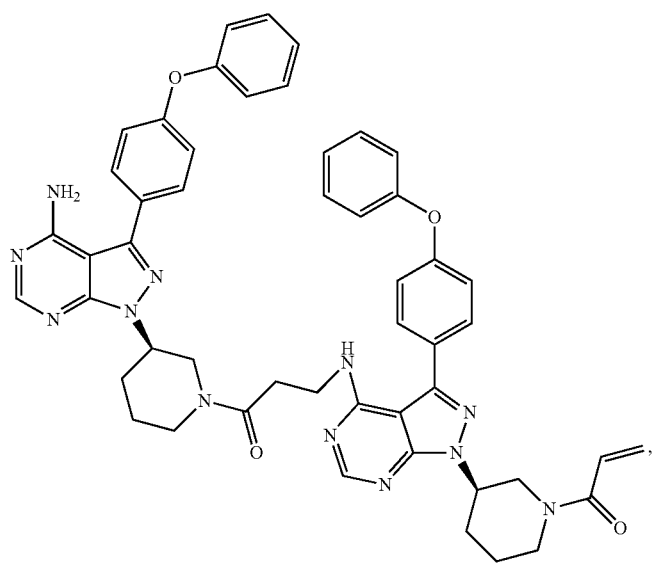
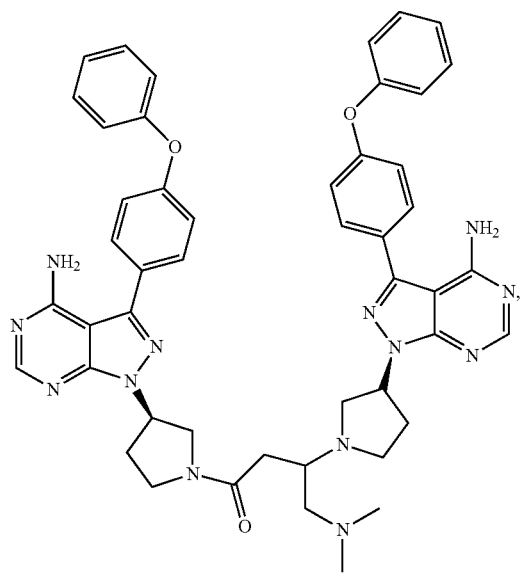

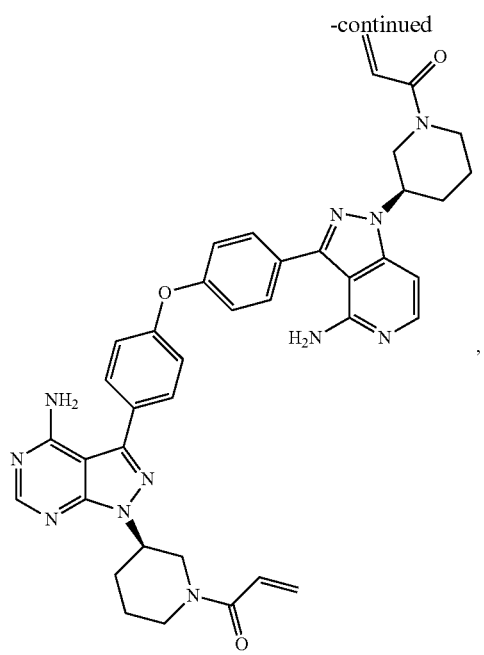
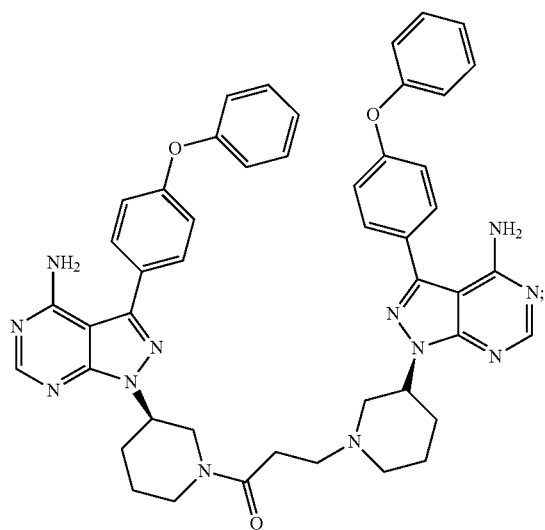
or a pharmaceutically acceptable salt, solvate, or metabolite thereof.

In another embodiment is a compound having the structure:
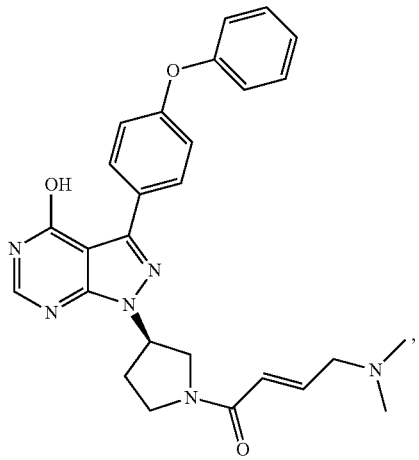
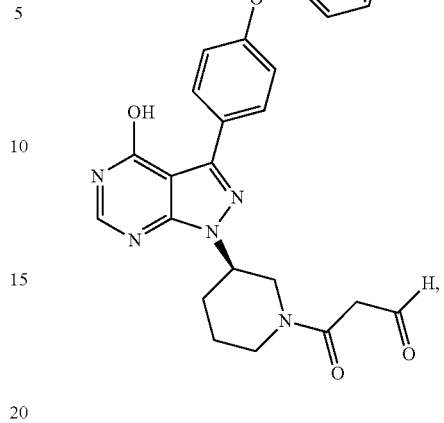
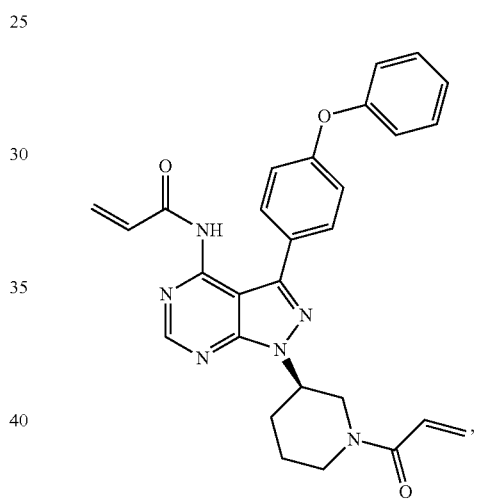
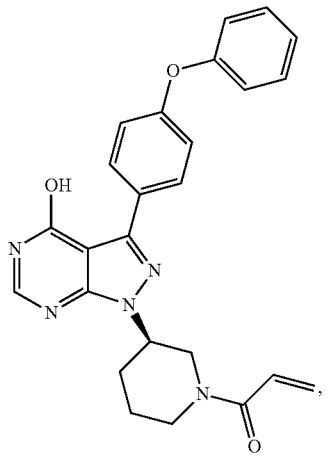
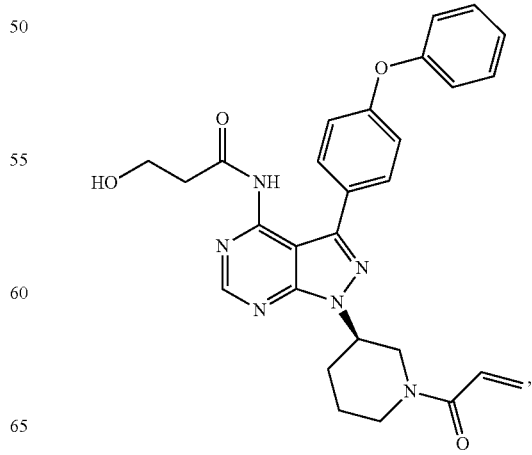

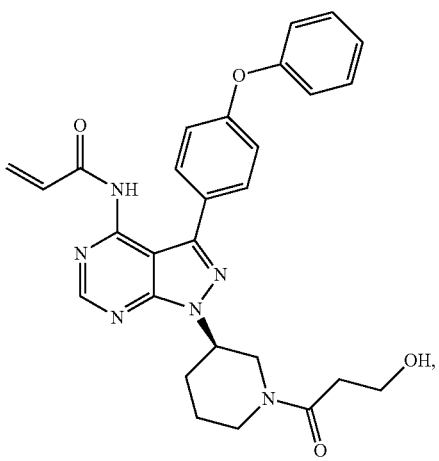 [SMILES: C=CC(=O)Nc1ncnc2c1c(-c1ccc(Oc3ccccc3)cc1)nn2[C@@H]1CCCN(C(=O)CCO)C1]

or a pharmaceutically acceptable salt, solvate, or metabolite thereof.

Also described herein is a compound having the structure:

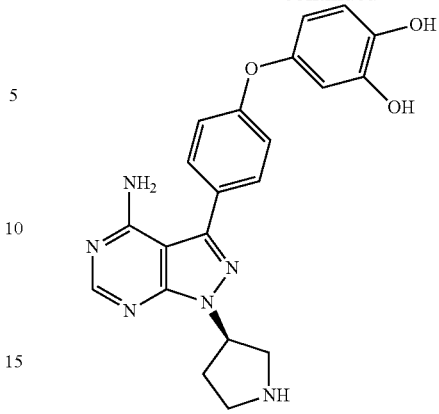

or a pharmaceutically acceptable salt, solvate, or metabolite thereof.

In one aspect, provided herein is a compound selected from among: 1-(3-(4-amino-3-(4-(3,4-dihydroxyphenoxy)phenyl)-6-hydroxy-1H-pyrazolo[3,4-d]pyrimidin-1-yl)piperidin-1-yl)propan-1-one, 1-(3-(4-amino-6-hydroxy-3-(4-(4-hydroxyphenoxy)phenyl)-1H-pyrazolo[3,4-d]pyrimidin-1-yl)piperidin-1-yl)-3-hydroxypropan-1-one, 4-(4-(4-amino-1-(1-(1-hydroxypropyl)piperidin-3-yl)-1H-pyrazolo[3,4-d]pyrimidin-3-yl)phenoxy)benzene-1,2-diol, 1-(3-(4-amino-3-(4-(3,4-dihydroxyphenoxy)phenyl)-1H-pyrazolo[3,4-d]pyrimidin-1-yl)piperidin-1-yl)-3-hydroxypropan-1-one, 4-(4-amino-3-(4-(4-hydroxyphenoxy)phenyl)-1H-pyrazolo[3,4-d]pyrimidin-1-yl)-5-propionamidopentanoic acid, 1-(3-(4-amino-3-(4-(4-hydroxyphenoxy)phenyl)-1H-pyrazolo[3,4-d]pyrimidin-1-yl)piperidin-1-yl)-3-hydroxypropan-1-one, 1-(3-(4-amino-6-hydroxy-3-(4-(4-hydroxyphenoxy)phenyl)-1H-pyrazolo[3,4-d]pyrimidin-1-yl)piperidin-1-yl)propan-1-one, 1-(3-(4-amino-3-(4-(4-hydroxyphenoxy)phenyl)-1H-pyrazolo[3,4-d]pyrimidin-1-yl)piperidin-1-yl)-2,3-dihydroxypropan-1-one, 1-(3-(4-amino-3-(4-(4-hydroxyphenoxy)phenyl)-1H-pyrazolo[3,4-d]pyrimidin-1-yl)piperidin-1-yl)-3-hydroxypropan-1-one, 1-(3-(4-amino-3-(4-(4-hydroxyphenoxy)phenyl)-1H-pyrazolo[3,4-d]pyrimidin-1-yl)piperidin-1-yl)propane-1,3-diol, 1-(3-(4-amino-6-hydroxy-3-(4-(4-hydroxyphenoxy)phenyl)-1H-pyrazolo[3,4-d]pyrimidin-1-yl)piperidin-1-yl)prop-2-en-1-one, N-(2-(4-amino-3-(4-(4-hydroxyphenoxy)phenyl)-1H-pyrazolo[3,4-d]pyrimidin-1-yl)-5-oxopentyl)propionamide, 2-(2-amino-3-(3-(4-amino-3-(4-phenoxyphenyl)-1H-pyrazolo[3,4-d]pyrimidin-1-yl)piperidin-1-yl)-3-hydroxypropylthio)propanamido)acetic acid, 2-amino-3-(3-(3-(4-amino-3-(4-phenoxyphenyl)-1H-pyrazolo[3,4-d]pyrimidin-1-yl)piperidin-1-yl)-3-oxopropylthio)propanoic acid, 1-(3-(4-amino-3-(4-phenoxyphenyl)-1H-pyrazolo[3,4-d]pyrimidin-1-yl)-5-hydroxypiperidin-1-yl)propan-1-one, 1-(3-(4-amino-3-(4-phenoxyphenyl)-1H-pyrazolo[3,4-d]pyrimidin-1-yl)-5-hydroxypiperidin-1-yl)-2,3-dihydroxypropan-1-one, N-(2-(4-amino-3-(4-phenoxyphenyl)-1H-pyrazolo[3,4-d]pyrimidin-1-yl)-5-oxopent-3-enyl)-3-hydroxypropanamide, 3-(3-(3-(4-amino-3-(4-phenoxyphenyl)-1H-pyrazolo[3,4-d]pyrimidin-1-yl)piperidin-1-yl)-3-oxopropylthio)-2-(carboxyamino) propanoic acid, 4-amino-3-(4-phenoxyphenyl)-1-(1-propionylpiperidin-3-yl)-1H-pyrazolo[3,4-d]pyrimidin-6(7H)-one, 4-(4-(1-(1-acryloylpiperidin-3-yl)-4-amino-1H-pyrazolo[3,4-d]pyrimidin-3-yl)phenoxy)phenyl hydrogen sulfate, and 1-(3-(4-amino-3-(4-(4-hydroxyphenoxy)phenyl)-1H-pyrazolo[3,4-d]pyrimidin-1-yl)piperidin-1-yl)prop-2-en-1-one; or a pharmaceutically acceptable salt, solvate or tautomeric form thereof.

In one embodiment is a compound selected from:
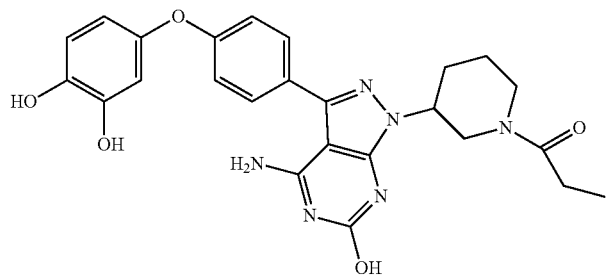
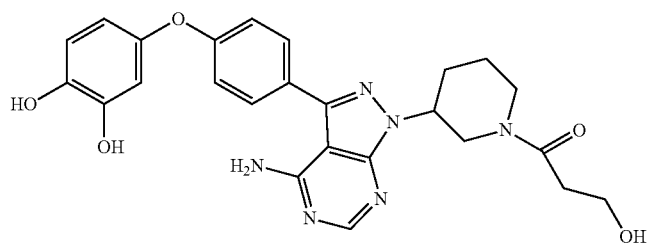
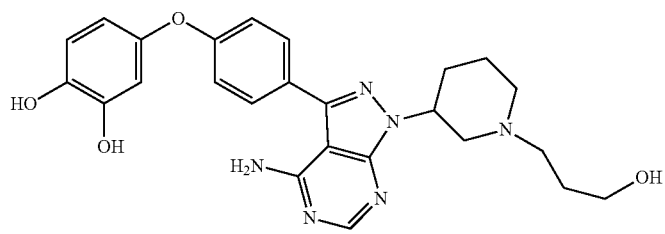
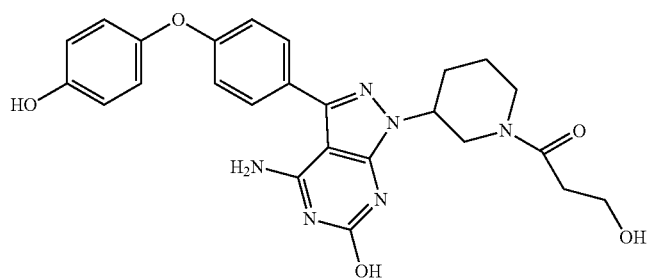
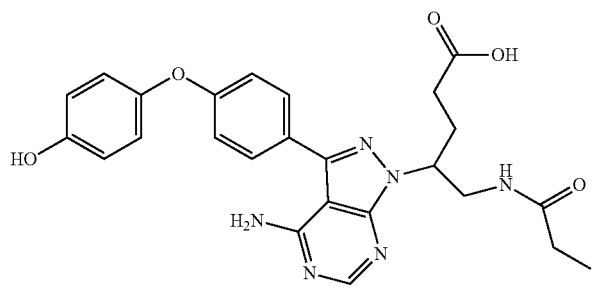
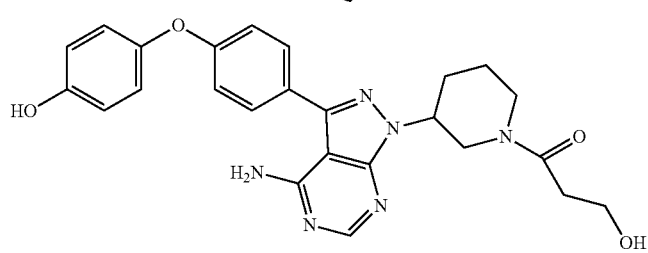

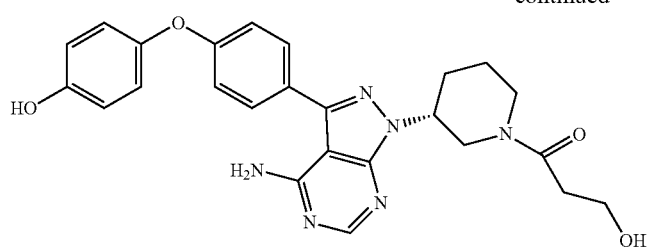
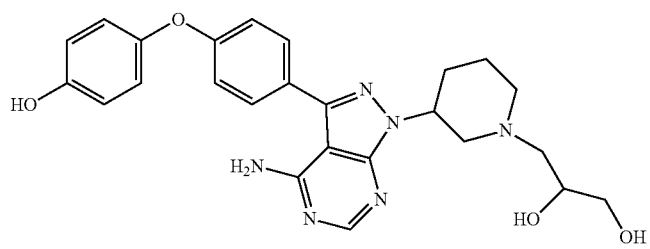
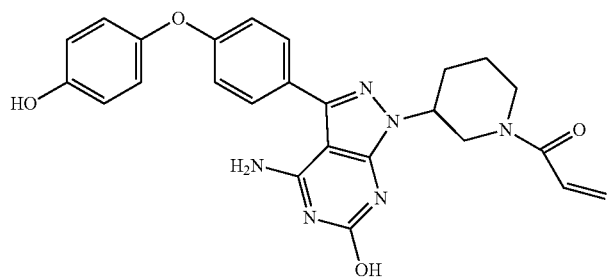
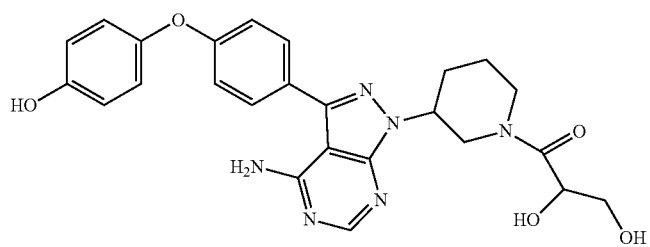
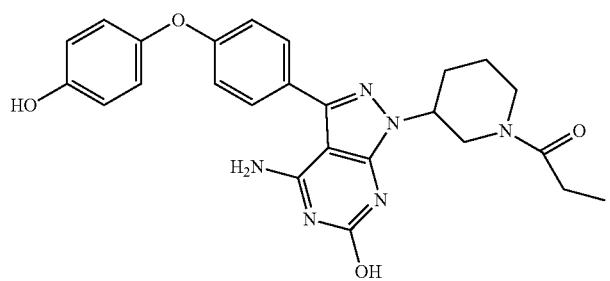
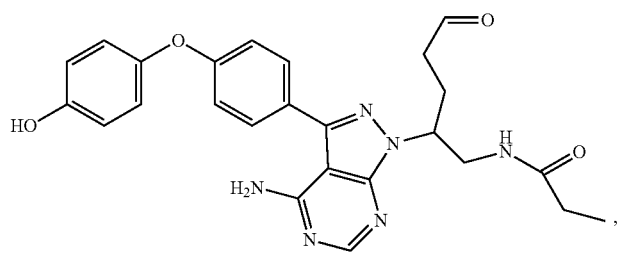

-continued
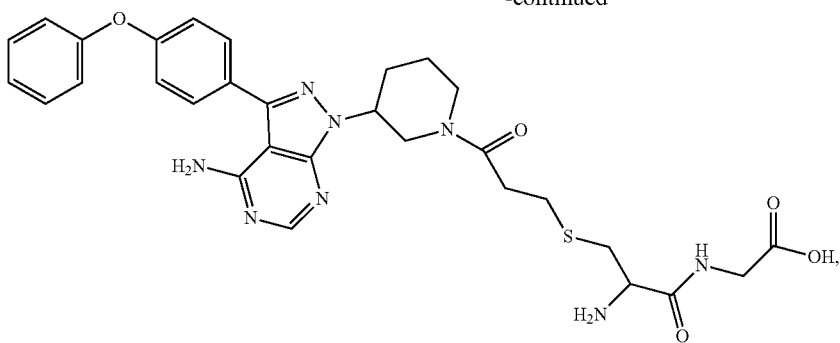
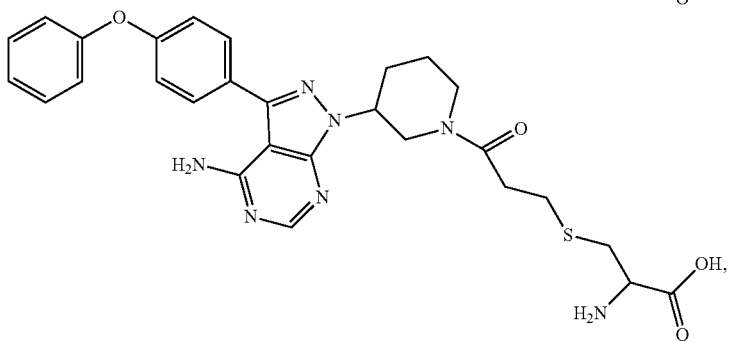
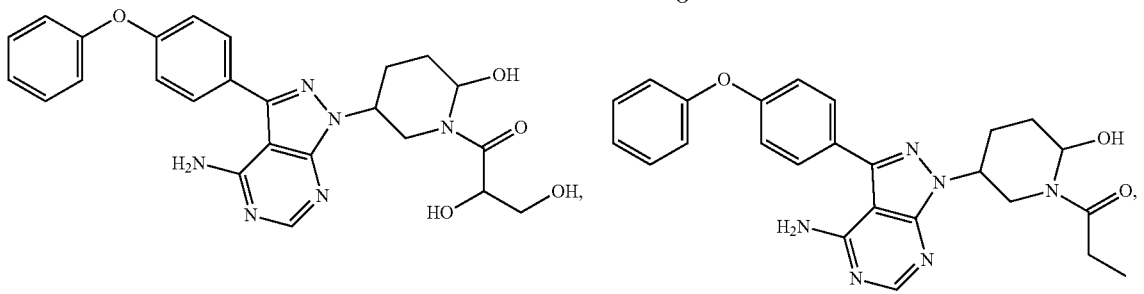
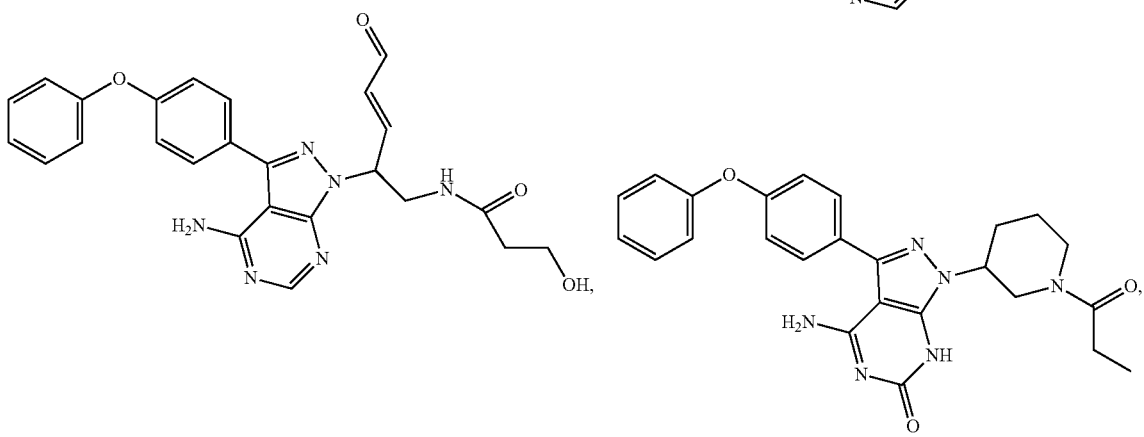
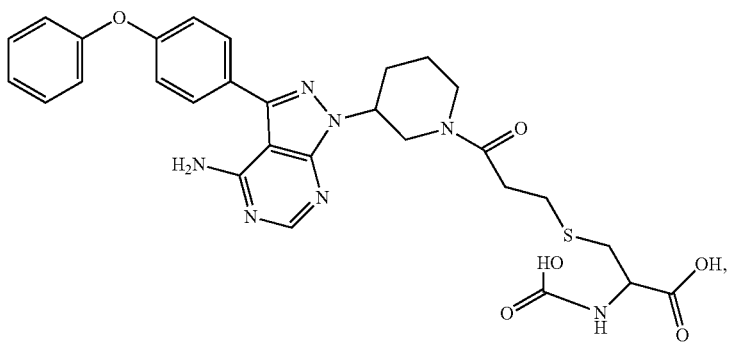

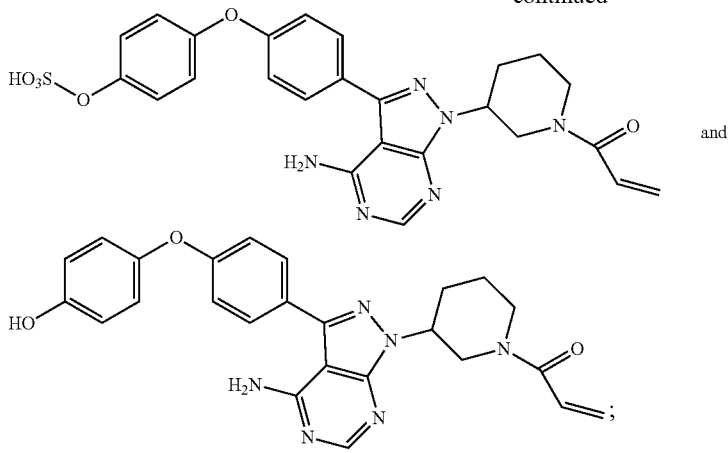

and

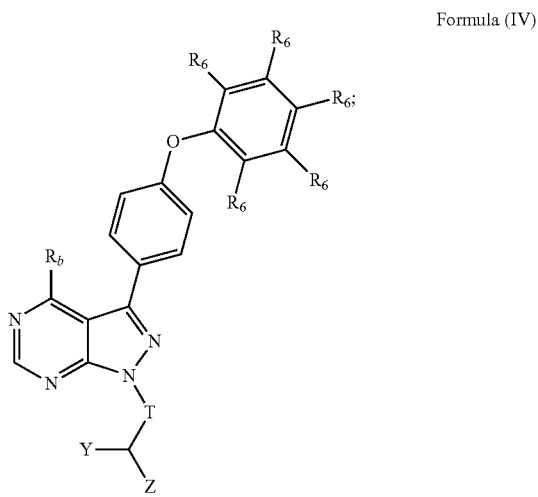

;

or a pharmaceutically acceptable salt, solvate, or tautomeric form thereof.

In a further embodiment is a compound of Formula (IV) having the structure:

Formula (IV)

wherein:
T is a bond, $C_1$-$C_6$alkylene, or $C_3$-$C_6$cycloalkylene;
Y and Z are each independently selected from H, $C_1$-$C_6$alkyl, $C_2$-$C_6$alkenyl, $C_3$-$C_{10}$cycloalkyl, $C_1$-$C_6$heteroalkyl, $C_2$-$C_6$heteroalkenyl, $C_4$-$C_{10}$heterocycloalkenyl and $C_2$-$C_{10}$heterocycloalkyl, wherein $C_1$-$C_6$alkyl, $C_2$-$C_6$alkenyl, $C_3$-$C_{10}$cycloalkyl, $C_1$-$C_6$heteroalkyl, $C_2$-$C_6$heteroalkenyl, $C_4$-$C_{10}$heterocycloalkenyl and $C_2$-$C_{10}$heterocycloalkyl are optionally substituted with at least one $R_1$; or
Y and Z together with the carbon atom to which they are attached form a $C_3$-$C_{10}$cycloalkyl, $C_2$-$C_{10}$heterocycloalkyl, $C_4$-$C_{10}$heterocycloalkenyl, aryl, or heteroaryl, wherein $C_3$-$C_{10}$cycloalkyl, $C_2$-$C_{10}$heterocycloalkyl, $C_4$-$C_{10}$heterocycloalkenyl, aryl, or heteroaryl, are optionally substituted with at least one X;
wherein when Y and Z together with the carbon atom to which they are attached form a nitrogen atom-containing $C_2$-$C_{10}$heterocycloalkyl or $C_4$-$C_{10}$heterocycloalkenyl, the nitrogen atom of the $C_2$-$C_{10}$heterocycloalkyl or $C_4$-$C_{10}$heterocycloalkenyl is optionally substituted with W and the carbon atoms of the $C_2$-$C_{10}$heterocycloalkyl or $C_4$-$C_{10}$heterocycloalkenyl are optionally substituted with at least one X;
W is selected from J, C(=O)-J, C(=O)O-J, C(=O)$NR_2$-J, C(=$NR_2$)-J, —C(=$NR_2$)$NR_2$-J, C(=N—$OR_3$)-J, C(=S)-J, S(=O)$_v$-J, S(=O)$_v$O-J;
X is F, Cl, Br, I, —CN, —$NO_2$, —$OR_3$, —N($R_2$)$_2$, —$SR_2$, —$C_1$-$C_6$alkyl, —C(=O)$R_2$, —OC(=O)$R_2$, —$NR_2$C(=O)$R_5$, —$NR_2$C(=O)N($R_2$)$_2$, —C(=O)N($R_2$)$_2$, —C(=$NR_2$)N($R_2$)$_2$, —C(=N—$OR_2$)N($R_2$)$_2$, —C(=S)$R_2$, —S(=O)$_v$$R_2$, —OS(=O)$_v$$R_2$, —$NR_2$C(=O)$OR_2$, —$NR_2$S(=O)$_v$$R_2$;
J is —$C_1$-$C_6$alkyl, $C_3$-$C_6$cycloalkyl, —$C_2$-$C_6$alkene, $C_2$-$C_6$heterocycloalkyl, aryl, or heteroaryl optionally substituted with at least one $R_1$;
v is 1 or 2;
$R_b$ is $NH_2$, OH, $OSO_3$H or $NHSO_3$H, halogen, —CN, —$NO_2$, —$SR_2$, optionally substituted $C_1$-$C_6$alkyl; N($R_2$)$_2$ or $NHR_7$;
$R_1$ is selected from F, Cl, Br, I, —CN, —$NO_2$, —$SR_2$, —$OR_3$, $C_1$-$C_6$alkyl, $C_1$-$C_6$haloalkyl, $C_1$-$C_6$hydroxyalkyl, —$OC_1$-$C_6$haloalkyl, $C_1$-$C_6$heteroalkyl, $C_3$-$C_6$cycloalkyl, $C_2$-$C_6$heterocycloalkyl, phenyl, —$NR_2$S(=O)$_2$$R_2$, —S(=O)$_2$N($R_2$)$_2$, —C(=O)$CF_3$, —C(=O)$NR_2$S(=O)$_2$$R_2$, —S(=O)$_2$$NR_2$C(=O)$R_2$, —N($R_2$)$_2$, wherein optionally the two $R_2$ groups of N($R_2$)$_2$ and the nitrogen atom to which they are attached form a $C_2$-$C_6$ heterocycloalkyl ring, —$NR_2$C(=O)$R_2$, —$NR_2$C(=O)$R_8$, —$NR_2$C(=O)N($R_2$)$_2$, —$CO_2$$R_2$, —C(=O)$R_2$, —OC(=O)$R_2$, —C(=O)N($R_2$)$_2$, —OS(=O)$_2$$R_2$, —OS(=O)$_2$$OR_2$, —S(=O)$R_2$, —S(=O)$_2$$R_2$, —$SO_3$H, and at least one amino acid fragment;
$R_2$ is H, $C_1$-$C_6$alkyl, $C_1$-$C_6$haloalkyl, $C_1$-$C_6$hydroxyalkyl, or $C_3$-$C_6$cycloalkyl;
$R_3$ is H, methyl, ethyl, n-propyl, iso-propyl, n-butyl, iso-butyl, tert-butyl, or $SO_3$H;
$R_6$ is selected from H, F, Cl, Br, I, —CN, —$NO_2$, —$SR_2$, —$OR_3$, $C_1$-$C_6$alkyl, $C_1$-$C_6$haloalkyl, $C_1$-$C_6$hydroxyalkyl, —$OC_1$-$C_6$haloalkyl, $C_1$-$C_6$heteroalkyl, $C_3$-$C_6$cycloalkyl, $C_2$-$C_6$heterocycloalkyl, phenyl, —$NR_2$S(=O)$_2$$R_2$, —S(=O)$_2$N($R_2$)$_2$, —C(=O)$CF_3$, —C(=O)$NR_2$S(=O)$_2$$R_2$, —S(=O)$_2$$NR_2$C(=O)$R_2$, —N($R_2$)$_2$, wherein optionally the two R$_2$ groups of N(R$_2$)$_2$ and the nitrogen atom to which they are attached form a C$_2$-C$_6$ heterocycloalkyl ring, —NR$_2$C(=O)R$_2$, —NR$_2$C(=O)N(R$_2$)$_2$, —CO$_2$R$_2$, —C(=O)R$_2$, —OC(=O)R$_2$, —C(=O)N(R$_2$)$_2$, —OS(=O)$_2$R$_2$, —OS(=O)$_2$OR$_2$, —S(=O)R$_2$, —S(=O)$_2$R$_2$, —SO$_3$H, and at least one amino acid fragment; wherein each R$_6$ cannot all be H;

R$_7$ is an amino protecting group;

R$_8$ is an optionally substituted C$_1$-C$_6$alkyl, an optionally substituted C$_2$-C$_6$alkenyl, an optionally substituted C$_2$-C$_6$alkynyl, or an optionally substituted C$_3$-C$_6$cycloalkyl; or a pharmaceutically acceptable salt, solvate, or metabolite thereof.

In one embodiment is the compound of Formula (IV) wherein Y and Z together with the carbon atom to which they are attached form a

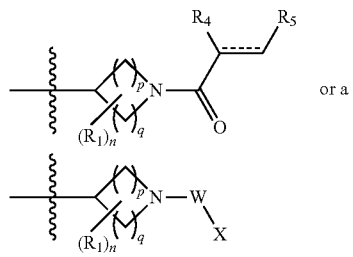

or a group;

/// is a single bond, a cis or trans-double bond, or a triple bond wherein R$_4$ is absent;

p is 0-6;

q is 0-6; wherein p+q is ≥1;

n is 0-4;

R$_4$ and R$_5$ are each independently selected from H, F, Cl, Br, I, —CN, —NO$_2$, —SR$_2$, —OR$_3$, optionally substituted C$_1$-C$_6$alkyl, C$_1$-C$_6$haloalkyl, C$_1$-C$_6$hydroxyalkyl, —OC$_1$-C$_6$haloalkyl, C$_1$-C$_6$heteroalkyl, optionally substituted C$_3$-C$_6$cycloalkyl, C$_2$-C$_6$heterocycloalkyl, phenyl, —OSO$_3$H, —NR$_2$S(=O)$_2$R$_2$, —S(=O)$_2$N(R$_2$)$_2$, —C(=O)CF$_3$, —C(=O)NR$_2$S(=O)$_2$R$_2$, —S(=O)$_2$NR$_2$C(=O)R$_2$, —N(R$_2$)$_2$, —NR$_2$C(=O)R$_2$, —CO$_2$R$_2$, —C(=O)R$_2$, —OC(=O)R$_2$, —C(=O)N(R$_2$)$_2$, —OS(=O)$_2$R$_2$, —OS(=O)$_2$OR$_2$, —S(=O)R$_2$, —S(=O)$_2$R$_2$, and at least one amino acid fragment; or optionally when /// is a single bond then R$_4$ and R$_5$ together with the carbon atoms to which they are attached form an epoxide; wherein when /// is a single bond then R$_4$ and R$_5$ are not both hydrogen; or a pharmaceutically acceptable salt, solvate or metabolite thereof.

In one embodiment is a compound of Formula (IV) wherein Y and Z together with the carbon atom to which they are attached form a

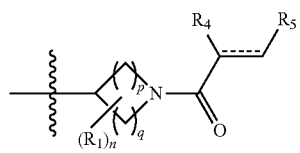

group.

In another embodiment is a compound of Formula (IV) wherein Y and Z together with the carbon atom to which they are attached form a

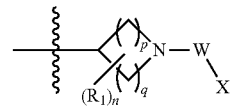

group.

In a further embodiment is a compound of Formula (IV) wherein W is C(=O)-J. In another embodiment, W is S(=O)$_v$-J.

In a further embodiment is a compound of Formula (IV) wherein J is an optionally substituted C$_2$-C$_6$alkene. In another embodiment, J is an optionally substituted C$_1$-C$_6$alkyl. In a further embodiment, C$_2$-C$_6$alkene is ethylene. In a further embodiment, ethylene is substituted with with C$_1$-C$_6$alkylN(R$_2$)$_2$; wherein R$_2$ is selected from H, C$_1$-C$_6$haloalkyl, C$_1$-C$_6$hydroxyalkyl, or C$_3$-C$_6$cycloalkyl.

In yet another embodiment is a compound of Formula (IV) wherein R$_6$ is OH. In one embodiment, OH is substituted at the 2-position. In another embodiment, OH is substituted at the 3-position. In a further embodiment, OH is substituted at the 4-position. In yet a further embodiment, OH is substituted at the 3 and 4-positions.

In yet another embodiment is a compound of Formula (IV) wherein R$_b$ is NHR$_7$ wherein R$_7$ is an amino protecting group. In one embodiment is a compound of Formula (IV) wherein the amino protecting group is selected from Fmoc, Boc, Cbz, Ac, trifluoroacetamide, Bn, trityl, benzylideneamine, Ts, or the H attached to the nitrogen atom of the primary amine is absent and R and the nitrogen atom to which it is attached form a phthalimide group; or a pharmaceutically acceptable salt, solvate, or metabolite thereof.

In a further embodiment is a compound of Formula (IV) wherein R$_b$ is N(R$_2$)$_2$. In one embodiment R$_2$ is selected from optionally substituted C$_1$-C$_6$alkyl or C$_1$-C$_6$haloalkyl. In another embodiment, R$_2$ is C$_1$-C$_6$haloalkyl.

Also described herein are irreversible inhibitors of Btk. Further described are irreversible inhibitors of Btk that form a covalent bond with a cysteine residue on Btk. Further described herein are irreversible inhibitors of other tyrosine kinases, wherein the other tyrosine kinases share homology with Btk by having a cysteine residue (including a Cys 481 residue) that can form a covalent bond with the irreversible inhibitor (such tyrosine kinases, are referred herein as "Btk tyrosine kinase cysteine homologs"). Also described herein are methods for synthesizing such irreversible inhibitors, methods for using such irreversible inhibitors in the treatment of diseases (including diseases wherein irreversible inhibition of Btk provides therapeutic benefit to a patient having the disease). Further described are pharmaceutical formulations that include an irreversible inhibitor of Btk.

Also described herein are irreversible inhibitors of tyrosine kinases that have an accessible cysteine residue near an active site of the tyrosine kinase (referred herein as "Accessible Cysteine Kinases" or ACKs). Also described herein are irreversible inhibitors of any of the aforementioned tyrosine kinases, in which the irreversible inhibitor includes a Michael acceptor moiety. Further described are such irreversible inhibitors in which the Michael acceptor moiety preferentially forms a covalent bond with the appropriate cysteine residue on the desired tyrosine kinase relative to forming a covalent bond with other biological molecules that contain an accessible SH moiety. Also described herein are methods for synthesizing such irreversible inhibitors, methods for using such irreversible inhibitors in the treatment of diseases (including diseases wherein irreversible inhibition of Btk provides therapeutic benefit to a patient having the disease). Further described are pharmaceutical formulations that include an irreversible inhibitor of Btk.

In one aspect is a compound of Formula (I) wherein Y and Z together with the carbon atom to which they are attached form a

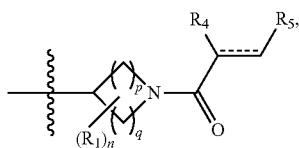

wherein ⫽ is a cis or trans-double bond. In one embodiment, is a compound of Formula (I) having the structure

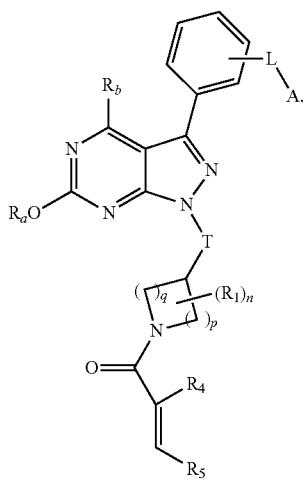

In another embodiment, the compound of Formula (I) forms a covalent bond with a cysteine residue of a Bruton's tyrosine kinase.

In another aspect are methods for modulating, including irreversibly inhibiting the activity of Btk or other tyrosine kinases, wherein the other tyrosine kinases share homology with Btk by having a cysteine residue (including a Cys 481 residue) that can form a covalent bond with at least one irreversible inhibitor described herein, in a mammal comprising administering to the mammal at least once an effective amount of at least one compound having the structure of any of Formula (I). In another aspect are methods for modulating, including including irreversibly inhibiting, the activity of Btk in a mammal comprising administering to the mammal at least once an effective amount of at least one compound having the structure of any of Formula (I). In another aspect are methods for treating Btk-dependent or Btk mediated conditions or diseases, comprising administering to the mammal at least once an effective amount of at least one compound having the structure of any of Formula (I).

In a further or alternative embodiment, the compound of Formula (I) having a Michael acceptor are irreversible inhibitors of Bruton's tyrosine kinase (Btk), while in still further or alternative embodiments, such irreversible inhibitors are selective for Btk. In even further or alternative embodiments, such inhibitors have an $IC_{50}$ below 10 microM in enzyme assay. In one embodiment, a Btk irreversible inhibitor has an $IC_{50}$ of less than 1 microM, and in another embodiment, less than 0.25 microM.

In further or alternative embodiment, the compound of Formula (I) is a selective irreversible inhibitor for Btk over Itk. In further or alternative embodiment, the compound of Formula (I) is a selective irreversible inhibitor for Btk over Lck. In further or alternative embodiment, the compound of Formula (I) is a selective irreversible inhibitor for Btk over ABL. In further or alternative embodiment, the compound of Formula (I) is a selective irreversible inhibitor for Btk over CMET. In further or alternative embodiment, the compound of Formula (I) is a selective irreversible inhibitor for Btk over EGFR. In further or alternative embodiment, the compound of Formula (I) is a selective irreversible inhibitor for Btk over Lyn.

In one embodiment, the irreversible Btk inhibitor compound selectively and irreversibly inhibits an activated form of its target tyrosine kinase (e.g., a phosphorylated form of the tyrosine kinase). For example, activated Btk is transphosphorylated at tyrosine 551. Thus, in these embodiments the irreversible Btk inhibitor inhibits the target kinase in cells only once the target kinase is activated by the signaling events.

Generally, an irreversible inhibitor compound used in the methods described herein is identified or characterized in an in vitro assay, e.g., an acellular biochemical assay or a cellular functional assay. Such assays are useful to determine an in vitro $IC_{50}$ for an irreversible inhibitor compound.

For example, in some embodiments, an acellular kinase assay is used to determine kinase activity after incubation of the kinase in the absence or presence of a range of concentrations of a candidate inhibitor compound. If the candidate compound is in fact an inhibitor, kinase activity will not be recovered by repeat washing with inhibitor-free medium. See, e.g., J. B. Smaill, et al. (1999), *J. Med. Chem.* 42(10): 1803-1815. Further, covalent complex formation between a Kinase and a candidate inhibitor is a useful indicator of inhibition of the Kinase that can be readily determined by a number of methods (e.g., mass spectrometry). For example, in some embodiments, some Kinase-inhibitor compounds form a covalent bond with the aforenoted cysteine residue (e.g., via a Michael reaction).

High throughput assays for many acellular biochemical assays (e.g., kinase assays) and cellular functional assays (e.g., calcium flux) are documented methodologies. In addition, high throughput screening systems are commercially available (see, e.g., Zymark Corp., Hopkinton, MA; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. Automated systems thereby allow the identification and characterization of a large number of compounds.

In some embodiments, the inhibitors described herein are used for the manufacture of a medicament for treating any of the foregoing conditions (e.g., autoimmune diseases, inflammatory diseases, allergy disorders, B-cell proliferative disorders, or thromboembolic disorders).

In some embodiments, the inhibitor compound used for the methods described herein inhibits a Kinase activity with an in vitro $IC_{50}$ of less than about 10 μM. (e.g., less than about 1 μM, less than about 0.5 μM, less than about 0.4 μM, less than about 0.3 μM, less than about 0.1, less than about 0.08 μM, less than about 0.06 μM, less than about 0.05 μM, less than about 0.04 μM, less than about 0.03 μM, less than about 0.02 μM, less than about 0.01, less than about 0.008 μM, less than about 0.006 μM, less than about 0.005 μM, less than about 0.004 μM, less than about 0.003 μM, less than about 0.002

µM, less than about 0.001, less than about 0.00099 µM, less than about 0.00098 µM, less than about 0.00097 µM, less than about 0.00096 µM, less than about 0.00095 µM, less than about 0.00094 µM, less than about 0.00093 µM, less than about 0.00092, or less than about 0.00090 µM).

In one embodiment, the inhibitor compound selectively inhibits an activated form of its target tyrosine kinase (e.g., a phosphorylated form of the tyrosine kinase). For example, activated Btk is transphosphorylated at tyrosine 551. Thus, in these embodiments the Btk inhibitor inhibits the target kinase in cells only once the target kinase is activated by the signaling events.

In further embodiments, the compounds of Formula (I) irreversibly inhibit Btk and are used to treat patients suffering from Bruton's tyrosine kinase-dependent or Bruton's tyrosine kinase mediated conditions or diseases, including, but not limited to, cancer, autoimmune and other inflammatory diseases.

Preparation of Compounds

Compounds of any of Formula (I), (IA), (II), (IIIA), (IIIB), (IIIC), (IIID), or (IV) or other pyrazolopyrimidine compounds described herein are optionally synthesized using standard synthetic techniques or using such methods known in combination with methods described herein. In additions, solvents, temperatures and other reaction conditions are presented herein for illustration only, and not to limit the scope of the methods and compositions described herein. As a further guide the following synthetic methods may also be utilized.

The reactions are optionally employed in a linear sequence to provide the compounds described herein or used to synthesize fragments which are subsequently joined by the methods described herein and/or documented elsewhere.

Formation of Covalent Linkages by Reaction of an Electrophile with a Nucleophile The compounds described herein can be modified using various electrophiles or nucleophiles to form new functional groups or substituents. Table 1 entitled "Examples of Covalent Linkages and Precursors Thereof" lists selected examples of covalent linkages and precursor functional groups which yield and can be used as guidance toward the variety of electrophiles and nucleophiles combinations available. Precursor functional groups are shown as electrophilic groups and nucleophilic groups.

TABLE 1

Examples of Covalent Linkages and Precursors Thereof

| Covalent Linkage Product | Electrophile | Nucleophile |
| --- | --- | --- |
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | carbodiimides | carboxylic acids |
| Esters | diazoalkanes | carboxylic acids |
| Thioethers | Epoxides | Thiols |
| Thioethers | haloacetamides | Thiols |
| Ammotriazines | halotriazines | amines/anilines |
| Triazinyl ethers | halotriazines | alcohols/phenols |
| Amidines | imido esters | amines/anilines |
| Ureas | Isocyanates | amines/anilines |
| Urethanes | Isocyanates | alcohols/phenols |
| Thioureas | isothiocyanates | amines/anilines |
| Thioethers | Maleimides | Thiols |
| Phosphite esters | phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |
| Alkyl thiol | α,β-unsaturated ester | thiols |
| Alkyl ethers | α,β-unsaturated ester | alcohols |
| Alkyl amines | α,β-unsaturated ester | amines |
| Alkyl thiol | Vinyl sulfone | thiols |
| Alkyl ethers | Vinyl sulfone | alcohols |
| Alkyl amines | Vinyl sulfone | amines |
| Vinyl sulfide | Propargyl amide | thiol |

Use of Protecting Groups

In the reactions described, it may be necessary to protect reactive functional groups, for example hydroxy, amino, imino, thio or carboxy groups, where these are desired in the final product, to avoid their unwanted participation in the reactions. Protecting groups are used to block some or all reactive moieties and prevent such groups from participating in chemical reactions until the protective group is removed. In one embodiment, each protective group be removable by a different means. Protective groups that are cleaved under totally disparate reaction conditions fulfill the requirement of differential removal. Protective groups can be removed by acid, base, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, but not limited to, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester compounds as exemplified herein, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts.

For example, an allyl-blocked carboxylic acid can be deprotected with a Pd⁰-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

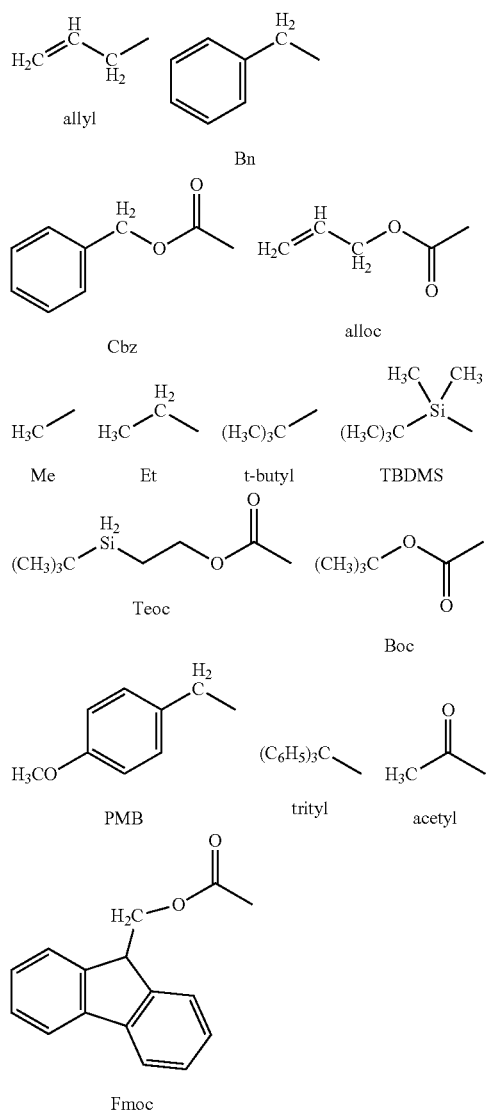

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Synthesis of Compounds

In certain embodiments, provided herein are methods of making and methods of using tyrosine kinase inhibitor compounds described herein. In certain embodiments, compounds described herein can be synthesized using the following synthetic schemes. Compounds may be synthesized using methodologies analogous to those described below by the use of appropriate alternative starting materials.

Described herein are compounds that inhibit the activity of tyrosine kinase(s), such as Btk, and processes for their preparation. Also described herein are pharmaceutically acceptable salts, pharmaceutically acceptable solvates, pharmaceutically active metabolites and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided.

The starting material used for the synthesis of the compounds described herein is either synthesized or obtained from commercial sources, such as, but not limited to, Aldrich Chemical Co. (Milwaukee, Wis.), Bachem (Torrance, Calif.), or Sigma Chemical Co. (St. Louis, Mo.). The compounds described herein, and other related compounds having different substituents are optionally synthesized using techniques and materials, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). Other methods for the synthesis of compounds described herein may be found in International Patent Publication No. WO 01/01982901, Arnold et al. *Bioorganic & Medicinal Chemistry Letters* 10 (2000) 2167-2170; Burchat et al. *Bioorganic & Medicinal Chemistry Letters* 12 (2002) 1687-1690. As a guide the following synthetic methods may be utilized.

The products of the reactions are optionally isolated and purified, if desired, using conventional techniques, including, but not limited to, filtration, distillation, crystallization, chromatography and the like. Such materials are optionally characterized using conventional means, including physical constants and spectral data.

Compounds described herein are optionally prepared using the synthetic methods described herein as a single isomer or a mixture of isomers.

A non-limiting example of a synthetic approach towards the preparation of compounds of any of Formula (I), (IA), (II), (IIIA), (IIIB), (IIIC), (IIID), or (IV) or other pyrazolopyrimidine compounds described herein is shown in Scheme I.

Scheme I.

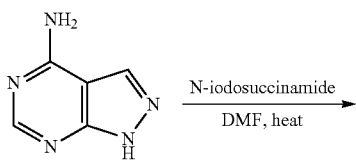

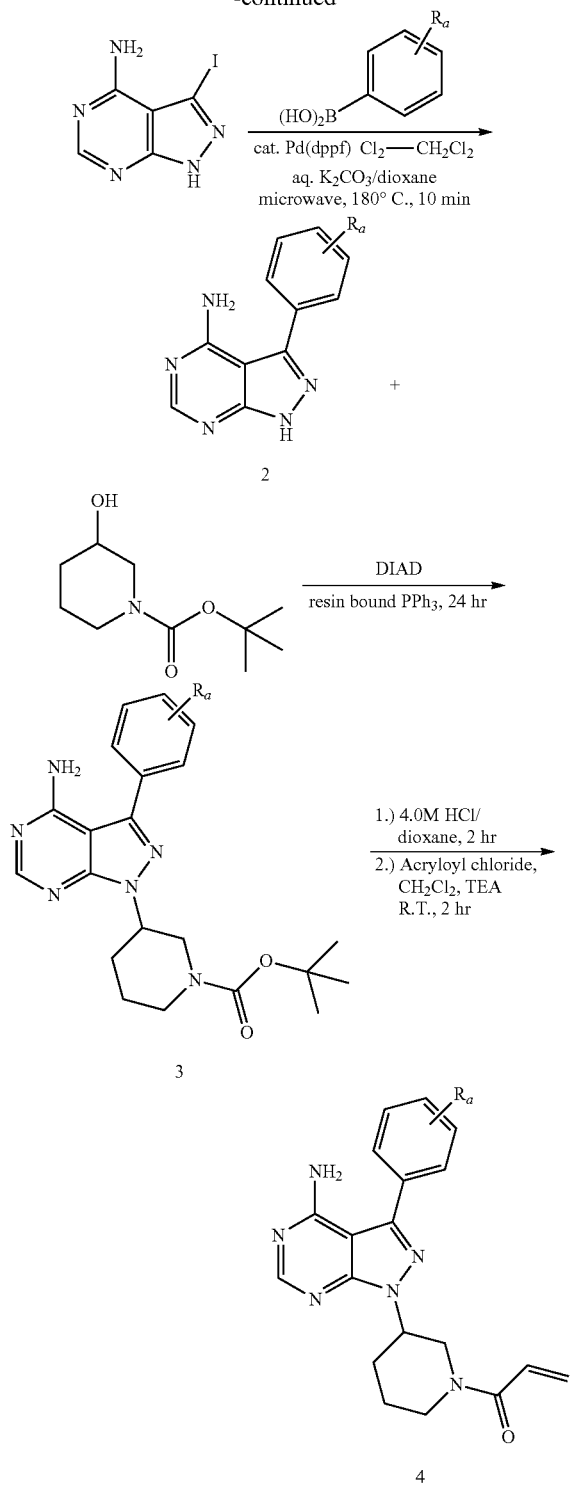

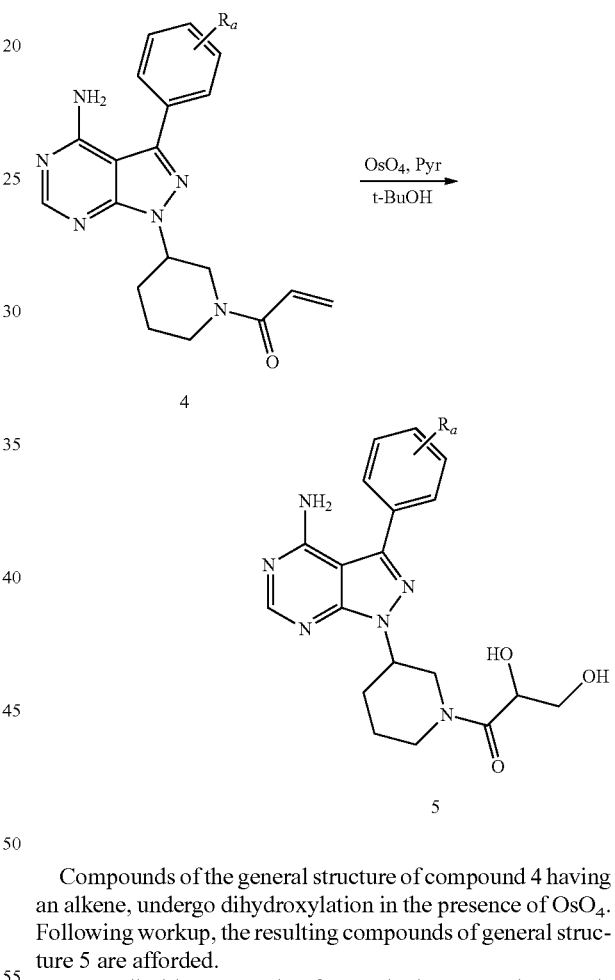

palladium mediated cross-coupling of a suitably substituted phenyl boronic acid under basic conditions constructs intermediate 2. Intermediate 2 is coupled with N-Boc-3-hydroxypiperidine (as non-limiting example) via Mitsunobu reaction to give the Boc (tert-butyloxycarbonyl) protected intermediate 3. After deprotection with acid, coupling with, but not limited to, an acid chloride, such as, but not limited to, acryloyl chloride, completes the synthesis to give compound 4.

A non-limiting example of a synthetic approach towards the preparation of compounds of Formula (II) is shown in Scheme II.

Scheme II.
Synthesis of 3-(4-amino-3-(4-phenoxyphenyl)-1H-pyrazolo[3,4-d]pyrimidin-1-yl)piperidin-1-yl)-2,3-dihydroxypropan-1-one Compounds of the general structure of compound 4 having an alkene, undergo dihydroxylation in the presence of OsO$_4$. Following workup, the resulting compounds of general structure 5 are afforded.

A non-limiting example of a synthetic approach towards the preparation of compounds of Formula (II) is shown in Scheme III.

Halogenation of commercially avalaible 1H-pyrazolo[3,4-d]pyrimidin-4-amine provides an entry into the synthesis of compounds of Formula (I), (IA), (II), (IIIA), (IIIB), (IIIC), (IIID), or (IV) or other pyrazolopyrimidine compounds described herein. In one embodiment, 1H-pyrazolo[3,4-d]pyrimidin-4-amine is treated with N-iodosuccinamide to give 3-iodo-1H-pyrazolo[3,4-d]pyrimidin-4-amine Metal catalyzed cross coupling reactions are then carried out on 3-iodo-1H-pyrazolo[3,4-d]pyrimidin-4-amine. In one embodiment, Scheme III.

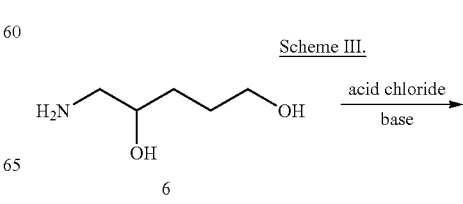

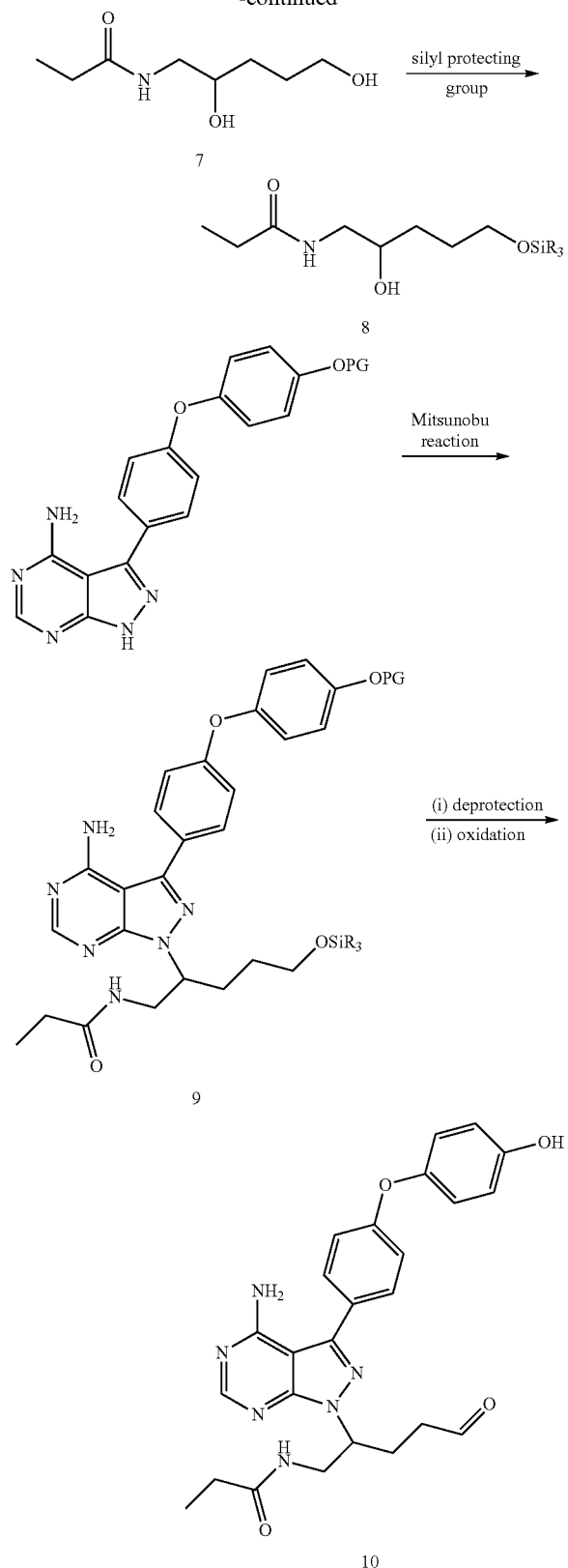

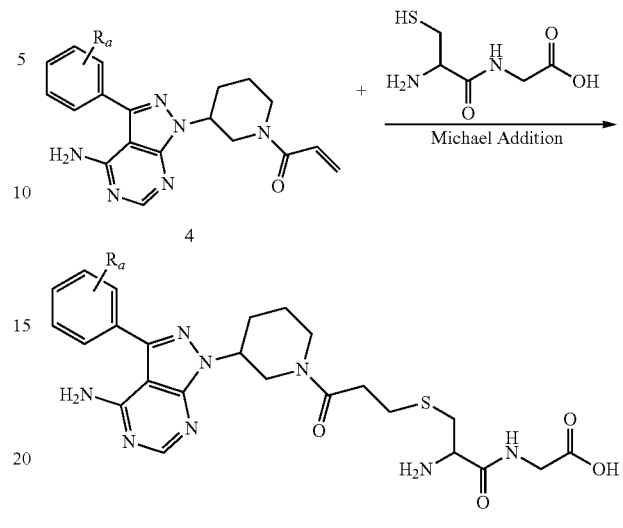

Scheme IV.

The compounds prepared by the methods disclosed herein are purified by conventional means, such as, for example, filtration, recrystallization, chromatography, distillation, and combinations thereof.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Further Forms of Compounds

Compounds disclosed herein have a structure of Formula (I), (IA), (II), (IIIA), (IIIB), (IIIC), (IIID), or (IV) or other pyrazolopyrimidine compounds described herein. It is understood that when reference is made to compounds described herein, it is meant to include compounds of any of Formula (I), (IA), (II), (IIIA), (IIIB), (IIIC), (IIID), or (IV) or other pyrazolopyrimidine compounds described herein, as well as to all of the specific compounds that fall within the scope of these generic formulae, unless otherwise indicated.

The compounds described herein may possess one or more stereocenters and each center may exist in the R or S configuration. The compounds presented herein include all diastereomeric, enantiomeric, and epimeric forms as well as the appropriate mixtures thereof. Stereoisomers may be obtained, if desired, by methods such as, for example, the separation of stereoisomers by chiral chromatographic columns.

Diasteromeric mixtures can be separated into their individual diastereomers on the basis of their physical chemical differences by methods known, for example, by chromatography and/or fractional crystallization. In one embodiment, enantiomers can be separated by chiral chromatographic columns. In other embodiments, enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

A non-limiting example of a synthetic approach towards the preparation of compounds of Formula (II) is shown in Scheme IV.

The methods and formulations described herein include the use of N-oxides, crystalline forms (also known as polymorphs), or pharmaceutically acceptable salts of compounds described herein, as well as active metabolites of these compounds having the same type of activity. In some situations, compounds exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

Compounds of any of Formula (I), (IA), (II), (IIIA), (IIIB), (IIIC), (IIID), or (IV) or other pyrazolopyrimidine compounds described herein in unoxidized form can be prepared from N-oxides of compounds of any of Formula (I), (IA), (II), (IIIA), (IIIB), (IIIC), (IIID), or (IV) or other pyrazolopyrimidine compounds described herein by treating with a reducing agent, such as, but not limited to, sulfur, sulfur dioxide, triphenyl phosphine, lithium borohydride, sodium borohydride, phosphorus trichloride, tribromide, or the like in a suitable inert organic solvent, such as, but not limited to, acetonitrile, ethanol, aqueous dioxane, or the like at 0 to 80° C.

Compounds described herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^{2}H$, $^{3}H$, $^{13}C$, $^{14}C$, $^{15}N$, $^{18}O$, $^{17}O$, $^{35}S$, $^{18}F$, $^{36}Cl$, respectively. Certain isotopically-labeled compounds described herein, for example those into which radioactive isotopes such as $^{3}H$ and $^{14}C$ are incorporated, are useful in drug and/or substrate tissue distribution assays. Further, substitution with isotopes such as deuterium, i.e., $^{2}H$, can afford certain therapeutic advantages resulting from greater metabolic stability, for example increased in vivo half-life or reduced dosage requirements.

Compounds described herein (for example, compounds of Formula (I), (IA), (II), (IIIA), (IIIB), (IIIC), (IIID), or (IV) or other pyrazolopyrimidine compounds described herein) are optionally in the form of, and/or used as, pharmaceutically acceptable salts. The type of pharmaceutical acceptable salts, include, but are not limited to: (1) acid addition salts, formed) by reacting the free base form of the compound with a pharmaceutically acceptable: inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts are optionally analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or, in the case of aqueous solutions, lyophilization.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are optionally formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds described herein are optionally in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Therapeutic Uses of Inhibitor Compounds

Described herein are methods, compositions, uses and medicaments for the treatment of disorders comprising administering to a patient in need an inhibitor of an ACK. In some embodiments, the ACK is Btk or a Btk homolog. In further embodiments, the ACK is Blk or a Blk homolog. In yet further embodiments, the ACK is tyrosine kinases that share homology with Btk by having a cysteine residue (including a Cys 481 residue) that can form a covalent bond with the inhibitor.

The methods described herein (which includes uses of a pharmaceutical composition to treat a disease or disorder, or uses of a compound to form a medicament for treating a disease or disorder) include administering to a subject in need a composition containing a therapeutically effective amount of one or more Btk inhibitor compounds described herein. Without being bound by theory, the diverse roles played by Btk signaling in various hematopoietic cell functions, e.g., B-cell receptor activation, show that small molecule Btk inhibitors are useful for reducing the risk of or treating a variety of diseases affected by or affecting many cell types of the hematopoietic lineage including, e.g., autoimmune diseases, heteroimmune conditions or diseases, inflammatory diseases, cancer (e.g., B-cell proliferative disorders), and thromboembolic disorders.

In some embodiments, are methods for treating an autoimmune disease or condition comprising administering to a patient in need a pharmaceutical formulation of any inhibitor of Btk (or a Btk homolog) of Formula (I), (IA), (II), (IIIA), (IIIB), (IIIC), (IIID), or (IV) or other pyrazolopyrimidine compounds described herein. Such an autoimmune disease or condition includes, but is not limited to, rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease,. Sjogren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, and vulvodynia. In some embodiments, the autoimmune disease is selected from rheumatoid arthritis or lupus.

In some embodiments, are methods for treating a heteroimmune disease or condition comprising administering to a patient in need a pharmaceutical formulation of any inhibitor of Btk (or a Btk homolog) of Formula (I), (IA), (II), (IIIA), (IIIB), (IIIC), (IIID), or (IV) or other pyrazolopyrimidine compounds described herein. Such a heteroimmune condition or disease includes, but is not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

In some embodiments, are methods for treating a cancer comprising administering to a patient in need a pharmaceutical formulation of any inhibitor of Btk (or a Btk homolog) of Formula (I), (IA), (II), (IIIA), (IIIB), (IIIC), (IIID), or (IV) or other pyrazolopyrimidine compounds described herein. Such a cancer, e.g., B-cell proliferative disorders, includes but is not limited to diffuse large B cell lymphoma, follicular lymphoma, chronic lymphocytic lymphoma, chronic lymphocytic leukemia, B-cell prolymphocytic leukemia, lymphoplasmacytic lymphoma/Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

In some embodiments, are methods for treating mastocytosis comprising administering to a patient in need a pharmaceutical formulation of any inhibitor of Btk (or a Btk homolog) of Formula (I), (IA), (II), (IIIA), (IIIB), (IIIC), (IIID), or (IV) or other pyrazolopyrimidine compounds described herein. Mastocytosis includes but is not limited to diseases characterized by hyperactive mast cells.

In some embodiments, are methods for treating osteoporosis or bone resorption disorders comprising administering to a patient in need a pharmaceutical formulation of any inhibitor of Btk (or a Btk homolog) of Formula (I), (IA), (II), (IIIA), (IIIB), (IIIC), (IIID), or (IV) or other pyrazolopyrimidine compounds described herein. Bone resorption disorders include but are not limted to Paget's disease of bone, osteoporosis, and the bone changes secondary to cancer, such as occur in myeloma and metastases from breast cancer.

In some embodiments, are methods for treating inflammatory diseases comprising administering to a patient in need a pharmaceutical formulation of any inhibitor of Btk (or a Btk homolog) of Formula (I), (IA), (II), (IIIA), (IIIB), (IIIC), (IIID), or (IV) or other pyrazolopyrimidine compounds described herein. Inflammatory diseases include but are not limited to asthma, inflammatory bowel disease, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

Further, the Btk inhibitor compounds described herein can be used to inhibit a small subset of other tyrosine kinases that share homology with Btk by having a cysteine residue (including a Cys 481 residue) that can form a covalent bond with the inhibitor. Thus, a subset of tyrosine kinases other than Btk are also expected to be useful as therapeutic targets in a number of health conditions, including:

autoimmune diseases, which include, but are not limited to, rheumatoid arthritis, psoriatic arthritis, osteoarthritis, Still's disease, juvenile arthritis, lupus, diabetes, myasthenia gravis, Hashimoto's thyroiditis, Ord's thyroiditis, Graves' disease, Sjögren's syndrome, multiple sclerosis, Guillain-Barré syndrome, acute disseminated encephalomyelitis, Addison's disease, opsoclonus-myoclonus syndrome, ankylosing spondylitisis, antiphospholipid antibody syndrome, aplastic anemia, autoimmune hepatitis, coeliac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, scleroderma, and vulvodynia.

heteroimmune conditions or diseases, which include, but are not limited to graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

inflammatory diseases, which include, but are not limited to asthma, inflammatory bowel disease, appendicitis, blepharitis, bronchiolitis, bronchitis, bursitis, cervicitis, cholangitis, cholecystitis, colitis, conjunctivitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

a cancer, e.g., B-cell proliferative disorders, which include, but are not limited to diffuse large B cell lymphoma, follicular lymphoma, chronic lymphocytic lymphoma, chronic lymphocytic leukemia, B-cell prolymphocytic leukemia, lymphoplasmacytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

thromboembolic disorders, which include, but are not limited to myocardial infarct, angina pectoris (including unstable angina), reocclusions or restenoses after angioplasty or aortocoronary bypass, stroke, transitory ischemia, peripheral arterial occlusive disorders, pulmonary embolisms, and deep venous thromboses.

Symptoms, diagnostic tests, and prognostic tests for each of the above-mentioned conditions includ, e.g., *Harrison's Principles of Internal Medicine©*," 16th ed., 2004, The McGraw-Hill Companies, Inc. Dey et al. (2006), Cytojournal 3(24), and the "Revised European American Lymphoma" (REAL) classification system (see, e.g., the website maintained by the National Cancer Institute).

A number of animal models are useful for establishing a range of therapeutically effective doses of inhibitors, including Btk inhibitor compounds for treating any of the foregoing diseases. Also, for example, dosing of inhibitor compounds for treating an autoimmune disease can be assessed in a mouse model of rheumatoid arthritis. In this model, arthritis is induced in Balb/c mice by administering anti-collagen antibodies and lipopolysaccharide. See Nandakumar et al. (2003), *Am. J. Pathol* 163:1827-1837. In another example, dosing of inhibitors for the treatment of B-cell proliferative disorders can be examined in, e.g., a human-to-mouse xenograft model in which human B-cell lymphoma cells (e.g. Ramos cells) are implanted into immunodefficient mice (e.g., "nude" mice) as described in, e.g., Pagel et al. (2005), Clin Cancer Res 11(13):4857-4866. Animal models for treatment of thromboembolic disorders are also known.

In one embodiment, the therapeutic efficacy of the compound for one of the foregoing diseases is optimized during a course of treatment. For example, a subject being treated optionally undergoes a diagnostic evaluation to correlate the relief of disease symptoms or pathologies to inhibition of in vivo Btk activity achieved by administering a given dose of an Btk inhibitor. Cellular assays are used to determine in vivo activity of Btk in the presence or absence of an Btk inhibitor. For example, since activated Btk is phosphorylated at tyrosine 223 (Y223) and tyrosine 551 (Y551), phospho-specific immunocytochemical staining of P-Y223 or P-Y551-positive cells are used to detect or quantify activation of Bkt in a population of cells (e.g., by FACS analysis of stained vs unstained cells). See, e.g., Nisitani et al. (1999), *Proc. Natl. Acad. Sci, USA* 96:2221-2226. Thus, the amount of the Btk inhibitor inhibitor compound that is administered to a subject is optionally increased or decreased as needed so as to maintain a level of Btk inhibition optimal for treating the subject's disease state.

Combination Treatments

The Btk inhibitor compositions described herein can also be used in combination with other well known therapeutic reagents that are selected for their therapeutic value for the condition to be treated. In general, the compositions described herein and, in embodiments where combinational therapy is employed, other agents do not have to be administered in the same pharmaceutical composition, and are optionally, because of different physical and chemical characteristics, have to be administered by different routes. The initial administration is made, for example, according to established protocols, and then, based upon the observed effects, the dosage, modes of administration and times of administration are modified.

In certain instances, it is appropriate to administer at least one Btk inhibitor compound described herein in combination with another therapeutic agent. By way of example only, if one of the side effects experienced by a patient upon receiving one of the Btk inhibitor compounds described herein is nausea, then it is appropriate to administer an anti-nausea agent in combination with the initial therapeutic agent. Or, by way of example only, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, by way of example only, the benefit experienced by a patient is increased by administering one of the compounds described herein with another therapeutic agent (which also includes a therapeutic regimen) that also has therapeutic benefit. In any case, regardless of the disease, disorder or condition being treated, the overall benefit experienced by the patient is in some embodiments simply additive of the two therapeutic agents or in other embodiments, the patient experiences a synergistic benefit.

The particular choice of compounds used will depend upon the diagnosis of the attending physicians and their judgment of the condition of the patient and the appropriate treatment protocol. The compounds are optionally administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is based on an evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound of Formula (I), (IA), (II), (IIIA), (IIIB), (IIIC), (IIID), or (IV) or other pyrazolopyrimidine compounds described herein described herein) are optionally administered in any order or even simultaneously. If simultaneously, the multiple therapeutic agents are optionally provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also are optionally used in combination with procedures that provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

In some embodiments, the compounds described herein and combination therapies are administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, within the first 6 hours of the onset of the symptoms, or within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound should be administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, between about 1 month to about 5 years, or from about 1 month to about 3 years.

Exemplary Therapeutic Agents for Use in Combination with an Inhibitor Compound

In some embodiments, where the subject is suffering from or at risk of suffering from an autoimmune disease, an inflammatory disease, or an allergy disease, a Btk inhibitor compound is used in with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, allergy vaccines, antihistamines, antileukotrienes, beta-agonists, theophylline, anticholinergics or other selective kinase inhibitors (e.g p38 inhibitors, Syk inhibitors, PKC inhibitors).

In yet other embodiments, where the subject is suffering from or at risk of suffering from a B-cell proliferative disorder (e.g., plasma cell myeloma), the subjected is treated with a Btk inhibitor compound in any combination with one or more other anti-cancer agents. In some embodiments, one or more of the anti-cancer agents are proapoptotic agents. Examples of anti-cancer agents include, but are not limited to, any of the following: gossyphol, Genasense®, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, or PD184352, Taxol®, also referred to as "paclitaxel", which is a well-known anti-cancer drug which acts by enhancing and stabilizing microtubule formation, and analogs of Taxol®, such as Taxotere®. Compounds that have the basic taxane skeleton as a common structure feature, have also been shown to have the ability to arrest cells in the G2-M phases due to stabilized microtubules and may be useful for treating cancer in combination with the compounds described herein.

Further examples of anti-cancer agents for use in combination with an Btk inhibitor compound include inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., Rituxan®).

In further embodiments, other anti-cancer agents are employed in combination with an Btk inhibitor compound include Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

In yet other embodiments, other anti-cancer agents are employed in combination with an Btk inhibitor compound include: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Yet other anticancer agents that can be employed in combination with a Btk inhibitor compound include alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, ete.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

Examples of natural products useful in combination with a Btk inhibitor compound include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents that are employed in combination a Btk inhibitor compound in some embodiments, include, but are not limited to, nitrogen mustards (e.g., mechloroethamine, cyclophosphamide, chlorambucil, meiphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, ete.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

Examples of hormones and antagonists useful in combination with a Btk inhibitor compound include, but are not limited to, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and compositions described herein for the treatment or prevention of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

Examples of anti-cancer agents which act by arresting cells in the G2-M phases due to stabilized microtubules and which are used in some embodiments, in combination with a Btk inhibitor compound include without limitation marketed drugs and drugs in development.

Where the subject is suffering from or at risk of suffering from a thromboembolic disorder (e.g., stroke), the subject, in some embodiments is treated with a Btk inhibitor compound in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), factor VIIa inhibitors, ticlopidine, clopidogrel, CS-747 (prasugrel, LY640315), ximelagatran, or BIBR 1048.

Pharmaceutical Composition/Formulation

Pharmaceutical compositions are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery* Systems, Seventh Ed. (Lippincott Williams & Wilkins 1999).

A pharmaceutical composition, as used herein, refers to a mixture of a compound described herein, such as, for example, compounds of any of Formula (I), (IA), (II), (IIIA), (IIIB), (IIIC), (IIID), or (IV) or other pyrazolopyrimidine compounds described herein, with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. Preferably, the mammal is a human. The compounds, in some embodiments, are used singly or in combination with one or more therapeutic agents as components of mixtures.

The pharmaceutical formulations described herein in some embodiments, is administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein are optionally manufactured in a conventional manner, such as, by way of example only, by means of conventional mixing, dissolving, granulating, dragee-making, levigating, emulsifying, encapsulating, entrapping or compression processes.

The pharmaceutical compositions in further embodiments, include at least one compound described herein, such as, for example, a compound of Formula (I), (IA), (II), (IIIA), (IIIB), (IIIC), (IIID), or (IV) or other pyrazolopyrimidine compounds described herein, as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds exist as tautomers. All tautomers are included within the scope of the compounds presented herein. By way of example only, in one embodiment, the tautomeric form of the compound of Formula (I) has the structure of Formula (IA):

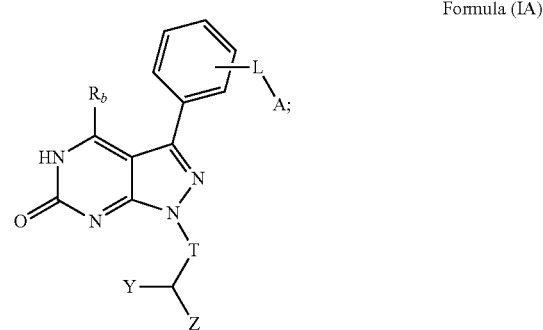

Formula (IA)

wherein:
L is a bond, $CH_2$, O, $NR_2$, S, CO, C=$NR_2$, or C=N—$OR_2$;
T is a bond, $C_1$-$C_6$alkylene, or $C_3$-$C_6$cycloalkylene;
A is aryl or heteroaryl wherein aryl or heteroaryl is optionally substituted with at least one $R_1$;
Y and Z are each independently selected from H, $C_1$-$C_6$alkyl, $C_2$-$C_6$alkenyl, $C_3$-$C_{10}$cycloalkyl, $C_1$-$C_6$heteroalkyl, $C_2$-$C_6$heteroalkenyl, $C_4$-$C_{10}$heterocycloalkenyl and $C_2$-$C_{10}$heterocycloalkyl, wherein $C_1$-$C_6$alkyl, $C_2$-$C_6$alkenyl, $C_3$-$C_{10}$cycloalkyl, $C_1$-$C_6$heteroalkyl, $C_2$-$C_6$heteroalkenyl, $C_4$-$C_{10}$heterocycloalkenyl and $C_2$-$C_{10}$heterocycloalkyl are optionally substituted with at least one $R_1$; or
Y and Z together with the carbon atom to which they are attached form a $C_3$-$C_{10}$cycloalkyl, $C_2$-$C_{10}$heterocycloalkyl, $C_4$-$C_{10}$heterocycloalkenyl, aryl, or heteroaryl, wherein $C_3$-$C_{10}$cycloalkyl, $C_2$-$C_{10}$heterocycloalkyl, $C_4$-$C_{10}$heterocycloalkenyl, aryl, or heteroaryl, are optionally substituted with at least one X;
wherein when Y and Z together with the carbon atom to which they are attached form a nitrogen atom-containing $C_2$-$C_{10}$heterocycloalkyl or $C_4$-$C_{10}$heterocycloalkenyl, the nitrogen atom of the $C_2$-$C_{10}$heterocycloalkyl or $C_4$-$C_{10}$heterocycloalkenyl is optionally substituted with W and the carbon atoms of the $C_2$-$C_{10}$heterocycloalkyl or $C_4$-$C_{10}$heterocycloalkenyl are optionally substituted with at least one X;
W is selected from J, C(=O)-J, C(=O)O-J, C(=O)$NR_2$-J, C(=$NR_2$)-J, —C(=$NR_2$)$NR_2$-J, C(=N—$OR_3$)-J, C(=S)-J, S(=O)$_v$-J, S(=O)$_v$O-J;

X is F, Cl, Br, I, —CN, —NO$_2$, —OR$_3$, —N(R$_2$)$_2$, —SR$_2$, —C$_1$-C$_6$alkyl, —C(=O)R$_2$, —OC(=O)R$_2$, —NR$_2$C(=O)R$_2$, —NR$_2$C(=O)N(R$_2$)$_2$, —C(=O)N(R$_2$)$_2$, —C(=NR$_2$)N(R$_2$)$_2$, —C(=N—OR$_2$)N(R$_2$)$_2$), —C(=S)R$_2$, —S(=O)$_v$R$_2$, —OS(=O)$_v$R$_2$, —NR$_2$C(=O)OR$_2$, —NR$_2$S(=O)$_v$R$_2$;

J is —C$_1$-C$_6$alkyl, C$_3$-C$_6$cycloalkyl, -C$_2$-C$_6$alkene, C$_2$-C$_6$heterocycloalkyl, aryl, or heteroaryl optionally substituted with at least one R$_1$;

v is 1 or 2;

R$_b$ is NH$_2$, OH, OSO$_3$H or NHSO$_3$H;

R$_1$ is selected from F, Cl, Br, I, —CN, —NO$_2$, —SR$_2$, —OR$_3$, C$_1$-C$_6$alkyl, C$_1$-C$_6$haloalkyl, C$_1$-C$_6$hydroxyalkyl, —OC$_1$-C$_6$haloalkyl, C$_1$-C$_6$heteroalkyl, C$_3$-C$_6$cycloalkyl, C$_2$-C$_6$heterocycloalkyl, phenyl, —NR$_2$S(=O)$_2$R$_2$, —S(=O)$_2$N(R$_2$)$_2$, —C(=O)CF$_3$, —C(=O)NR$_2$S(=O)$_2$R$_2$, —S(=O)$_2$NR$_2$C(=O)R$_2$, —N(R$_2$)$_2$, wherein optionally the two R$_2$ groups of N(R$_2$)$_2$ and the nitrogen atom to which they are attached form a C$_2$-C$_6$ heterocycloalkyl ring, —NR$_2$C(=O)R$_2$, —NR$_2$C(=O)N(R$_2$)$_2$, —CO$_2$R$_2$, —C(=O)R$_2$, —OC(=O)R$_2$, —C(=O)N(R$_2$)$_2$, —S(=O)R$_2$, —S(=O)$_2$R$_2$, —SO$_3$H, and at least one amino acid fragment;

R$_2$ is H, C$_1$-C$_6$alkyl, C$_1$-C$_6$haloalkyl, C$_1$-C$_6$hydroxyalkyl, or C$_3$-C$_6$cycloalkyl;

R$_3$ is H, methyl, ethyl, n-propyl, iso-propyl, n-butyl, iso-butyl, tert-butyl, or SO$_3$H; or a pharmaceutically acceptable salt, solvate, or tautomeric form thereof.

In one embodiment, is a compound of Formula (IA) wherein R$_b$ is NH$_2$. In another embodiment, is a compound of Formula (IA) wherein L is O and A is an aryl group. In a further embodiment, is a compound of Formula (IA) wherein T is a bond or CH$_2$. In another embodiment, Y and Z together with the carbon atom to which they are attached form a C$_3$-C$_{10}$cycloalkyl, C$_2$-C$_{10}$heterocycloalkyl, C$_4$-C$_{10}$heterocycloalkenyl, aryl, or heteroaryl, wherein C$_3$-C$_{10}$cycloalkyl, C$_2$-C$_{10}$heterocycloalkyl, C$_4$-C$_{10}$heterocycloalkenyl, aryl, or heteroaryl, are optionally substituted with at least one X.

Additionally, the compounds described herein can exist in unsolvated as well as solvated forms with pharmaceutically acceptable solvents such as water, ethanol, and the like. The solvated forms of the compounds presented herein are also considered to be disclosed herein.

A "carrier" or "carrier materials" includes excipients in pharmaceutics and is selected on the basis of compatibility with compounds disclosed herein, such as, compounds of Formula (I), (IA), (II), (IIIA), (IIIB), (IIIC), (IIID), or (IV) and the release profile properties of the desired dosage form. Exemplary carrier materials include, e.g., binders, suspending agents, disintegration agents, filling agents, surfactants, solubilizers, stabilizers, lubricants, wetting agents, diluents, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

A "measurable serum concentration" or "measurable plasma concentration" describes the blood serum or blood plasma concentration, typically measured in mg, μg, or ng of therapeutic agent per ml, dl, or l of blood serum, absorbed into the bloodstream after administration. As used herein, measurable plasma concentrations are typically measured in ng/ml or μg/ml.

"Pharmacodynamics" refers to the factors which determine the biologic response observed relative to the concentration of drug at a site of action. "Pharmacokinetics" refers to the factors which determine the attainment and maintenance of the appropriate concentration of drug at a site of action.

"Steady state," as used herein, is when the amount of drug administered is equal to the amount of drug eliminated within one dosing interval resulting in a plateau or constant plasma drug exposure.

Dosage Forms

Moreover, the pharmaceutical compositions described herein, which include a compound of Formula (I), (IA), (II), (IIIA), (IIIB), (IIIC), or (IIID) are, in some embodiments, formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the formulation of the compound of Formula (I), (IA), (II), (IIIA), (IIIB), (IIIC), or (IIID). In one embodiment, some or all of the particles of the compound of Formula (I), (IA), (II), (IIIA), (IIIB), (IIIC), (IIID), or (IV) are coated. In another embodiment, some or all of the particles of the compound of Formula (I), (IA), (II), (IIIA), (IIIB), (IIIC), (IIID), or (IV) are microencapsulated. In still another embodiment, the particles of the compound of Formula (I), (IA), (II), (IIIA), (IIIB), (IIIC), (IIID), or (IV) are not microencapsulated and are uncoated.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound of any of Formula (I), (IA), (II), (IIIA), (IIIB), (IIIC), (IIID), or (IV) with one or more pharmaceutical excipients to form a bulk blend composition. When referring to these bulk blend compositions as homogeneous, it is meant that the particles of the compound of any of Formula (I), (IA), (II), (IIIA), (IIIB), (IIIC), (IIID), or (IV) are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., The Theory and Practice of Industrial Pharmacy (1986). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the formulation of the compound of any of Formula (I), (IA), (II), (IIIA), (IIIB), (IIIC), or (IIID) In one embodiment, some or all of the particles of the compound of any of Formula (I), (IA), (II), (IIIA), (IIIB), (IIIC), (IIID), or (IV) are coated. In another embodiment, some or all of the particles of the compound of any of Formula (I), (IA), (II), (IIIA), (IIIB), (IIIC), (IIID), or (IV) are microencapsulated. In still another embodiment, the particles of the compound of any of Formula (I), (IA), (II), (IIIA), (IIIB), (IIIC), (IIID), or (IV) are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatmized starch, hydroxypropylmethylcellulose (HPMC), hydroxypropylmethylcellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of any of Formula (I), (IA), (II), (IIIA), (IIIB), (IIIC), (IIID), or (IV) from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crosspovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 g/cm.sup.3, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating can provide a delayed release of the compound of any of Formula (I), (IA), (II), (IIIA), (IIIB), (IIIC), (IIID), or (IV) from the formulation. In other embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the compound of any of Formula (I), (IA), (II), (IIIA), (IIIB), (IIIC), (IIID), or (IV) described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound of any of Formula (I), (IA), (II), (IIIA), (IIIB), (IIIC), (IIID), or (IV) and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds of any of Formula (I), (IA), (II), (IIIA), (IIIB), (IIIC), (IIID), or (IV) which sufficiently isolate the compound of any of Formula (I), (IA), (II), (IIIA), (IIIB), (IIIC), (IIID), or (IV) from other non-compatible excipients. Materials compatible with compounds of any of Formula (I), (IA), (II), (IIIA), (IIIB), (IIIC), (IIID), or (IV) are those that delay the release of the compounds of any of Formula (I), (IA), (II), (IIIA), (IIIB), (IIIC), (IIID), or (IV) in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, OpadryYS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IRO, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel.

Microencapsulated compounds of any of Formula (I), (IA), (II), (IIIA), (IIIB), (IIIC), (IIID), or (IV) may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In one embodiment, the particles of compounds of any of Formula (I), (IA), (II), (IIIA), (IIIB), (IIIC), (IIID), or (IV) are microencapsulated prior to being formulated into one of the above forms. In still another embodiment, some or most of the particles are coated prior to being further formulated by using standard coating procedures, such as those described in Remington's Pharmaceutical Sciences, 20th Edition (2000).

In other embodiments, the solid dosage formulations of the compounds of any of Formula (I), (IA), (II), (IIIA), (IIIB), (IIIC), (IIID), or (IV) are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In other embodiments, a powder including the formulations with a compound of any of Formula (I), (IA), (II), (IIIA), (IIIB), (IIIC), (IIID), or (IV) described herein, may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In other embodiments, the formulations described herein, which include a compound of Formula (A), are solid dispersions. Methods of producing such solid dispersions are known in the art and include, but are not limited to, for example, U.S. Pat. Nos. 4,343,789, 5,340,591, 5,456,923, 5,700,485, 5,723,269, and U.S. Pub. Appl 2004/0013734, each of which is specifically incorporated by reference. In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions are known in the art and include, but are not limited to, for example, U.S. Pat. Nos. 4,151,273, 5,281,420, and 6,083,518, each of which is specifically incorporated by reference.

The pharmaceutical solid oral dosage forms including formulations described herein, which include a compound of any of Formula (I), (IA), (II), (IIIA), (IIIB), (IIIC), (IIID), or (IV) can be further formulated to provide a controlled release of the compound of Formula (A). Controlled release refers to the release of the compound of any of Formula (I), (IA), (II), (IIIA), (IIIB), (IIIC), (IIID), or (IV) from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In other embodiments, the polymers and compatible mixtures thereof, and some of their properties, include, but are not limited to:

Shellac, also called purified lac, a refined product obtained from the resinous secretion of an insect. This coating dissolves in media of pH>7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine;

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH >6. Aquateric (FMC) is an aqueous based system and is a spray dried CAP psuedolatex with particles <1 Mm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions;

Poly Vinyl Acetate Phthalate (PVAP). PVAP dissolves in pH >5, and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnuba wax or PEG) may be added to the coatings besides plasticizers to solubilize or disperse the coating material, and to improve coating performance and the coated product.

In other embodiments, the formulations described herein, which include a compound of Formula (A), are delivered using a pulsatile dosage form. A pulsatile dosage form is capable of providing one or more immediate release pulses at predetermined time points after a controlled lag time or at specific sites. Pulsatile dosage forms including the formulations described herein, which include a compound of any of Formula (I), (IA), (II), (IIIA), (IIIB), (IIIC), (IIID), or (IV) may be administered using a variety of pulsatile formulations known in the art. For example, such formulations include, but are not limited to, those described in U.S. Pat. Nos. 5,011,692, 5,017,381, 5,229,135, and 5,840,329, each of which is specifically incorporated by reference. Other pulsatile release dosage forms suitable for use with the present formulations include, but are not limited to, for example, U.S. Pat. Nos. 4,871,549, 5,260,068, 5,260,069, 5,508,040, 5,567,441 and 5,837,284, all of which are specifically incorporated by reference. In one embodiment, the controlled release dosage form is pulsatile release solid oral dosage form including at least two groups of particles, (i.e. multiparticulate) each containing the formulation described herein. The first group of particles provides a substantially immediate dose of the compound of any of Formula (I), (IA), (II), (IIIA), (IIIB), (IIIC), (IIID), or (IV) upon ingestion by a mammal. The first group of particles can be either uncoated or include a coating and/or sealant. The second group of particles includes coated particles, which includes from about 2% to about 75%, from about 2.5% to about 70%, or from about 40% to about 70%, by weight of the total dose of the compound of any of Formula (I), (IA), (II), (IIIA), (IIIB), (IIIC), (IIID), or (IV) in said formulation, in admixture with one or more binders. The coating includes a pharmaceutically acceptable ingredient in an amount sufficient to provide a delay of from about 2 hours to about 7 hours following ingestion before release of the second dose. Suitable coatings include one or more differentially degradable coatings such as, by way of example only, pH sensitive coatings (enteric coatings) such as acrylic resins (e.g., Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® 512.5, and Eudragit® NE30D, Eudragit® NE 40D®) either alone or blended with cellulose derivatives, e.g., ethylcellulose, or non-enteric coatings having variable thickness to provide differential release of the formulation that includes a compound of any of Formula (I), (IA), (II), (IIIA), (IIIB), (IIIC), or (IIID).

Many other types of controlled release systems known to those of ordinary skill in the art and are suitable for use with the formulations described herein. Examples of such delivery systems include, e.g., polymer-based systems, such as polylactic and polyglycolic acid, polyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., Pharmaceutical Dosage Forms, 2 Ed., Vol. 1, pp. 209-214 (1990); Singh et al., Encyclopedia of Pharmaceutical Technology, 2.sup.nd Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983, each of which is specifically incorporated by reference.

In some embodiments, pharmaceutical formulations are provided that include particles of the compounds of any of Formula (I), (IA), (II), (IIIA), (IIIB), (IIIC), (IIID), or (IV) described herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2.sup.nd Ed., pp. 754-757 (2002). In addition to the particles of compound of Formula (A), the liquid dosage forms may include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®. Avicel® PH 101, Avicel® PH102, Avicel® PH1105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crosspovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein are known in the art and include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In one embodiment, the aqueous liquid dispersion can comprise a sweetening agent or flavoring agent in a concentration ranging from about 0.001% to about 1.0% the volume of the aqueous dispersion. In another embodiment, the aqueous liquid dispersion can comprise a sweetening agent or flavoring agent in a concentration ranging from about 0.005% to about 0.5% the volume of the aqueous dispersion. In yet another embodiment, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,858,401, 6,667,048, and 6,960,563, each of which is specifically incorporated by reference.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Intranasal Formulations

Intranasal formulations are known in the art and are described in, for example, U.S. Pat. Nos. 4,476,116, 5,116,817 and 6,391,452, each of which is specifically incorporated by reference. Formulations that include a compound of any of Formula (I), (IA), (II), (IIIA), (IIIB), (IIIC), (IIID), or (IV) which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. The nasal dosage form should be isotonic with nasal secretions.

For administration by inhalation, the compounds of any of Formula (I), (IA), (II), (IIIA), (IIIB), (IIIC), (IIID), or (IV) described herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal Formulations

Buccal formulations that include compounds of any of Formula (I), (IA), (II), (IIIA), (IIIB), (IIIC), (IIID), or (IV) may be administered using a variety of formulations known in the art. For example, such formulations include, but are not limited to, U.S. Pat. Nos. 4,229,447, 4,596,795, 4,755,386, and 5,739,136, each of which is specifically incorporated by reference. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the compound of any of Formula (I), (IA), (II), (IIIA), (IIIB), (IIIC), (IIID), or (IV) is provided essentially throughout. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with the compound of any of Formula (I), (IA), (II), (IIIA), (IIIB), (IIIC), (IIID), or (IV) and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal Formulations

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144, each of which is specifically incorporated by reference in its entirety.

The transdermal dosage forms described herein may incorporate certain pharmaceutically acceptable excipients which are conventional in the art. In one embodiments, the transdermal formulations described herein include at least three components: (1) a formulation of a compound of any of Formula (I), (IA), (II), (IIIA), (IIIB), (IIIC), or (IIID); (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds of any of Formula (I), (IA), (II), (IIIA), (IIIB), (IIIC), or (IIID) The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Injectable Formulations

Formulations that include a compound of any of Formula (I), (IA), (II), (IIIA), (IIIB), (IIIC), (IIID), or (IV) suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethyleneglycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

Other Formulations

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly (methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Examples of Methods of Dosing and Treatment Regimens

The compounds described herein, in some embodiments, is used in the preparation of medicaments for the inhibition of Btk or a homolog thereof, or for the treatment of diseases or conditions that benefit, at least in part, from inhibition of Btk or a homolog thereof. In addition, a method for treating any of the diseases or conditions described herein in a subject in need of such treatment, involves administration of pharmaceutical compositions containing at least one compound of any of Formula (I), (IA), (II), (IIIA), (IIIB), (IIIC), (IIID), or (IV) described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

The compositions containing the compound(s) described herein, in other embodiments, are administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In some embodiments, the kinase inhibitor is administered to the patient on a regular basis, e.g., three times a day, two times a day, once a day, every other day or every 3 days. In other embodiments, the kinase inhibitor is administered to the patient on an intermittent basis, e.g., twice a day followed by once a day followed by three times a day; or the first two days of every week; or the first, second and third day of a week. In some embodiments, intermittent dosing is as effective as regular dosing. In further or alternative embodiments, the kinase inhibitor is administered only when the patient exhibits a particular symptom, e.g., the onset of pain, or the onset of a fever, or the onset of an inflammation, or the onset of a skin disorder.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from about 10%-about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, and is determined according to the particular circumstances surrounding the case, including, e.g., the specific agent being administered, the route of administration, the condition being treated, and the subject or host being treated. In general, however, doses employed for adult human treatment will typically be in the range of about 0.02-about 5000 mg per day, or from about 1-about 1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multidose containers, with an added preservative.

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Dosing Strategies to Increase Selectivity

Described herein are kinase inhibitors that are selective for one or more ACKs, including a Btk, a Btk homolog, and a Btk kinase cysteine homolog. In some embodiments, the inhibitors described herein also bind reversibly to other kinases (some of which, in some embodiments, are also ACKs). As a means of enhancing the selectivity profile, such inhibitors are formulated (formulation includes chemical modifications of the inhibitor, use of excipients in a pharmaceutical composition, and combinations thereof) such that the pharmacokinetic profile favors enhanced selectivity of the inhibitors for an ACK over a non-ACK. By way of example only, an ACK is formulated to have a short plasma half-life. In other embodiments, an ACK is formulated to have an extended plasma half-life.

In one embodiment are kinase inhibitors that selectively and irreversibly binds to a protein tyrosine kinase selected from Btk, a Btk homolog, and a Btk kinase cysteine homolog, in which the kinase inhibitor reversibly and non-selectively binds to a multiplicity of protein tyrosine kinases, and further in which the plasma half life of the kinase inhibitor is less than about 4 hours. In such an embodiment, the kinase inhibitor selectively and irreversibly binds to at least one of Btk, Jak3, Blk, Bmx, Tec, and Itk. In a further embodiment, the kinase inhibitor selectively and irreversibly binds to Btk. In a further embodiment, the kinase inhibitor selectively and irreversibly binds to Jak3. In a further embodiment, the kinase inhibitor selectively and irreversibly binds to Tec. In a further embodiment, the kinase inhibitor selectively and irreversibly binds to Btk and Tec. In a further embodiment, the kinase inhibitor selectively and irreversibly binds to Blk. In a further embodiment, the kinase inhibitor reversibly and non-selectively binds to a multiplicity of src-family protein kinase inhibitors. In a further embodiment, the plasma half life of the kinase inhibitor is less than about 3 hours. In a further embodiment, the plasma half life of the kinase inhibitor is less than about 2 hours.

In one embodiment are kinase inhibitors that selectively and irreversibly binds to a protein tyrosine kinase selected from Btk, a Btk homolog, and a Btk kinase cysteine homolog, in which the kinase inhibitor reversibly and non-selectively binds to a multiplicity of protein tyrosine kinases, and further in which the plasma half life of the kinase inhibitor is greater than about 12 hours. In such an embodiment, the kinase inhibitor selectively and irreversibly binds to at least one of Btk, Jak3, Blk, Bmx, Tec, and Itk. In a further embodiment, the kinase inhibitor selectively and irreversibly binds to Btk. In a further embodiment, the kinase inhibitor selectively and irreversibly binds to Jak3. In a further embodiment, the kinase inhibitor selectively and irreversibly binds to Tec. In a further embodiment, the kinase inhibitor selectively and irreversibly binds to Btk and Tec. In a further embodiment, the kinase inhibitor selectively and irreversibly binds to Blk. In a further embodiment, the kinase inhibitor reversibly and non-selectively binds to a multiplicity of src-family protein kinase inhibitors In a further embodiment, the kinase inhibitor the plasma half life of the kinase inhibitor is greater than about 16 hours.

In another aspect of such dosing methods are pharmaceutical formulations comprising any of the aforementioned ACK inhibitors and a pharmaceutically acceptable excipient. In some embodiments, such pharmaceutical formulations are formulated for a route of administration selected from oral administration, parenteral administration, buccal administration, nasal administration, topical administration, or rectal administration. In certain embodiments, the pharmaceutical formulations are formulated for oral administration.

In another aspect of such dosing methods are methods for treating rheumatoid arthritis comprising administering to a subject any of the aforementioned ACK inhibitors that selectively and irreversibly binds to Btk and Tec.

In a further aspect of such dosing strategies are methods for treating a B-cell proliferative disorder or a mast cell proliferative disorder comprising administering to a patient in need a pharmaceutical composition of any of the aforementioned ACK inhibitors.

In a further aspect of such dosing strategies are methods for treating a rheumatoid arthritis or condition comprising administering to a patient in need a pharmaceutical composition of any of the aforementioned ACK inhibitors. In a further aspect of such dosing strategies are methods for treating a disease characterized by hyperactive B cells comprising administering to a patient in need a pharmaceutical composition of any of the aforementioned ACK inhibitors. In a further aspect of such dosing strategies are methods for treating a disease characterized by hyperactive mast cells comprising administering to a patient in need a pharmaceutical composition of any of the aforementioned ACK inhibitors. In a further aspect of such dosing strategies are methods for treating a disease characterized by both hyperactive B cells and hyperactive mast cells comprising administering to a patient in need a pharmaceutical composition of any of the aforementioned ACK inhibitors. In any of the aforementioned treatment methods using such dosing strategies, the pharmaceutical composition is administered once a day or less frequently than once a day.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products include, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that benefit by inhibition of Btk, or in which Btk is a mediator or contributor to the symptoms or cause.

For example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

The following specific and non-limiting examples are to be construed as merely illustrative, and do not limit the present disclosure in any way whatsoever.

Synthesis of Compounds

Example 1

Preparation of 4-Amino-3-(4-phenoxyphenyl)-1H-pyrazolo[3,4-d]pyrimidine (2a)

4-Amino-3-(4-phenoxyphenyl)-1H-pyrazolo[3,4-d]pyrimidine (Intermediate 2) is prepared as disclosed in International Patent Publication No. WO 01/019829. Briefly, 4-phenoxybenzoic acid (48 g) is added to thionyl chloride (100 mL) and heated under gentle reflux for 1 hour. Thionyl chloride is removed by distillation, the residual oil dissolved in toluene and volatile material removed at 80° C./20 mbar. The resulting acid chloride is dissolved in toluene (200 mL) and tetrahydrofuran (35 mL). Malononitrile (14.8 g) is added and the solution and stirred at −10° C. while adding diisopropylethylethylamine (57.9 g) in toluene (150 mL), while maintaining the temperature below 0° C. After 1 hour at 0° C., the mixture is stirred at 20° C. overnight. Amine hydrochloride is removed by filtration and the filtrate evaporated in vacuo. The residue is taken up in ethyl acetate and washed with 1.25 M sulphuric acid, then with brine and dried over sodium sulfate. Evaporation of the solvents gives a semisolid residue which is treated with a little ethyl acetate to give 4.1 g of 1,1-dicyano-2-hydroxy-2-(4-phenoxyphenyl)ethene as a white solid (m.p. 160-162° C.). The filtrate on evaporation gives 56.58 (96%) of 1,1-dicyano-2-hydroxy-2-(4-phenoxyphenyl)ethene as a grey-brown solid, which is sufficiently pure for further use.

1,1-Dicyano-2-hydroxy-2-(4-phenoxyphenyl)ethene (56.5 g) in acetonitrile (780 mL) and methanol (85 mL) is stirred under nitrogen at 0° C. while adding diisopropylethylamine (52.5 mL) followed by 2M trimethylsilyldiazomethane (150 mL) in THF. The reaction is stirred for 2 days at 20° C., and then 2 g of silica is added (for chromatography). The brown-red solution is evaporated in vacuo, the residue dissolved in ethyl acetate and washed well with water then brine, dried and evaporated. The residue is extracted with diethyl ether (3×250 mL), decanting from insoluble oil. Evaporation of the ether extracts gives 22.5 g of 1,1-dicyano-2-methoxy-2-(4-phenoxyphenyl)ethene as a pale orange solid. The insoluble oil is purified by flash chromatography to give 15.0 g of a red-orange oil.

1,1-Dicyano-2-methoxy-2-(4-phenoxyphenyl)ethene (22.5 g) and 1,1-dicyano-2-methoxy-2-(4-phenoxyphenyl) ethene oil (15 g) are treated with a solution of hydrazine hydrate (18 mL) in ethanol (25 mL) and heated on the steam-bath for 1 hour. Ethanol (15 mL) is added followed by water (10 mL). The precipitated solid is collected and washed with ethanol:water (4:1) and then dried in air to give 3-amino-4-cyano-5-(4-phenoxyphenyl)pyrazole as a pale orange solid.

3-Amino-4-cyano-5-(4-phenoxyphenyl)pyrazole (29.5 g) is suspended in formamide (300 mL) and heated under nitrogen at 180° C. for 4 hours. The reaction mixture is cooled to 30° C. and water (300 mL) is added. The solid is collected, washed well with water, then with methanol and dried in air to give of 4-amino-3-(4-phenoxyphenyl)-1H-pyrazolo[3,4-d]pyrimidine.

Example 1a

Synthesis of 1-(3-(4-amino-3-(4-phenoxyphenyl)-1H-pyrazolo[3,4-d]pyrimidin-1-yl)piperidin-1-yl) prop-2-en-1-one (4)

Scheme V.

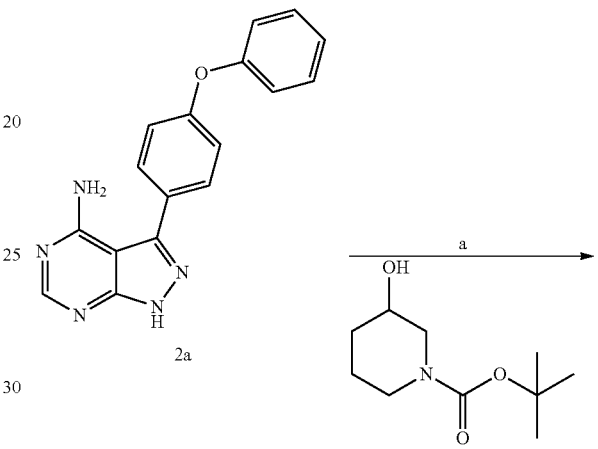

2a

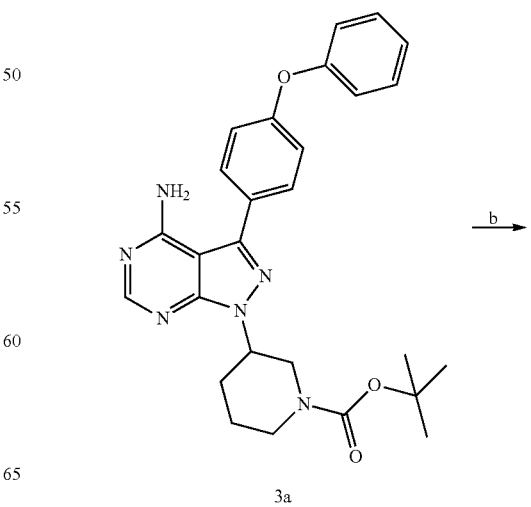

3a

-continued

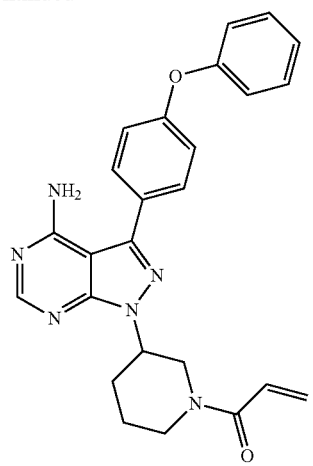

4a

Synthesis of Compound 4a; a) Polymer-Bound Triphenylphosphine (TPP), Diisopropyl Diazodicarboxylate (DIAD), Tetrahydrofuran (THF); b) HCl/Dioxane; then Acryloyl Chloride, Triethylamine (TEA)

Compounds described herein were synthesized by following the steps oultined in Scheme III. A detailed illustrative example of the reaction conditions shown in Scheme III is described for the synthesis of 1-(3-(4-amino-3-(4-phenoxyphenyl)-1H-pyrazolo[3,4-d]pyrimidin-1-yl)piperidin-1-yl)prop-2-en-1-one (Compound 4a).

101 mg of 4-amino-3-(4-phenoxyphenyl)-1H-pyrazolo[3,4-d]pyrimidine and 330 mg of polymer-bound triphenylphosphine(TPP) (polymerlab) were mixed together with 5 mL of tetrahydrofuran (THF). tert-Butyl 3-hydroxypiperidine-1-carboxylate (200 mg; 2.0 equivalents) was added to the mixture followed by the addition of diisopropyl diazodicarboxylate (0.099 mL). The reaction mixture was stirred at room temperature overnight. The reaction mixture was filtered to remove the resins and the reaction mixture was concentrated and purified by flash chromatography (pentane/ethyl acetate=1/1) to give intermediate 3a (55 mg).

Intermediate 3a (48.3 mg) was treated with 1 mL of 4N HCl in dioxane for 1 hour and then concentrated to dryness. The residue was dissolved in dichloromethane and triethylamine (0.042 mL) was added followed by acryl chloride (0.010 mL). The reaction was stopped after 2 hours. The reaction mixture was washed with 5% by weight aqueous citric acid and then with brine. The organic layer was dried with $MgSO_4$, and concentrated. Flash chromatography (with $CH_2Cl_2$/MeOH=25/1) gave 22 mg of compound 4a as a white solid. MS (M+1): 441.2; $^1$H-NMR (400 MHz): 8.26, s, 1H; 7.65, m, 2H; 7.42, m, 2H; 7.1-7.2, m, 5H; 6.7-6.9, m, 1H; 6.1, m, 1H; 5.5-5.7, m, 1H; 4.7, m, 1H; 4.54, m, 0.5H; 4.2, m, 1H; 4.1, m, 0.5H; 3.7, m, 0.5H; 3.2, m, 1H; 3.0, m, 0.5H; 2.3, m, 1H; 2.1, m, 1H; 1.9, m, 1H; 1.6, m, 1H.

Example 1b

Synthesis of 3-(4-amino-3-(4-phenoxyphenyl)-1H-pyrazolo[3,4-d]pyrimidin-1-yl)piperidin-1-yl)-2,3-dihydroxypropan-1-one (5a)

Scheme VI.

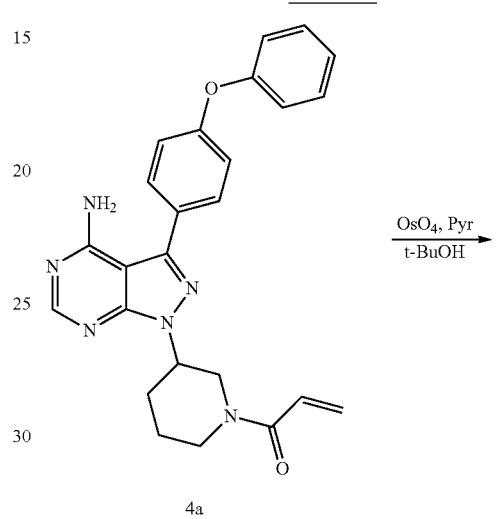

4a

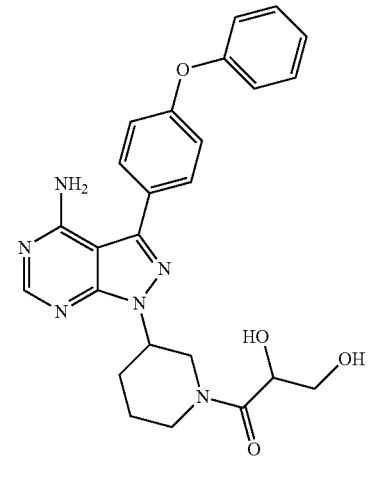

5a

A mixture of 1-(3-(4-amino-3-(4-phenoxyphenyl)-1H-pyrazolo[3,4-d]pyrimidin-1-yl)piperidin-1-yl)prop-2-en-1-one (4a, 220 mg), $OsO_4$ (2.5 wt % in t-BuOH, 6.9 mL) and pyridine (0.04 mL) was stirred at room temperature for 18 hrs. The mixture was worked up with sat. aqueous $NaHSO_3$ solution (6 mL) and stirred for another hour. The aqueous mixture was extracted with EtOAc (30 mL, 15 mL and 5 mL). The combined organic extractants were dried ($Na_2SO_4$), filtered and evaporated in vacuo. The crude was dissolved in small amount of dichloromethane, and purified by flash chromatography (silica, 5% MeOH in CH$_2$Cl$_2$ to 10% MeOH in CH$_2$Cl$_2$) to afford the title compound as a white solid (105 mg).

Example 2

Synthesis of (R)-1-(3-(4-amino-3-(4-phenoxyphenyl)-1H-pyrazolo[3,4-d]pyrimidin-1-yl)piperidin-1-yl)-2-hydroxyethanone (7)

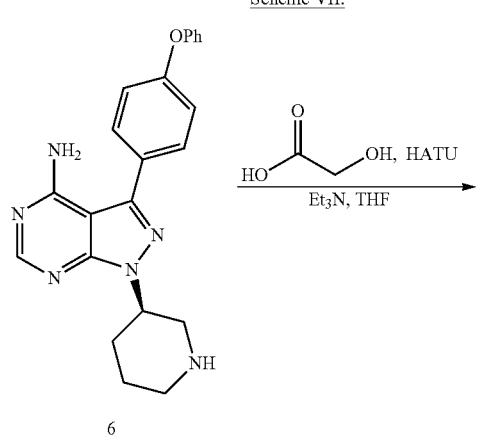

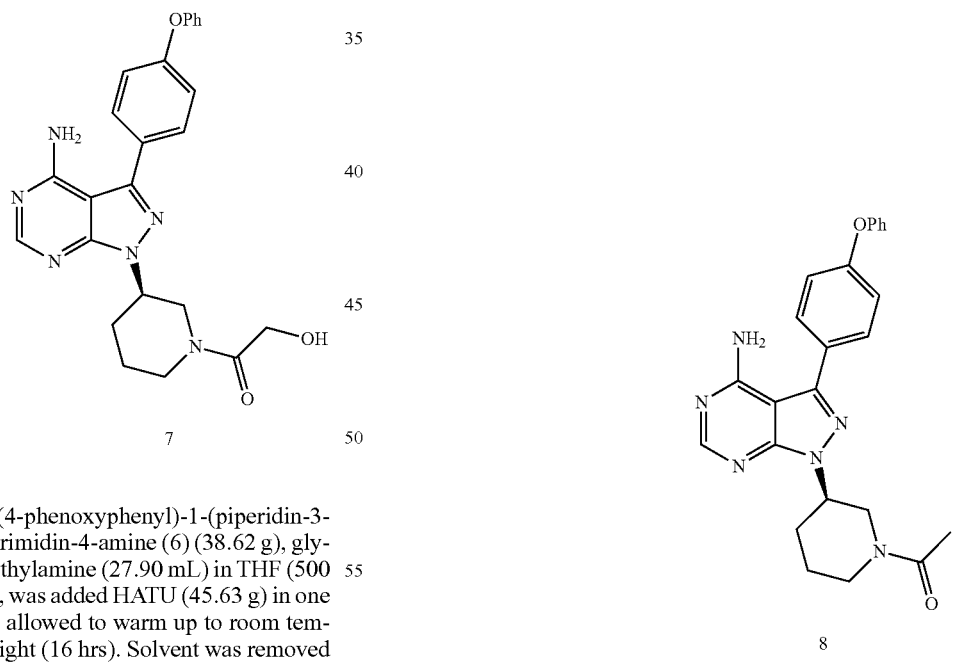

To a mixture of (R)-3-(4-phenoxyphenyl)-1-(piperidin-3-yl)-1H-pyrazolo[3,4-d]pyrimidin-4-amine (6) (38.62 g), glycolic acid (9.13 g) and triethylamine (27.90 mL) in THF (500 mL) stirring in an ice bath, was added HATU (45.63 g) in one portion. The reaction was allowed to warm up to room temperature and stirred overnight (16 hrs). Solvent was removed by rotoevaporation. The residue was diluted with dichloromethane (500 mL), washed with aqueous NaOH solution (10%, 300 mL). The solid was filtered off and the bi-layer system was separated. The organic layer was washed with brine, dried (Na$_2$SO$_4$), filtered and evaporated in vacuo. The residue was triturated with acetonitrile (300 mL) with some heating and cooled to room temperature. The mixture was filtered after sitting at room temperature overnight (16 hrs) and filtered. The solid collected was washed with small amount of acetonitrile and dried under high vacuo to provide the title compound a white powder with slight pink color (34.8 g).

Example 3

Synthesis of (R)-1-(3-(4-amino-3-(4-phenoxyphenyl)-1H-pyrazolo[3,4-d]pyrimidin-1-yl)piperidin-1-yl)ethanone (8)

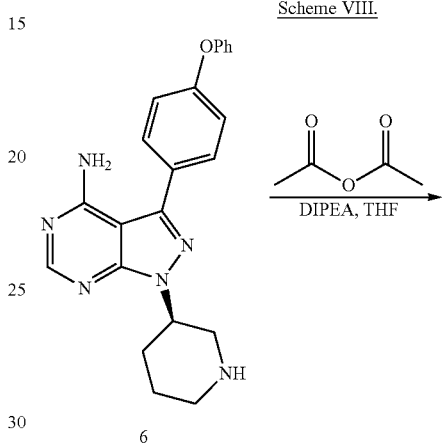

To a solution of (R)-3-(4-phenoxyphenyl)-1-(piperidin-3-yl)-1H-pyrazolo[3,4-d]pyrimidin-4-amine (6) (0.05 g) in THF (1 mL) was added acetic anhydride (12.8 µL) and DIPEA (23.1 µL). The reaction was stirred at room temperature for 2 hours. A sample of the reaction mixture was prepared for LC/MS analysis. 10 µL of the reaction mixture was diluted with H$_2$O:ACN=6:4 to result in a 0.1 mg/mL preparation. LC/MS confirmed that the resulting product (having a m/z of 429) is the title compound.

Example 4

Synthesis of (R)-1-(3-(4-Amino-3-(4-phenoxyphenyl)-1H-pyrazolo[3,4-d]pyrimidin-1-yl)piperidin-1-yl)-3-chloropropan-1-one (9)

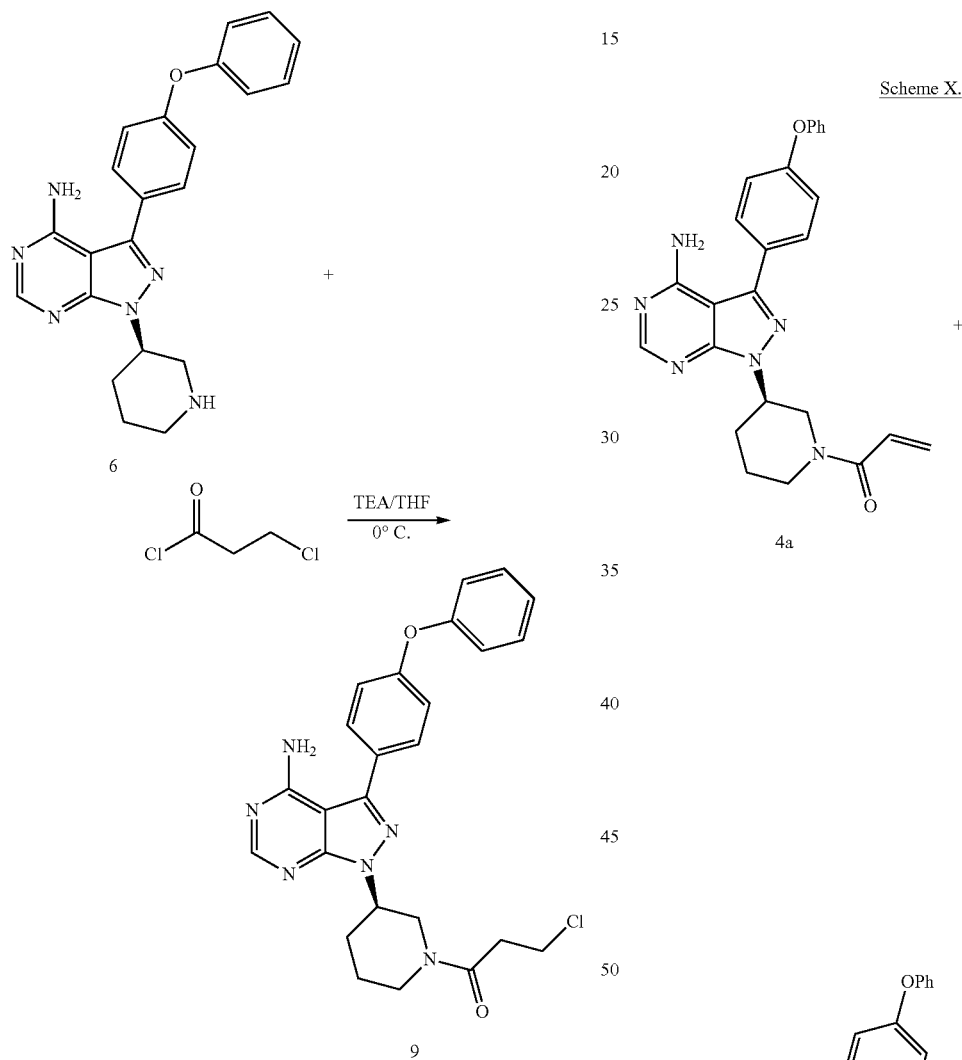

To a solution of (R)-3-(4-phenoxyphenyl)-1-(piperidin-3-yl)-1H-pyrazolo[3,4-d]pyrimidin-4-amine (6) (0.40 g, 1.04 mmol) and TEA (0.29 mL, 2.08 mmol) in THF (15 mL) cooled to 0° C. was added 3-chloropropanoyl chloride (0.132 g, 2.08 mmol). After stirring 1 hr at 0° C., the reaction mixture was diluted with ethyl acetate (100 mL) and washed with water (50 mL). The organic layer was dried (MgSO$_4$), filtered and concentrated to collect 0.49 g of a white solid. The white solid was subjected to flash chromatography (5% MeOH/EtOAc) to provide 0.31 g (62%) of (R)-1-(3-(4-amino-3-(4-phenoxyphenyl)-1H-pyrazolo[3,4-d]pyrimidin-1-yl)piperidin-1-yl)-3-chloropropan-1-one (9) as a white solid. $^1$H NMR (300 MHz, DMSO) δ 8.25 (s, 1H), 7.64 (d, 2H, J=8.5 Hz), 7.40 (m, 2H), 7.20-7.00 (m, 7H), 4.60 (m, 1H), 4.12-3.10 (m, 6H), 2.94-1.60 (m, 6H).

Example 5

Synthesis of 1-((R)-3-(4-amino-3-(4-phenoxyphenyl)-1H-pyrazolo[3,4-d]pyrimidin-1-yl)piperidin-1-yl)-3-((S)-3-(4-amino-3-(4-phenoxyphenyl)-1H-pyrazolo[3,4-d]pyrimidin-1-yl)piperidin-1-yl)propan-1-one (10)

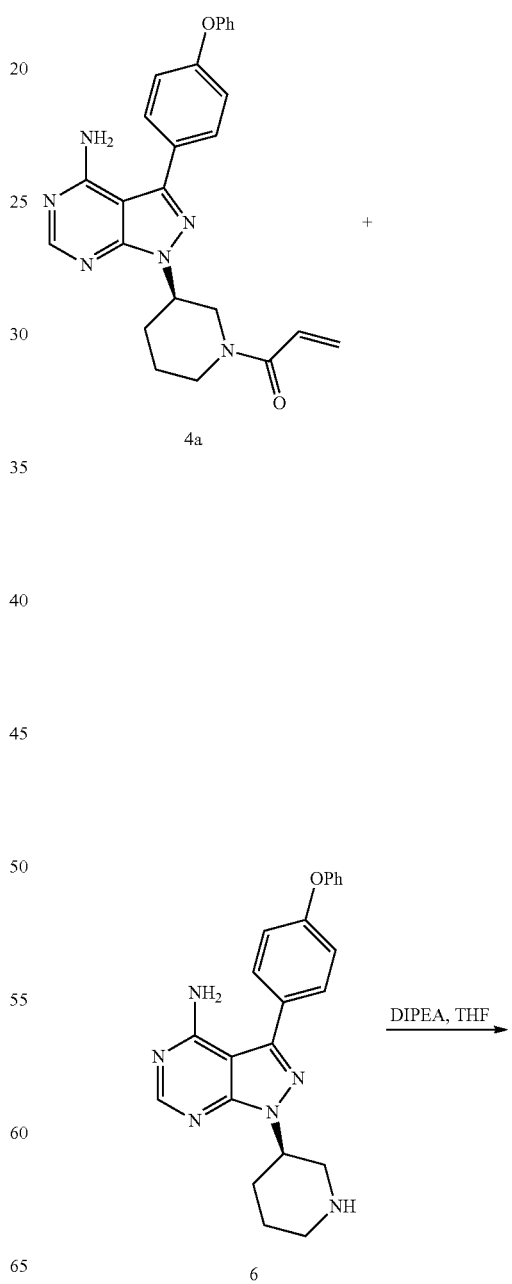

-continued

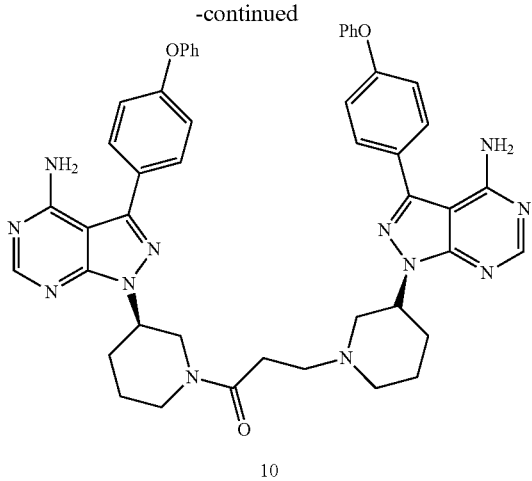

10

The desired title compound (10) is synthesized in basic conditions. For example, compound 4a (52 mg) and compound 6 (46 mg) were dissolved in anhydrous THF (0.6 mL). DIPEA (20 μL) is added to the reaction mixture and heated to 30-35 deg C. The reaction was stirred continuously for 48 hours. Prep TLC (acetone:MeOH 1:1) of the reaction mixture resulted in the desired title compound 10.

Therapeutic Uses of Inhibitor Compounds

Example 6

Btk In Vitro Inhibitory Activity

The Btk $IC_{50}$ of compounds disclosed herein is determined in both an acellular kinase assay and in a cellular functional assay of BCR-induced calcium flux as described below.

Btk kinase activity is determined using a time-resolved fluorescence resonance energy transfer (TR-FRET) methodology. Measurements are performed in a reaction volume of 50 μL using 96-well assay plates. Kinase enzyme, inhibitor, ATP (at the $K_m$ for the kinase), and 1 μM peptide substrate (Biotin-AVLESEEELYSSARQ-NH$_2$) are incubated in a reaction buffer composed of 20 mM Tris, 50 mM NaCl, MgCl$_2$ (5-25 mM depending on the kinase), MnCl$_2$ (0-10 mM), 1 mM DTT, 0.1 mM EDTA, 0.01% bovine serum albumin, 0.005% Tween-20, and 10% DMSO at pH 7.4 for one hour. The reaction is quenched by the addition of 1.2 equivalents of EDTA (relative to divalent cation) in 25 μL of 1× Lance buffer (Perkin-Elmer). Streptavidin-APC (Perkin-Elmer) and Eu-labeled p-Tyr100 antibody (Perkin-Elmer) in 1× Lance buffer are added in a 25 μL volume to give final concentrations of 100 nM and 2.5 nM, respectively, and the mixture is allowed to incubate for one hour. The TR-FRET signal is measured on a multimode plate reader with an excitation wavelength ($\lambda_{Ex}$) of 330 m and detection wavelengths ($\lambda_{Em}$) of 615 and 665 mn. Activity iss determined by the ratio of the fluorescence at 665 mn to that at 615 mn. For each compound, enzyme activity iss measured at various concentrations of compound. Negative control reactions are performed in the absence of inhibitor in replicates of six, and two no-enzyme controls are used to determine baseline fluorescence levels. Inhibition constants, $K_i$(app), are obtained using the program BatchK$_i$ (Kuzmic et al. (2000), Anal. Biochem. 286:45-50). $IC_{50}$s are obtained according to the equation:

$$IC_{50}=\{Ki(\text{app})/(1+[ATP]/K_m^{ATP})\}+[E]_{total}/2;$$

For all kinases, $[ATP]=K_m^{ATP}$, [Btk]total=0.5 nM and $[Lck]_{total}$=6 nM.

Calcium flux fluoresence-based assays are performed in a FlexStation II384 fluorometric imaging plate reader (Molecular Devices) according to manufacturer instructions. In brief, actively growing Ramos cells (ATCC) in RPM1 medium supplemented with 10% FBS (Invitrogen) are washed and re-plated in low serum medium at approximately $5\times10^5$ cells per 100 μl per well in a 96-well plate. Compounds to be assayed are dissolved in DMSO and then diluted in low serum medium to final concentrations ranging from 0 to 10 μM (at a dilution factor of 0.3). The diluted compounds are then added to each well (final DMSO concentration was 0.01%) and incubated at 37 degree in 5% $CO_2$ incubator for one hour. Afterwards, 100 μl of a calcium-sensitive dye (from the Calcium 3 assay kit, Molecular Devices) is added to each well and incubated for an additional hour. The compound-treated cells are stimulated with a goat anti-human IgM antibody (80 ug/ml; Jackson ImmunoResearch) and read in the FlexStation II384 using a $\lambda_{Ex}$=485 nm and $\lambda_{Em}$=538 μm for 200 seconds. The relative fluorescence unit (RFU) and the $IC_{50}$ were recorded and analyzed using a built-in SoftMax program (Molecular devices).

Example 7

Inhibition of Btk

The properties of the compounds disclosed herein are further characterized by assaying a number of cellular biochemical and functional endpoints. In particular, we sought to assess the selectivity of these compounds for inhibition of Btk versus the closely related protein kinases Lck, Lyn, and Syk. In anti-IgM-stimulated Ramos cells (a human B cell line), are assayed Btk-dependent phosphorylation of PLC-γ1; Lyn and Syk-dependent phosphorylation of tyrosine 551 on Btk; and BCR-activated calcium flux. The effect of compounds disclosed herein on Jurkat cells are measured wherein a human T cell line in which Lck and Itk, but not Btk are required for T cell receptor mediated $Ca^{2+}$ flux.

Example 8

Use of a Compound Described Herein to Treat Rheumatoid Arthritis

The in vivo efficacy of the compounds described herein are evaluated in a mouse model of rheumatoid arthritis. Arthritis is induced in Balb/c mice by administration of anti-collagen antibodies and lipopolysaccharide (LPS). See Nandakumar et al. (2003), *Am. J. Pathol.* 163:1827-1837. Female Balb/c mice are treated with 100 mg/kg of Chemicon mAb cocktail to Type II collagen intravenously on Day 0 and 1.25 mg/kg of LPS intraperitoneally on Day 1. A test compound is administered orally in a methylcellulose-based aqueous suspension formulation at 1, 3, 10 and 30 mg/kg once daily starting on Day 2 through Day 12. Blood samples are collected at 0.5 and 2 hours post dose of the test compound administration on Day 12. The serum concentrations of the test compound are quantified by LC/MS/MS. Twenty four hours post dose, levels of the test compound below the level of quantitation.

Example 9

Inhibition of Mast Cell Degranulation

Human CD34+ cells differentiated to mast cells by 9 weeks in culture in the presence of lng/ml IL-3, 50 ng/ml IL-6, 100 ng/ml SCF. Cells are incubated with IgE+IL-4 for 4 days and then degranulation is induced by cross-linking with anti-IgE. Degranulation quantitated using hexosaminidase assay. The $IC_{50}$ in MC degranulation of the compounds are determined Compounds with desired $IC_{50}$ values are used for the treatment of inflammatory diseases, such as asthma.

Example 10

Pharmaceutical Compositions

The compositions described below are presented with a compound described herein for illustrative purposes; any of the compounds described herein are optionally used in such pharmaceutical compositions.

Example 10a

Parenteral Composition

To prepare a parenteral pharmaceutical composition suitable for administration by injection, 100 mg of a water-soluble salt of a compound of Formula (I), (IA), (II), (IIIA), (IIIB), (IIIC), (IIID), or (IV) or other pyrazolopyrimidine compounds described herein is dissolved in DMSO and then mixed with 10 mL of 0.9% sterile saline. The mixture is incorporated into a dosage unit form suitable for administration by injection.

Example 10b

Oral Composition

To prepare a pharmaceutical composition for oral delivery, 100 mg of a compound of Formula (I), (IA), (II), (IIIA), (IIIB), (IIIC), (IIID), or (IV) or other pyrazolopyrimidine compounds described herein is mixed with 750 mg of starch. The mixture is incorporated into an oral dosage unit for, such as a hard gelatin capsule, which is suitable for oral administration.

Example 10c

Sublingual (Hard Lozenge) Composition

To prepare a pharmaceutical composition for buccal delivery, such as a hard lozenge, mix 100 mg of a compound of Formula (I), (IA), (II), (IIIA), (IIIB), (IIIC), (IIID), or (IV) or other pyrazolopyrimidine compounds described herein, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 10d

Inhalation Composition

To prepare a pharmaceutical composition for inhalation delivery, 20 mg of a compound of Formula (I), (IA), (II), (IIIA), (IIIB), (IIIC), (IIID), or (IV) or other pyrazolopyrimidine compounds described herein is mixed with 50 mg of anhydrous citric acid and 100 mL of 0.9% sodium chloride solution. The mixture is incorporated into an inhalation delivery unit, such as a nebulizer, which is suitable for inhalation administration.

Example 10e

Rectal Gel Composition

To prepare a pharmaceutical composition for rectal delivery, 100 mg of a compound of Formula (I), (IA), (II), (IIIA), (IIIB), (IIIC), (IIID), or (IV) or other pyrazolopyrimidine compounds described herein is mixed with 2.5 g of methylcellulose (1500 mPa), 100 mg of methylparaben, 5 g of glycerin and 100 mL of purified water. The resulting gel mixture is then incorporated into rectal delivery units, such as syringes, which are suitable for rectal administration.

Example 10f

Topical Gel Composition

To prepare a pharmaceutical topical gel composition, 100 mg of a compound of Formula (I), (IA), (II), (IIIA), (IIIB), (IIIC), (IIID), or (IV) or other pyrazolopyrimidine compounds described herein is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 10g

Ophthalmic Solution Composition

To prepare a pharmaceutical ophthalmic solution composition, 100 mg of a compound of Formula (I), (IA), (II), (IIIA), (IIIB), (IIIC), (IIID), or (IV) or other pyrazolopyrimidine compounds described herein is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

What is claimed is:
1. A compound having the structure of Formula (IV):

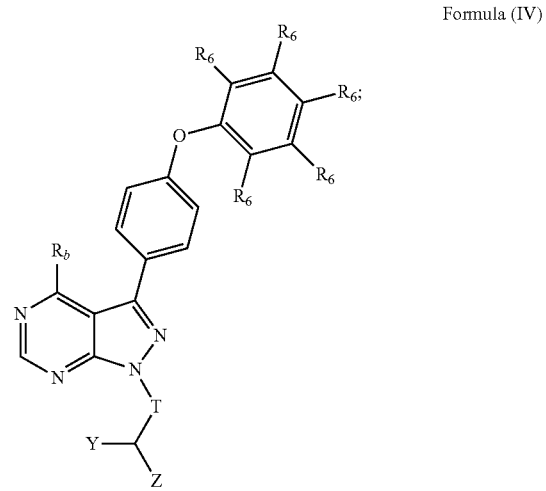

Formula (IV)

wherein:
T is a bond;
Y and Z together with the carbon atom to which they are attached form a $C_2$-$C_{10}$heterocycloalkyl, optionally substituted with at least one X;

wherein when Y and Z together with the carbon atom to which they are attached form a nitrogen atom-containing C$_2$-C$_{10}$heterocycloalkyl the nitrogen atom of the C$_2$-C$_{10}$heterocycloalkyl is substituted with W and the carbon atoms of the C$_2$-C$_{10}$heterocycloalkyl are optionally substituted with at least one X;

W is selected from C(=O)O-J, C(=O)NR$_2$-J, C(=NR$_2$)-J, —C(=NR$_2$)NR$_2$-J, C(=N—OR$_3$)-J, C(=S)-J, S(=O)$_v$-J, S(=O)$_v$O-J;

X is F, Cl, Br, I, —CN, —NO$_2$, —OR$_3$, —N(R$_2$)$_2$, —SR$_2$, —C$_1$-C$_6$alkyl, —C(=O)R$_2$, —OC(=)R$_2$, —NR$_2$C(=O)N(R$_2$)$_2$, —C(=O)N(R$_2$)$_2$, —C(=NR$_2$)N(R$_2$)$_2$, —C(=N—OR$_2$)N(R$_2$)$_2$, —C(=S)R$_2$, —S(=O)$_v$R$_2$, —OS(=O)$_v$R$_2$, —NR$_2$C(=O)OR$_2$, —NR$_2$S(=O)$_v$R$_2$;

J is methyl, ethyl, n-propyl, iso-propyl, n-butyl, iso-butyl, or tert-butyl optionally substituted with at least one R$_1$;

v is 1 or 2;

R$_b$ is NH$_2$;

R$_1$ is selected from F, Cl, Br, I, —CN, —NO$_2$, —SR$_2$, —OR$_3$, C$_1$-C$_6$alkyl, C$_1$-C$_6$haloalkyl, C$_1$-C$_6$hydroxyalkyl, —OC$_1$-C$_6$haloalkyl, C$_1$-C$_6$heteroalkyl, C$_3$-C$_6$cycloalkyl, C$_2$-C$_6$heterocycloalkyl, phenyl, —NR$_2$S(=O)$_2$R$_2$, —S(=O)$_2$N(R$_2$)$_2$, —C(=O)CF$_3$, —C(=O)NR$_2$S(=O)$_2$R$_2$, —S(=O)$_2$NR$_2$C(=O)R$_2$, —NR$_2$C(=O)R$_8$, —NR$_2$C(=O)N(R$_2$)$_2$, —CO$_2$R$_2$, —OC(=O)R$_2$, —OC(=O)R$_2$, —C(=O)N(R$_2$)$_2$, —OS(=O)$_2$R$_2$, —OS(=O)$_2$OR$_2$, —S(=O)R$_2$, —S(=O)$_2$R$_2$, and —SO$_3$H;

R$_2$ is H, C$_1$-C$_6$alkyl, C$_1$-C$_6$haloalkyl, C$_1$-C$_6$hydroxyalkyl, or C$_3$-C$_6$cycloalkyl;

R$_3$ is H, methyl, ethyl, n-propyl, iso-propyl, n-butyl, iso-butyl, tert-butyl, or SO$_3$H;

each R$_6$ is independently selected from H, —OR$_3$, C$_1$-C$_6$alkyl, C$_1$-C$_6$haloalkyl, C$_1$-C$_6$hydroxyalkyl, —OC$_1$-C$_6$haloalkyl, C$_1$-C$_6$heteroalkyl, C$_3$-C$_6$cycloalkyl, C$_2$-C$_6$heterocycloalkyl, phenyl, —NR$_2$S(=O)$_2$R$_2$, —S(=O)$_2$N(R$_2$)$_2$, —C(=O)CF$_3$, —C(=O)NR$_2$S(=O)$_2$R$_2$, —S(=O)$_2$NR$_2$C(=O)R$_2$, —N(R$_2$)$_2$, wherein optionally the two R$_2$ groups of N(R$_2$)$_2$ and the nitrogen atom to which they are attached form a C$_2$-C$_6$ heterocycloalkyl ring, —NR$_2$C(=O)R$_2$, —NR$_2$C(=O)N(R$_2$)$_2$, —CO$_2$R$_2$, —C(=O)R$_2$, —OC(=O)R$_2$, —C(=O)N(R$_2$)$_2$, —OS(=O)$_2$R$_2$, —OS(=O)$_2$OR$_2$, —S(=O)R$_2$, —S(=O)$_2$R$_2$, and —SO$_3$H, wherein at least one R$_6$ is —OH;

R$_8$ is an optionally substituted C$_1$-C$_6$alkyl, an optionally substituted C$_2$-C$_6$alkenyl, an optionally substituted C$_2$-C$_6$alkynyl, or an optionally substituted C$_3$-C$_6$cycloalkyl; or a pharmaceutically acceptable salt thereof.

2. The compound of claim 1 wherein W is C(=O)J.

3. The compound of claim 2 wherein J is substituted with at least one R$_1$.

4. The compound of claim 3 wherein R$_1$ is selected from F, Cl, Br, I, —CN, —NO$_2$, —SR$_2$, —OR$_3$, C$_1$-C$_6$alkyl, C$_1$-C$_6$haloalkyl, C$_1$-C$_6$hydroxyalkyl, —OC$_1$-C$_6$haloalkyl, C$_1$-C$_6$heteroalkyl, C$_3$-C$_6$cycloalkyl, C$_2$-C$_6$heterocycloalkyl.

5. The compound of claim 2 wherein Y and Z together with the carbon atom to which they are attached form a nitrogen atom-containing C$_2$-C$_{10}$heterocycloalkyl selected from:

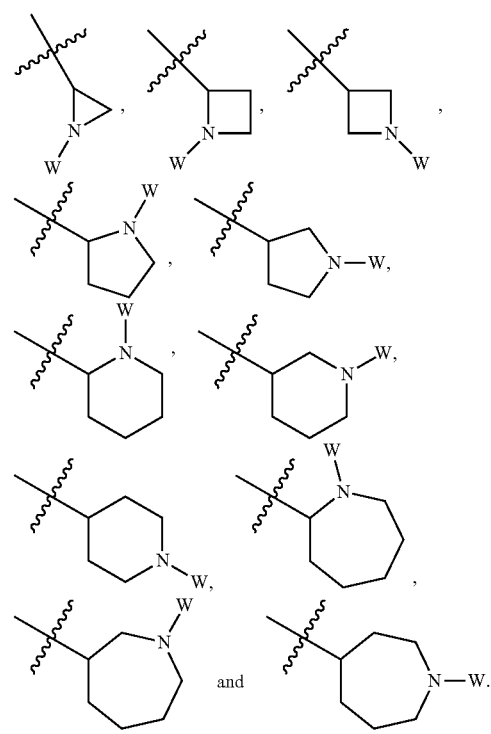

6. The compound of claim 5 wherein C$_2$-C$_{10}$heterocycloalkyl is

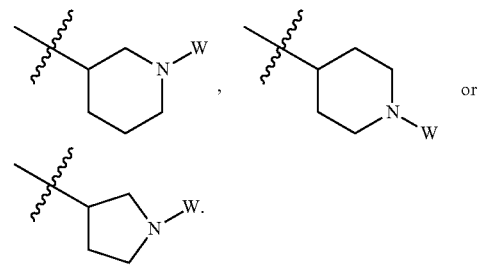

7. The compound of claim 1 wherein J is substituted with one R$_1$.

8. The compound of claim 1 wherein J is substituted with two R$_1$.

9. The compound of claim 7 wherein R$_1$ is selected from F, Cl, Br, I, —CN, and —OR$_3$.

10. A pharmaceutical formulation comprising a therapeutically effective amount of a compound of claim 1, and a pharmaceutically acceptable excipient.

11. The compound of claim 6 wherein C$_2$-C$_{10}$heterocycloalkyl is

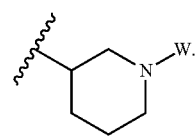

12. The compound of claim 11 wherein J is ethyl optionally substituted with at least one R$_1$; and R$_1$ is selected from F, Cl, Br, I, —CN, —SR$_2$, and —OR$_3$.

13. The compound of claim 12 wherein J is unsubstituted ethyl.

14. The compound of claim 12 wherein J is —CH(OH)CH$_2$(OH).

* * * * *